United States Patent [19]

Haviv et al.

[11] Patent Number: 5,110,904
[45] Date of Patent: May 5, 1992

[54] LHRH ANALOGS

[75] Inventors: Fortuna Haviv, Deerfield; Jonathan Greer, Chicago, both of Ill.

[73] Assignee: Abbott Laboratories, Abbott Park, Ill.

[21] Appl. No.: 548,512

[22] Filed: Jul. 10, 1990

Related U.S. Application Data

[63] Continuation-in-part of Ser. No. 390,572, Aug. 7, 1989, which is a continuation-in-part of PCT/US89/00528, Feb. 9, 1989, which is a continuation-in-part of Ser. No. 154,681, Feb. 10, 1988, abandoned.

[51] Int. Cl.$^5$ .................. C07K 7/20; A61K 37/24
[52] U.S. Cl. .................... 530/313; 530/328
[58] Field of Search ............ 530/313, 328; 514/15

[56] References Cited

U.S. PATENT DOCUMENTS

| 4,444,759 | 4/1984 | Rivier et al. |
| 4,493,934 | 1/1985 | Veber et al. |
| 4,632,979 | 12/1986 | Coy et al. |
| 4,689,396 | 8/1987 | Roeske et al. |
| 4,690,916 | 9/1987 | Nestor et al. |
| 4,760,053 | 7/1988 | Labrie ................ 514/15 |
| 4,801,577 | 1/1989 | Nester, Jr. et al. ........ 530/313 |
| 4,851,385 | 7/1989 | Roeske ................ 514/15 |
| 4,866,160 | 9/1989 | Coy et al. ............ 530/313 |
| 4,935,491 | 6/1990 | Folkers et al. |
| 5,003,011 | 3/1991 | Coy et al. ............ 530/313 |

FOREIGN PATENT DOCUMENTS

WO89/01944 3/1989 PCT Int'l Appl.

OTHER PUBLICATIONS

Thiasrivongs et al., *J. of Hypertension*, 7, (suppl. 2): 521-523, 1989.
Stewart et al., Solid Phase Peptide Synthesis, Pierce Chem. Co., 1984.
Coy et al., J. Med. Chem. 19 423 (1976).

Primary Examiner—Howard E. Schain
Assistant Examiner—Susan M. Perkins
Attorney, Agent, or Firm—Jerry F. Janssen; Steven R. Crowley

[57] ABSTRACT

The present invention relates to novel "pseudo" nonapeptide and decapeptide derivatives of LHRH. More particularly the present invention relates to derivatives of LHRH wherein the nitrogen atom of at least one of the amide bonds has been alkylated.

10 Claims, 1 Drawing Sheet

LHRH ANALOGS

This is a continuation-in-part of U.S. patent application Ser. No. 390,572, filed Aug. 7, 1989, which is a continuation in part of patent application Ser. No. PCT/US89/00528, filed Feb. 9, 1989, which is a continuation-in-part of U.S. patent application Ser. No. 154,681, filed Feb. 10, 1988.

TECHNICAL FIELD

The present invention relates to novel "pseudo" nonapeptide and decapeptide analogs of LHRH wherein the nitrogen atom of at least one of the amide bonds is alkylated. The invention also relates to processes for preparing such compounds, to pharmaceutical compositions containing such compounds and to the use of such compounds for modulating levels of sex hormones in male or female mammals.

BACKGROUND ART

Luteinizing Hormone Releasing Hormone, known as LHRH or GnRH, is a decapeptide with the following formula:

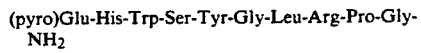
(pyro)Glu-His-Trp-Ser-Tyr-Gly-Leu-Arg-Pro-Gly-NH₂

LHRH is released from the hypothalamus and binds to a receptor on the pituitary gland, causing the release of LH (Luteinizing Hormone) and FSH (Follicle-Stimulating Hormone). Subsequently, LH and FSH act on the gonads to stimulate the synthesis of steroid sex hormones. The pulsatile release of LHRH, and thereby the release of LH and FSH, controls the reproductive cycle in domestic animals and humans. Acute doses of LHRH agonists increase the levels of LH and steroid sex hormones in both animals and humans. Paradoxically, chronic doses of these agonists suppress the levels of LH and steroid hormones. Consequently, the effect of multiple doses of LHRH agonists is to suppress estrogen formation in the female and suppress testosterone formation in the male. The same effect is observed in both animals and humans after administration of acute or chronic doses of LHRH antagonists. LHRH agonists are currently used or under clinical investigation for the treatment of several hormone dependent diseases such as prostate cancer, benign prostatic hypertrophy, endometriosis, uterine fibroids, precocious puberty and breast cancer. They have also been used as contraceptives For a review of LHRH analogs see J. Sandow, et al. in "Hypothalamic Hormones. Chemistry, Physiology, and Clinical Applications", edited by D. Gupta and W. Voeters, p. 307 (1978).

Biologically active LHRH analogs have been studied in animals and humans. LHRH analogs have been found to be effective by either intraveneous, subcutaneous, or depot administration. Intranasal and intravaginal administrations are effective only at very high doses. All of the reported LHRH analogs show 0.1% to 1% potency following oral administration when compared to intraveneous doses. One of the major reasons for this low potency is that these peptides are degraded in the stomach by various proteolytic enzymes before reaching the blood system. It would be desirable to prepare analogs of LHRH that are stable against proteolytic enzymes and are biologically potent after oral administration in animals and humans.

SUMMARY OF THE INVENTION

The present invention relates to novel "pseudo" nonapeptide and decapeptide derivatives of LHRH. More particularly the present invention relates to derivatives of LHRH wherein the nitrogen atom of at least one of the amide bonds is alkylated.

DISCLOSURE OF THE INVENTION

Figure 1:
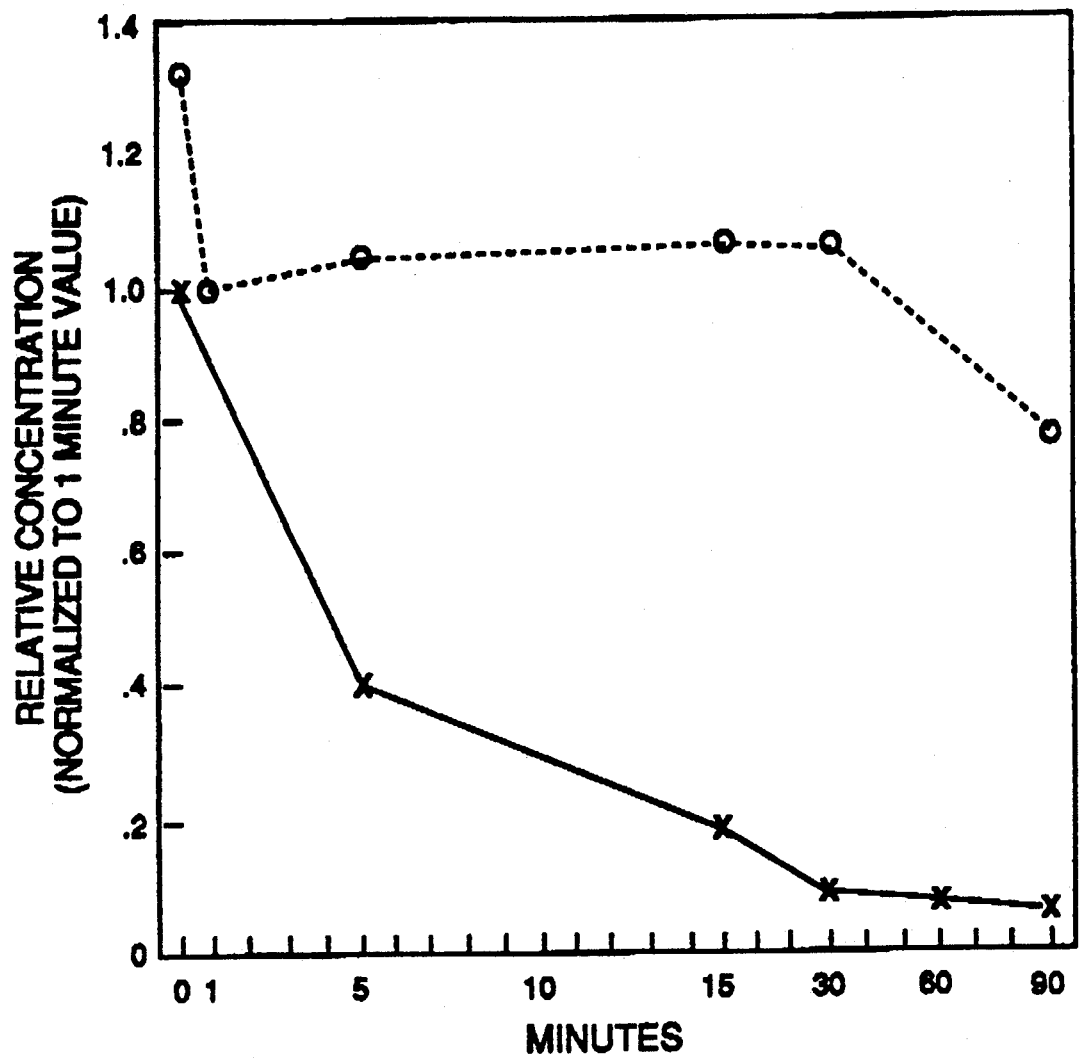
FIG. 1 is a comparison of the in vitro intestinal stability of (pyro)Glu-His-Trp Ser-Tyr-D-Leu-Leu-Arg-Pro-NHEt versus (pyro)Glu-His-Trp-N-Me-Ser-Tyr-D-Leu-Leu-Arg-Pro-NHEt.

The compounds of the present invention are of the formula:

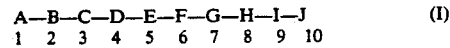

$$A-B-C-D-E-F-G-H-I-J \qquad (I)$$
$$1\ \ 2\ \ 3\ \ 4\ \ 5\ \ 6\ \ 7\ \ 8\ \ 9\ \ 10$$

or a pharmaceutically acceptable salt thereof; wherein A is an amino acyl residue selected from the group consisting of L-pyroglutamyl, D-pyroglutamyl, N-acetyl-L-prolyl, N-acetyl-D-prolyl, N-acetyl-L-delta³,⁴-prolyl, N-acetyl-D-delta³,⁴-prolyl, N-acetyl-L phenylalanyl, N-acetyl-D-phenylalanyl, N-acetyl-L-3-(2-thienyl)alanyl, N-acetyl-D-3-(2-thienyl)alanyl, N-acetyl-L-3-(4-chlorophenyl)alanyl, N-acetyl-D-3-(4-chlorophenyl)alanyl, N-acetyl-L-3-(4-fluorophenyl)alanyl, N-acetyl-D-3-(4-fluorophenyl)alanyl, N-acetyl-L-3-(4-bromophenyl)alanyl, N-acetyl-D-3-(4-bromophenyl)alanyl, N-acetyl-L-3-(4-methylphenyl)alanyl, N-acetyl-D-3-(4-methylphenyl)alanyl, N-acetyl-L-3-(pentamethylphenyl)alanyl, N-acetyl-D-3-(pentamethylphenyl)alanyl, N-acetyl-L-3-(3,4,5-trimethylphenyl)alanyl, N-acetyl-D-3-(3,4,5-trimethylphenyl)alanyl, N-acetyl-L-3-tryptyl(N-indole-methyl), N-acetyl-D-3-tryptyl(N-indole-methyl), N-acetyl-L-tryptyl(N-indole-formyl), N-acetyl-D-tryptyl-(N-indole-formyl), N-acetyl-L-3-(1-adamantyl)alanyl, N-acetyl-D-3-(1-adamantyl)alanyl, N-acetyl-L-5-fluorotryptyl(N-indole-formyl), N-acetyl-D-5-fluorotryptyl(N-indole-formyl), N-acetyl-L-3-(2-naphthyl)alanyl, N-acetyl-L-3-(3-benzothienyl)alanyl, N-acetyl-D-3-(3-benzothienyl)alanyl, N-acetyl-L-3-(3-benzoxazolyl)alanyl, N-acetyl-D-3-(3-benzoxazolyl)alanyl, N-acetyl-alpha-methyl L 3 (4-chlorophenyl)alanyl, N-acetyl-alpha-methyl D-3 (4-chlorophenyl)alanyl, N-acetyl-L-3-(4-trifluoromethylphenyl)alanyl, N-acetyl-D-3-(4-trifluoromethylphenyl)alanyl, N-acetyl-L-tyrosyl, N-acetyl-D-tyrosyl, N-acetyl-L-O-methyl-tyrosyl, N-acetyl-D-O-methyl-tyrosyl, N-acetyl-D-3-(2-naphthyl)alanyl, N-acetyl-L-3-(1-naphthyl)alanyl, N-acetyl-D-3-(1-naphthyl)alanyl, N-acetylsarcosyl, N-acetyl-L-3-(cyclohexyl)alanyl, N-acetyl-D-3-(cyclohexyl)alanyl, N-acetylglycyl, L-N-acetyl-N-methylalanyl, N-acetyl-N-methyl-D-alanyl, N-acetyl-alpha-methyl-L-phenylalanyl, N-acetyl-alpha-methyl-D-phenylalanyl, N-acetyl-D-phenylalanyl, N-acetyl-L-phenylalanyl, N-formyl-sarcosyl, N-formyl-N-methyl-L-alanyl, N-formyl-N-methylalanyl, 2-N-beta-(ethylaminocarbonyl)-N-epsilon-(ethylamido)glutam yl, N-delta-ethyl-glutamyl, L-prolyl, D-prolyl, L-delta³,⁴-prolyl, D-delta³,⁴-prolyl, L-phenylalanyl, D-phenylalanyl, L-3-(4-methylphenyl)alanyl), D-3-(4-methylphenyl)alanyl, L-3-(4-nitrophenyl)alanyl, D-3-(4-nitrophenyl)alanyl, L-3-(4-acetylaminophenyl)alanyl, D-3-(4-acetylaminophenyl- )alanyl, L-3-(4-chlorophenyl)alanyl, D-3-(4-chlorophenyl)alanyl, L-3-(4-fluorophenyl)alanyl, D-3-(4-fluorophenyl)alanyl, alpha-methyl-L-3-(4-chlorophenyl)alanyl, alpha-methyl-D-3-(4-chlorophenyl)alanyl, L-3-(4-trifluoromethylphenyl)alanyl, D-3-(4-trifluoromethylphenyl)alanyl, L-tyrosyl, D-tyrosyl, L-O-methyl-tyrosyl, D-O-methyl-tyrosyl, sarcosyl, glycyl, L-N-methylalanyl, N-methyl-D-alanyl, N-methyl-L-pyroglutamyl, N-methyl-D-pyroglutamyl, alpha-methyl-L-phenylalanyl, alpha-methyl-D-phenylalanyl, N-acetyl-alpha-aza-3-(4-chlorophenyl)alanyl, N-acetyl-alpha-aza-3-(4-fluorophenyl)alanyl, N-acetyl-alpha-aza-3-(2-naphthyl)alanyl, N-acetyl-alpha-aza-3-(1-naphthyl)alanyl, N-acetyl-alpha-aza-alanyl, N-acetyl-alpha-azaglycyl, N-acetyl-alpha-aza-sarcosyl, N-acetyl-alpha-aza-3-(4-methylphenyl)alanyl, N-acetyl-alpha-azacyclohexylalanyl, N-acetyl-alpha-aza-3-(1-adamantyl)alanyl, N-acetyl-alpha-aza-tyrosyl(O-methyl), N-acetyl-alpha-aza-3-(3-benzothienyl)alanyl, N-acetyl-alpha-aza-phenylalanyl, N-methylalpha-aza-pyroglutamyl, N-acetyl-alpha-aza-3-(2-thienyl)alanyl, N-acetyl-alpha-aza-3-(3-benzoxazolyl)alanyl, N-acetyl-alpha-aza-3-(3,4,5-trimethylphenyl)alanyl, N-acetyl-alph-aza-3-(pentamethylphenyl)alanyl, N-acetyl-N-alpha-methyl-alpha-aza-3-(2-naphthyl)alanyl, N-acetyl-N-alpha-methyl-alpha-aza-3-(1-naphthyl)alanyl, N-acetyl-N-alpha-methyl-alpha-aza-3-(4-chlorophenyl)alanyl, N-acetyl-N-alpha-methyl-alpha-aza-3-(4-fluorophenyl)alanyl, N-acetyl-N-alpha-methyl-alpha-aza-3-(4-methylphenyl)alanyl, N-acetyl-N-alpha-methyl-alpha-aza-3-(4-methoxyphenyl)alanyl, N-acetyl-N-alpha-methyl-alpha-aza (1-adamantyl)alanyl, N-acetyl-N-alpha-methyl alpha-aza-3-(phenyl)alanyl, N-acetyl-N-alpha-methyl-alpha-aza-alanyl, N-acetyl-N-alpha-methyl alpha-aza-3-(cyclohexyl)alanyl, N-acetyl-N-alpha-methyl-alpha-aza-3-(benzthienyl)alanyl, N-acetyl-N-alpha-methyl-alpha-aza-3-(benzoxazolyl)alanyl, N-acetyl-N-alpha-methyl-alpha-aza-3-(3,4,5-trimethylphenyl)alanyl, N-acetyl-N-alpha-methyl-alpha-aza-3-(pentamethylphenyl) alanyl and N-acetyl-N-alpha-methyl-alpha-aza-3-(2-thienyl)alanyl phenyl)alanyl;

B is absent or an amino acyl residue selected from the group consisting of L-histidyl, D-histidyl, L-tryptyl, D-tryptyl, L-tryptyl(N-indole-methyl), D-tryptyl(N-indole-methyl), L-phenylalanyl, D-phenylalanyl, L-3-(2-naphthyl)-alanyl, D-3-(2-naphthyl)-alanyl, L-3-(1-naphthyl)-alanyl, D-3-(1-naphthyl)-alanyl, L-3-(3-benzoxazolyl)alanyl, D-3-(3-benzoxazolyl)alanyl, L-3-(3-pyridyl)-alanyl, L-3-(2-pyridyl)-alanyl, D-3-(3-pyridyl)-alanyl, D-3-(2-pyridyl)-alanyl, L-3-(2-thiazolyl)alanyl, D-3-(2-thiazolyl)-alanyl, L-3-(3-benzthienyl)alanyl, D-3-(3-benzthienyl)alanyl, L-3-(2-benzthienyl)alanyl, D-(2-benzthienyl)alanyl, L-3-(2-thienyl)-alanyl, D-3-(2-thienyl)-alanyl, L-cyclohexylalanyl, D-cyclohexylalanyl, L-3-(3-pyrazolyl)alanyl, D-3-(3-pyrazolyl)alanyl, L-3-(4-chlorophenyl)alanyl, D-3-(4-chlorophenyl)alanyl, L-3-(4-fluorophenyl)alanyl, D-3-(4-fluorophenyl)alanyl, L-3-(4-bromophenyl)alanyl, D-3-(4-bromophenyl)alanyl, L-3-(4-trifluoromethylphenyl)alanyl, D-3-(4-trifluoromethylphenyl)alanyl, L-3-(4-aminophenyl)alanyl, D-3-(4-aminophenyl)alanyl, L-3-(4-nitrophenyl)alanyl, D-3-(4-nitrophenyl)alanyl, L-3-(4-caynophenyl)alanyl, D-3-(4-cyanophenyl)alanyl, L-tyrosyl-(O-methyl), D-tyrosyl(O-methyl), L-3-(4-methylphenyl)alanyl, D-3-(4-methylphenyl)alanyl, L-3-(4-nitrophenyl)alanyl, D-3-(4-nitrophenyl)alanyl, L-3-(4-acetylaminophenyl)alanyl, D-3-(4-acetylaminophenyl)alanyl, L-methionyl, D-methionyl, L-alpha-methyl-3-(4-chlorophenyl)alanyl, D-alpha-methyl-3-(4-chlorophenyl)alanyl, (3S)-1,2,3,4-tetrahydroisoquinoline-3-carbonyl, (3R)-1,2,3,4-tetrahydroisoquinoline-3-carbonyl, (2)-N-(ethylaminocarbonyl)-(5)-N-(ethylamido)glutamyl, alpha-aza-3-(3,4,5-trimethylphenyl)alanyl, alpha-aza-3-(4-bromophenyl)alanyl, alpha-aza-3-(4-methylphenyl)alanyl, alpha-aza-3-(1-naphthyl)alanyl, alpha-aza-3-(1-adamantyl)alanyl, L-3-(3-quinolyl)-alanyl, D-3-(3-quinolyl)-alanyl, alpha-aza-3-(4-chlorophenyl)alanyl, alpha-aza-3-(4-fluorophenyl)alanyl, alpha-aza-3-(2-naphthyl)alanyl, alpha-aza-3-(3-quinolyl)alanyl, alpha-aza-phenylalanyl, alpha-aza-tyrosyl(O-methyl), alpha-aza-3-(2-thienyl)alanyl, alpha-aza-3-(3-benzthienyl)alanyl, alph-aza-cyclohexylalanyl, alpha-aza-tryptyl, alpha-aza-tryptyl(N-indole-methyl), alpha-aza-tryptyl(N-indole-formyl), N-($R_{31}$)-L-phenylalanyl, N-($R_{31}$)-D-phenylalanyl, N-($R_{31}$) D-3-(4-chlorophenyl)alanyl, N-($R_{31}$)-L-3-(4-chlorophenyl)alanyl, N-($R_{31}$)-D-3-(4-fluorophenyl)alanyl, N-($R_{31}$)-L-3-(4-fluorophenyl)alanyl, N-($R_{31}$)-L-3-(4-trifluoromethylphenyl)alanyl, N-($R_{31}$)-D-3-(4-trifluoromethylphenyl)alanyl, N-($R_{31}$)-L-3-(cyclohexyl)alanyl, N-($R_{31}$)-D-3-(cyclohexyl)alanyl, N-($R_{31}$)-L-3-(4-bromophenyl)alanyl, N-($R_{31}$)-D-3-(4-bromophenyl)alanyl, N-($R_{31}$)-L-3-(4-nitrophenyl)alanyl, N-($R_{31}$)-D-3-(4-nitrophenyl)alanyl, L-prolyl, D-prolyl, N-($R_{31}$)-L-O-methyltyrosyl, N-($R_{31}$)-L-tyrosyl, N-($R_{31}$)-D-O-methyl-tyrosyl, N-($R_{31}$)-D-tyrosyl, N-($R_{31}$)-L-histidyl, N-($R_{31}$)-D-histidyl, N-($R_{31}$)-L-3-(2-thienyl)alanyl, N-($R_{31}$)-D-3-(2-thienyl)alanyl, N-($R_{31}$)-L-3-(2-thiazolyl)alanyl, N-($R_{31}$)-D-3-(2-thiazolyl)alanyl, N-($R_{31}$)-L-3-(2-pyridyl)alanyl, N-($R_{31}$)-D-3-(2-pyridyl)alanyl, N-($R_{31}$)-D-3-(2-naphthyl)alanyl, N-($R_{31}$)-L-3-(2-naphthyl)alanyl, N-($R_{31}$)-L-3-(3-benzthienyl)alanyl, N-($R_{31}$)-D-3-(3-benzthienyl)alanyl, N-($R_{31}$)-L-3-(2-benzthienyl)alanyl, N-($R_{31}$)-D-3-(2-benzthienyl)alanyl, N-($R_{31}$)-L-3-(3-bezoxazolyl)alanyl, N-($R_{31}$)-D-3-(3-benzoxazolyl)alanyl, N-($R_{31}$)-L-3-(3-pyridyl)alanyl, N-($R_{31}$)-D-3-(3-pyridyl)alanyl, N-($R_{31}$)-L-tryptyl, N-($R_{31}$)-D-tryptyl, N-($R_{31}$)-L-tryptyl(N-indole-methyl), N-($R_{31}$)-D-tryptyl(N-indole-methyl), N-($R_{31}$)-D-methionyl, N-($R_{31}$)-L-methionyl, N-($R_{31}$)-D-3-(1-naphthyl)alanyl, and N-($R_{31}$)-L-3-(1-naphthyl)alanyl, wherein $R_{31}$ is methyl, ethyl, propyl or isopropyl;

C is an amino acyl residue selected from the group consisting of L-tryptyl, D-tryptyl, L-tryptyl(N-indole-formyl), D-tryptyl(N-indole-formyl), L-tryptyl(N-indole-methyl), D-tryptyl(N-indole-methyl), 5-fluoro-L-tryptyl, 5-fluoro-D-tryptyl, L-phenylalanyl, L-prolyl, D-prolyl, L-tyrosyl, D-tyrosyl, D-phenylalanyl, D-3-3-pyridyl)alanyl, L-3-(3-pyridyl)alanyl, D-3-(3-pyridyl-N'-oxide)alanyl, L-3-(3-pyridyl-N'-oxide)alanyl, D-3-(3-quinolyl)alanyl, L-3-(3-quinolyl)alanyl, D-3-(3-quinolyl-N'-oxide)alanyl, L-3-(3-quinolyl-N'-oxide)alanyl, D-3-(1-adamantyl)alanyl, L-3-(1-adamantyl)alanyl, L-3-(1-naphthyl)alanyl, D-3-(1-naphthyl)alanyl, L-3-(3-benzthienyl)alanyl, D-3-(3-benzthienyl)alanyl, L-3-(2-benzthienyl)alanyl, D-3-(2-benzthienyl)alanyl, L-3-(3-benzoxazolyl)alanyl, D-3-(3-benzoxazolyl)alanyl, L-cyclohexylalanyl, D-cyclohexylalanyl, L-3-(3-indazolyl)alanyl, D-3-(3-indazolyl)alanyl, alpha-methyl-L-phenylalanyl, alpha-methyl-D-phenylalanyl, L-3-2-naphthylalanyl, D-3-2-naphthylalanyl, L-O-methyltyrosyl, D-O-methyltyrosyl, L-3-(4-methylphenyl)alanyl, D-3-(4-methylphenyl)alanyl, L-3-(pentamethylphenyl)alanyl, D-3-(pentamethylphenyl)alanyl, L-3-(3,4,5-trimethylphenyl)alanyl, D-3-(3,4,5-trimethylphenyl)alanyl, L-3-(4-chlorophenyl)alanyl, D-3-(4-chlorophenyl)alanyl, alpha-methyl-L-3-(4-chlorophenyl)alanyl, alpha-methyl-D-3-4-chlorophenyl)alanyl, L-3-(4-trifluoromethylphenyl)alanyl, D-3-(4-trifluoromethylphenyl)alanyl, L-3-(4-fluorophenyl)alanyl, D-3-(4-fluorophenyl)alanyl, L-3-(2-thienyl)-alanyl, D-3-(2-thienyl)-alanyl, N-($R_{32}$)-L-3-(3-pyridyl)alanyl, N-($R_{32}$)-D-3-(3-pyridyl)alanyl, N-($R_{32}$)-L-3-(3-pyridyl-N'-oxide)alanyl, N-($R_{32}$)-D-3-(3-pyridyl-N'-oxide)alanyl, L-3-(2-thiazolyl)-alanyl, D-3-(2-thiazolyl)alanyl, alpha-aza-3-(1-naphthyl)alanyl, alpha-aza-tryptyl, alpha-aza-phenylalanyl, alpha-aza-3-(2-thienyl)alanyl, alpha-aza-3-4-methylphenyl)alanyl, alpha-aza-3-(pentamethylphenyl)alanyl, alpha-aza-3-(2-naphthyl)alanyl, alpha-aza-3-(3-benzthienyl)alanyl, alpha-aza-3-(3-benzoxazolyl)alanyl, alpha-aza-3-(cyclohexyl)alanyl, alpha-aza-3-(1-adamantyl)alanyl, alpha-aza-3-(4-methoxyphenyl)alanyl, alpha-aza-3-(4-chlorophenyl)alanyl, alpha-aza-3-(4 bromophenyl)alanyl, alpha-aza-tryptyl(N-indole-methyl), alpha-aza-3-3-pyridyl)alanyl, alpha-aza-3-(3-guinolyl)alanyl, alpha-aza-3-(2-thiazolyl)alanyl, N-($R_{32}$)-L-3-(2-thienyl)alanyl, N-($R_{32}$)-D-3-(2-thienyl)alanyl, L-3-(3-quinolyl)alanyl, D-3-(3-quinolyl)alanyl, L-3-(2-naphthyl)alanyl, D-3-(2-naphthyl)alanyl, N-($R_{32}$)-D-phenylalanyl, N-($R_{32}$)-L-phenylalanyl, N-($R_{32}$)-D-tryptyl, N-($R_{32}$)-L-tryptyl, N-($R_{32}$)-L-tryptyl(N-indole-formyl), N-($R_{32}$)-D-tryptyl(N-indole-formyl), N-($R_{32}$)-L-tryptyl(N-indole-methyl), N-($R_{32}$)-D-tryptyl(N-indole-methyl), N-($R_{32}$)-L-3-(2-thiazolyl)alanyl, N-($R_{32}$)-D-3-(2-thiazolyl)alanyl, N-($R_{32}$)-L-3-(3-pyridyl)alanyl, N-($R_{32}$)-D-3-(3-pyridyl)alanyl, N-($R_{32}$)-D-3-(3-quinolyl)alanyl, N-($R_{32}$)-L-3-(3-quinolyl)alanyl, N-($R_{32}$)-D-3-(1-adamantyl)alanyl, N-($R_{32}$)-L-3-(1-adamantyl)alanyl, N-($R_{32}$)-D-3-(4-fluorophenyl)alanyl, N-($R_{32}$)-L-3-(4-fluorophenyl)alanyl, N-($R_{32}$)-D-3-(4-chlorophenyl)alanyl, N-($R_{32}$)-L-3-(4-chlorophenyl)alanyl, N-($R_{32}$)-L-3-(4-trifluoromethylphenyl)alanyl, N-($R_{32}$)-D-3-(4-trifluoromethylphenyl)alanyl, N-($R_{32}$)-D-3-(2-naphthyl)alanyl, N-($R_{32}$)-L-3-(2-naphthyl)alanyl, N-($R_{32}$)-D-3-(1-naphthyl)alanyl, N-($R_{32}$)-L-3-(1-naphthyl)alanyl, N-($R_{32}$)-L-3-(3-benzthienyl)alanyl, N-($R_{32}$)-D-3-(3-benzthienyl)alanyl, N-($R_{32}$)-L-3-(2-benzthienyl)alanyl, N-($R_{32}$)-D-3-(2-benzthienyl)alanyl, N-($R_{32}$)-L-3-(3-benzoxazolyl)alanyl, N-($R_{32}$)-D-3-(3-benzoxazolyl)alanyl, N-($R_{32}$)-L-tyrosyl, N-($R_{32}$)-D-tyrosyl, N-($R_{32}$)-L-3-(3,4,5-trimethylphenyl)alanyl, N-($R_{32}$)-D-3-(3,4,5-trimethylphenyl)alanyl, N-($R_{32}$)-L-3-(4-methylphenyl)alanyl, N-($R_{32}$)-D-3-(4-methylphenyl)alanyl, N-($R_{32}$)-L-3-(pentamethylphenyl)alanyl, N-($R_{32}$)-D-3-(pentamethylphenyl)alanyl, N-($R_{32}$)-L-3-(4-bromophenyl)alanyl, N-($R_{32}$)-D-3-(4-bromophenyl)alanyl, N-($R_{32}$)-L-cyclohexylalanyl, N-($R_{32}$)-D-cyclohexylalanyl, N-($R_{32}$)-L-3-(3-indazolyl)alanyl, N-($R_{32}$)-D-3-(3-indazolyl)alanyl, N-alpha-($R_{32}$)-alpha-aza-3-(1-naphthyl)alanyl, N-alpha-($R_{32}$)-alpha-aza-3-(3-pyridyl)alanyl, N-alpha-($R_{32}$)-alpha-aza-phenylalanyl, N-alpha-($R_{32}$)-alpha-aza-3-(3-benzthienyl)alanyl, N-alpha-($R_{32}$)-alpha-aza-3-(2-benzthienyl)alanyl, N-alpha-($R_{32}$)-alpha-aza-3-(4-methylphenyl)alanyl, N-alpha-($R_{32}$)-alpha-aza-3-(4-methylphenyl)alanyl, N-alpha-($R_{32}$)-alpha-aza-3-(4-chlorophenyl)alanyl, N-($R_{32}$)-O-methyl-D-tyrosyl and N-($R_{32}$)-O-methyl-L-tyrosyl, wherein $R_{32}$ is methyl, ethyl, propyl or isopropyl;

D is an amino acyl residue selected from the group consisting of prolyl, 4-hydroxyproline, L-seryl, L-seryl(O-benzyl), L-seryl(O-$PO_3H_2$), L-serly(O-$PO_3Me_2$, L-glutamine, L-alpha,beta-diaminopropyl, L-alanyl, L-threonyl, 2,3-diaminopropionyl, 2-amino3-quanidinopropionyl, 2,3-diaminopropionyl (wherein the 3-amino group is substituted with loweralkyl, 3-pyridinecarbonyl, 2-pyrazinecarbonyl or 2-indolecarbonyl), N-alpha-aza-glycyl, N-alpha-aza-alanyl, N-alpha-($R_o$)-alpha-aza-glycyl, N-alpha ($R_o$)-alpha-aza-alanyl, N-($R_0$)-L-seryl, N-($R_0$) L-seryl(O-benzyl), N ($R_0$)-L-glutamine, N-($R_0$)-L-alanyl, N-alpha-($R_o$)-beta-aminopropyl, N-alpha-($R_o$)-N-beta-ethylaminopropyl, N-($R_o$)-L-seryl(O-$PO_3H_2$), N-($R_o$)-L-seryl(O-$PO_3Me_2$) and N-($R_0$)-L-threonyl, wherein $R_0$ is loweralkyl or allyl;

or D is a glycosyl derivative of serine or threonine;

E is an amino acyl residue selected from the group consisting of L-tyrosyl, L-tyrosyl(O-methyl), L-tyrosyl(O-ethyl), L-tyrosyl(O-$PO_3H_2$), L-tyrosyl(O-$PO_3Me_2$), L-phenylalanyl, N-($R_{33}$)-L-tyrosyl, N-($R_{33}$)-L-tyrosyl(O-methyl), N-($R_{33}$)-L-tyrosyl(O-$PO_3H_2$), N-($R_{33}$)-L-tyrosyl(O-$PO_3Me_2$), 3-(2-thienyl)alanyl, 3-(3-benzthienyl)alanyl, 3-1-naphthyl)alanyl, 3-(2-naphthyl)alanyl, N-($R_{33}$)-L-phenylalanyl, L-3-(4-chlorophenyl)alanyl, L-3-(4-fluorophenyl)alanyl, L-histidyl, L-3-(cyclohexyl)alanyl, L-3-(4-aminophenyl)alanyl, 1-3-(4 acetylaminophenyl)alanyl, N-($R_{33}$)-L-3-(4-aminophenyl)alanyl, N-($R_{33}$)-L-3-(4-acetylaminophenyl)alanyl, N-($R_{33}$)-L-3-(4-fluorophenyl)alanyl, N-($R_{33}$)-L-3-(4-chlorophenyl)alanyl, N-($R_{33}$)-L-histidyl, N-($R_{33}$)-L-3-(cyclohexyl)alanyl, N-($R_{33}$)-3-(2-thienyl)alanyl, N-($R_{33}$)-3-(3-benzthienyl)alanyl, N-($R_{33}$)-3-(1-naphthyl)alanyl, N-($R_{33}$)-3-(2-naphthyl)alanyl, and N-($R_{33}$)-L-tyrosyl(O-ethyl), wherein $R_{33}$ is methyl, ethyl, propyl or isopropyl; or E is

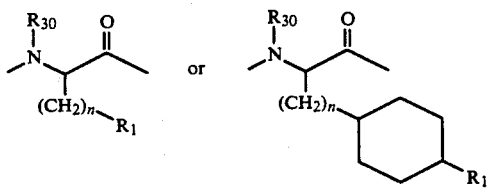

wherein n is 1 to 4; $R_{30}$ is hydrogen, methyl, ethyl, propyl or isopropyl; and $R_1$ is amino, alkylamino, cycloalkylamino or alkanoylamino; or $R_1$ is —N($R_3$)-C(O)($CH_2$)$_{ff}R_{60}$ or -NHC(NH($R_3$))=$NR_4$ wherein $R_3$ is hydrogen, loweralkyl or cycloalkyl; $R_4$ is hydrogen, loweralkyl, cycloalkyl, amino or cyano; ff is 0 to 6; and $R_{60}$ is loweralkyl, dialkylamino, cycloalkyl, aryl, arylalkyl, heterocyclic, (heterocyclic)alkyl or —NHR$_{120}$ wherein R$_{120}$ is hydrogen, loweralkyl, cycloalkyl, aryl, arylalkyl, heterocyclic, (heterocyclic)alkyl, amino, alkanoylamino or —NHR$_{62}$ wherein R$_{62}$ is loweralkyl, cycloalkyl, aryl, arylalkyl, heterocyclic, (heterocyclic)alkyl or —C(O)R$_{63}$ wherein R$_{63}$ is loweralkyl, cycloalkyl, aryl, arylalkyl, heterocyclic or (heterocyclic)alkyl;

or $R_1$ is -C(O)R wherein R is hydroxy, alkoxy, amino, phenoxy or -methoxyphenyl;

F is a D-amino acyl residue derived from any of the naturally occuring alpha amino acids or from synthetic, non-natural alpha amino acids including, but not limited to, a D-amino acyl residue of the formula:

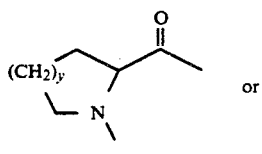 or 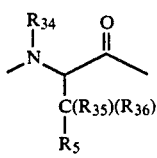 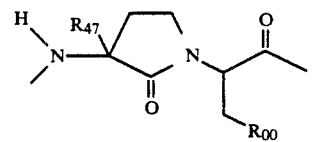

wherein y is 1 to 3; $R_5$ is $C_1$ to $C_6$ straight or branched chain alkyl, $C_3$ to $C_7$ cycloalkyl, hydroxy, alkoxy, thioalkoxy, aryl or a heterocyclic aromatic ring; or $R_5$ is —$(CH_2)_m R_6$ or

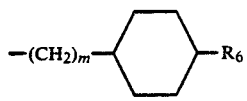

wherein m is 0 to 4 and $R_6$ is amino, alkylamino, cycloalkylamino or alkanoylamino; or $R_6$ is —NH—C(NH(R'))=NR" or —N(R')C(O)(CH_2)_{gg}R_{65}$ wherein R' is hydrogen, loweralkyl or cycloalkyl; R' is hydrogen, loweralkyl, cycloalkyl, amino or cyano; gg is 0 to 6; and $R_{65}$ is loweralkyl, dialkylamino, cycloalkyl, aryl, arylalkyl, heterocyclic, (heterocyclic)alkyl or —$NHR_{66}$ wherein $R_{66}$ is hydrogen, loweralkyl, cycloalkyl, aryl, arylalkyl, heterocyclic, (heterocyclic)alkyl, amino, alkanoylamino or —$NHR_{67}$ wherein $R_{67}$ is hydrogen, loweralkyl, cycloalkyl, aryl, arylalkyl, heterocyclic, (heterocyclic)alkyl or —$C(O)R_{68}$ wherein $R_{68}$ is loweralkyl, cycloalkyl, aryl, arylalkyl, heterocyclic or (heterocyclic)alkyl;

$R_{34}$ is hydrogen, methyl, ethyl, propyl or isopropyl; and $R_{35}$ and $R_{36}$ are independently selected from hydrogen and loweralkyl;

or F is a D-aminoacyl residue having the formula:

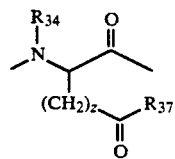

wherein z is 0 to 3 and $R_{37}$ is hydroxy, alkoxy, phenoxy, amino or p-methoxyphenyl and $R_{34}$ is hydrogen, methyl, ethyl, propyl or isopropyl;

or F is a glycosyl derivative of D-serine or D-threonine;

G is an amino acyl residue selected from the group consisting of L-leucyl, L-isoleucyl, N-($R_{38}$)-isoleucyl, norleucyl, N-($R_{38}$)-norleucyl, L-N-($R_{38}$)leucyl, alloisoleucyl, valyl, norvalyl, seryl(O-t-Bu), tyrosyl, tryptyl, 2-aminobutyryl, L-(cyclohexyl)alanyl, L-N-($R_{38}$)-cyclohexylalanyl, N-($R_{38}$)-valyl, phenylalanyl, N-($R_{38}$)-phenylalanyl, N-($R_{38}$)-tryptyl, N-($R_{38}$)-tyrosyl, seryl(O-PO_3H_2), seryl(O-PO_3Me_2), N-($R_{38}$)-seryl(O-PO_3H_2), N-($R_{38}$)-seryl(O-PO_3Me_2), prolyl, pipecolyl, seryl and N-($R_{38}$)-seryl, wherein $R_{38}$ is methyl, ethyl, propyl or isopropyl;

or G is a glycosyl derivative of serine or threonine;
or F and G taken together are

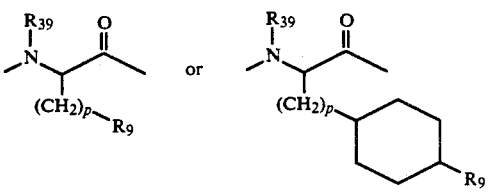

wherein $R_{47}$ is hydrogen, loweralkyl, 3-indolylmethyl, 2-naphthylmethyl, benzyl or substituted benzyl wherein the phenyl ring is substituted with a substituent selected from halogen, hydroxy and methoxy and $R_{oo}$ is loweralkyl;

H is an amino acyl residue of the formula:

wherein p is 1 to 4; $R_{39}$ is hydrogen, methyl, ethyl, propyl or isopropyl; and $R_9$ is amino, alkylamino, cycloalkylamino or alkanoylamino; or $R_9$ is —$N(R_{11})$-$C(O)(CH_2)_{hh}R_{70}$ or —$NH$-$C(NH(R_{11}))$=$NR_{12}$ wherein $R_{11}$ is hydrogen, loweralkyl or cycloalkyl; $R_{12}$ is hydrogen, loweralkyl, cycloalkyl, amino or cyano; hh is 0 to 6; and $R_{70}$ is loweralkyl, dialkylamino, cycloalkyl, aryl, arylalkyl, heterocyclic, (heterocyclic)alkyl or —$NHR_{71}$ wherein $R_{71}$ is hydrogen, loweralkyl, cycloalkyl, aryl, arylalkyl, heterocyclic, (heterocyclic)alkyl, amino, alkanoylamino or —$NHR_{72}$ wherein $R_{72}$ is hydrogen, loweralkyl, cycloalkyl, aryl, arylalkyl, heterocyclic, (heterocyclic)alkyl or —$C(O)R_{73}$ wherein $R_{73}$ is loweralkyl, cycloalkyl, aryl, arylalkyl, heterocyclic or (heterocyclic)alkyl;

or $R_9$ is $R^{*}C(O)$-wherein $R^{*}$ is hydroxy, alkoxy, amino, phenoxy or p-methoxyphenyl;

I is an imino acyl or aliphatic amino acyl residue selected from the group consisting of L-prolyl, L-pipecolyl, alpha-aza-prolyl, trans-beta-aminocyclopentanecarbonyl, cis-beta-aminocyclopentanecarbonyl, 3-(loweralkyl)-prolyl, N-methyl-L-alanyl, N-methylnorvalyl, 1-dihydroisoindole-2-L-carbonyl and thiazolidine-5-L-carbonyl; and J is 1-pyrrolidinyl, 1-piperidinyl, 4-morpholinyl, or an amino acyl residue selected from D-alanylamide, L-alanylamide, glycylamide, sarcosylamide, N-($R_{40}$)-D-alanylamide, N-($R_{40}$)-L-alanylamide, N-($R_{40}$)-beta-L-alanylamide, N-($R_{40}$)-beta-D-alanylamide, L-2-aminobutyrylamide, D-2-aminobutyrylamide, N-($R_{40}$)-L-2-aminobutyrylamide, N-($R_{40}$)-D-2-aminobutyrylamide, L-serylamide, D-serylamide, N-($R_{40}$)-L-serylamide, N-($R_{40}$)-D-serylamide, N-($R_{40}$)-L-norvalylamide, N-($R_{40}$)-D-norvalylamide, L-norvalylamide, D-norvalylamide or alpha-aza-alanylamide, wherein $R_{40}$ is methyl, ethyl, propyl or isopropyl; or J is —$NHR_8$ or —$NHCH_2CONHR_8$ wherein $R_8$ is hydrogen, loweralkyl, cycloalkyl, fluoro substituted loweralkyl or hydroxy substituted loweralkyl; or J is —$N(R_{132})N(R_{133})$-$C(O)$-$NH$-$R_{13}$ wherein $R_{13}$ is hydrogen, loweralkyl, cycloalkyl, hydroxy substituted loweralkyl or fluoro substituted loweralkyl and $R_{132}$ and $R_{133}$ are independently selected from hydrogen and loweralkyl; with the proviso that the amide bond between at least one of the pairs of residues A B, B-C, C-D, D-E, E-F, F-G, G-H, H-I, or I-J is alkylated on the nitrogen atom of the amide bond linking the two residues and with the proviso that the compound is not (pyro)Glu-His-Trp-Ser-Tyr-Gly-N-Me-Leu-Arg-Pro-Gly-NH$_2$, (pyro)Glu-His-Trp-Ser-Tyr-D-Trp-N-Me-Leu-Arg-Pro-Gly-NH$_2$, (pyro)Glu-His-Trp-Ser-Tyr-Gly-N-Me-Leu-Arg-Pro-NH$_2$, or (pyro)Glu-His-Trp-Ser-Tyr-D-Trp-N-Me-Leu-Arg-Pro-NH$_2$.

These compounds exhibit affinity for LHRH receptors. Generally, compounds of the invention which contain D-amino acids at positions 1, 2, 3 and 10 or at positions 1 and 2, or at positions 2 and 3, or which have position 2 deleted are LHRH antagonists.

As set forth above, and for convenience in describing this invention, the conventional abbreviations for the various common amino acids are used as generally accepted in the peptide art as recommended by the IUPAC-IUB Commission on Biochemical Nomenclature, *Biochemistry II*, 1726-1972). These represent L-amino acids, with the exception of the achiral amino acid glycine, and with the further exception of any unnatural or natural amino acids which are achiral, or are otherwise designated as D-. All peptide sequences mentioned herein are written according to the generally accepted convention whereby the N-terminal amino acid is on the left and the C-terminal amino acid is on the right.

Other abbreviations which are useful in describing the invention are the following:

| Amino acids, protecting groups, reagents | Abbreviation |
|---|---|
| 3-2-thienyl-D-alanyl | D-Thia |
| L-N-(epsilon)-isopropyllysyl | (isp)Lys |
| 2-(pyridyl)-L-alanyl | 2-Pal |
| Arginine | Arg |
| t-Butoxycarbonyl | Boc |
| Benzyl | Bzl |
| Benzyloxycarbonyl | Cbz |
| N,N'-Dicyclohexylcarbodiimide | DCC |
| Glycine | Gly |
| Histidine | His |
| 1-Hydroxybenzotriazole | HOBt |
| Isoleucine | Ileu |
| Leucine | Leu |
| Norleucine | Nleu |
| Norvaline | Nval |
| Methionine | Met |
| Methyl ester | OMe |
| Benzyl ester | OBzl |
| Phenylalanine | Phe |
| Proline | Pro |
| Pyroglutamic acid | (pyro)Glu |
| Serine | Ser |
| Tosyl | Tos |
| Tryptophan | Trp |
| Tyrosine | Tyr |
| N,N'-di-isopropylcarbodiimide | DIC |
| Dehydro-alanine | DeAla |
| L-N-methylserine | N—Me—Ser |
| (2)-N-methyl-3-N-ethyl-diamino-propionic acid | N—Me—N—Et—Dap |
| (2)-N-ethylureido-(5)-ethylamido-glutamic acid | EtuEtaGlu |
| L-N-acetylsarcosyl | N—Ac—Sar |
| L-N-formylsarcosyl | N-Form-Sar |
| 3-(pyridyl)-L-alanyl | 3-Pal |
| 3-(pyrazolyl)-L-alanyl | 3-Pyral |
| (3S)-1,2,3,4-tetrahydroioquinoline-3-carbonyl | 3-Tic |
| L-N-methyl-O-benzylseryl | N—Me—Ser(OBzl) |

-continued

| Amino acids, protecting groups, reagents | Abbreviation |
|---|---|
| L-O-methyltyrosyl | O—Me—Tyr |
| L-cyclohexylalanyl | Cha |
| 3-(2-naphthyl)-D-alanyl | D-(2)-Nal |
| 3-(1-naphthyl)-L-alanyl | (1)-Nal |
| 4-Dimethylaminopyridine | DMAP |
| Benzotriazol-1-yloxy-tris(dimethyl-amino)phosphonium hexafluorophosphate | BOP |
| Bis(2-oxo-3-oxazolidinyl)phosphine chloride | BOPCl |
| 3-(3-Benzthienyl)alanine | 3-Bal |
| 3-(3,4,5-trimethylphenyl)alanine | Tmp |
| D-3-(4-thiazolyl)alanine | D-4-Thiaz |
| homo-citrulline | HCit |
| D-Ser(O-alpha-L-Rhamnosyl) | D-Ser(O-alpha-L-Rha) |
| D-Lys(N-epsilon-4-methoxylbenzoyl) | D-Lys(Anis) |
| Lys(N-epsilon-carbonyl-N'-hydrazine) | Lys(N-epsilon-CO-Hyz) |
| D-Lys(N-epsilon-2-pyrazinecarbonyl) | D-Lys(N-epsilon-Pyrz) |
| Lys(N-epsilon-carbonyl-N'-hydrazine-N-acetyl | Lys(N-epsilon-CO-HyzAc) |
| D-Lys(N-epsilon-carbonyl-N'-morpholine) | D-Lys(N-epsilon-CO-Morph) |
| D-Lys(N-epsilon-carbonyl-N'-piperazin-yl-N''-methyl | D-Lys(N-epsilon-CONMePip) |
| D-3-(pentamethylphenyl)alanine | D-Pmp |
| D-4-(4-methoxybenzoyl)homoalanine | D-Mbha |
| Homoarginine(N,N'-guanidino-diEthyl) | Harg(N$^G$-diEt) |

The sequence of LHRH has been shown to be

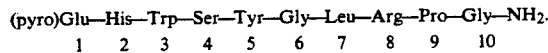

Nona- and decapeptides in which the amino acid residues at particular places in the sequence have been replaced by other amino acid residues or other moieties are abbreviated by showing the nature of the substitution, superscribed by the location, followed by LHRH as the parent. For example, the sequence

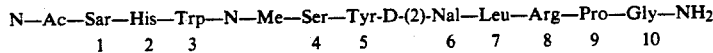

is represented [N-Ac-Sar$^1$-N-Me-Ser$^4$-D-(2)-Nal$^6$]LHRH; and the sequence (pyro)Glu-His-Trp-N-Me-Ser-Tyr-D-Trp$^6$-Leu-Arg-Pro-NHEt is represented [N-Me-Ser$^4$-D-Trp$^6$-Pro$^9$-NHEt]LHRH.

As used herein, the term "pharmaceutically acceptable salts" refers to salts that retain the desired biological activity of the parent compound and do not impart any undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, trifluoroacetic acid, oxalic acid, tartaric acid, succinic acid, maleic acid, fumaric acid, gluconic acid, citric acid, malic acid, ascorbic acid, benzoic acid, tannic acid, pamoic acid, alginic acid, polyglutamic acid, methanesulfonic acid, p-toluenesulfonic acid, naphthalenesulfonic acids, naphthalenedisulfonic acids, polygalacturonic acid; (b) salts with polyvalent metal cations such as zinc, calcium, bismuth, barium, magnesium, aluminum, copper, cobalt, nickel, cadmium, and the like; or with an organic cation formed from N,N'-dibenzylethylene-diamine or ethylenediamine; or (c) combinations, of (a) and (b), e.g., a zinc tannate salt and the like.

The term "loweralkyl" refers to a straight or branched chain saturated hydrocarbon group having from 1 to 6 carbon atoms such as, for example, methyl, ethyl, n-propyl, isopropyl, n-butyl, isobutyl, sec-butyl, tert-butyl, n-pentyl and n-hexyl.

The term "alkyl of 1 to 12 carbon atoms" refers to a straight or branched chain radical of 1 to 12 carbon atoms.

The term "cycloalkyl" refers to a cyclic saturated hydrocarbon group having from 3 to 7 carbon atoms, for example, cyclopropyl, cyclobutyl, cyclopentyl, cyclohexyl and cycloheptyl.

The term "alkoxy" refers to $-OR_{41}$ wherein $R_{41}$ is loweralkyl including, but not limited to, methoxy, ethoxy, t-butyloxy and the like.

The term "thioalkoxy" refers to $-SR_{42}$ wherein $R_{42}$ is loweralkyl including, but not limited to, $-SCH_3$, $-SCH_2CH_3$ and the like.

The term "alkylamino" refers to $-NHR_{44}$ wherein $R_{44}$ is loweralkyl including, but not limited to, methylamino, ethylamino and the like.

The term "dialkylamino" refers to $-NR_{45}R_{46}$ wherein $R_{45}$ and $R_{46}$ are independently selected from loweralkyl including, but not limited to, dimethylamino, N-methyl-N-ethyl-amino and the like.

The term "cycloalkylamino" as used herein refers to $-NHR_{130}$ wherein $R_{130}$ is a cycloalkyl group.

The term "halogen" or "halo" as used herein refers to I, Br, Cl or F.

The term "alkanoyl" as used herein refers to $-C(O)R_{131}$ wherein $R_{131}$ is loweralkyl.

The term "alkanoylamino" as used herein refers to $R_{90}C(O)NH-$ wherein $R_{90}$ is loweralkyl.

The term "alkoxycarbonyl" as used herein refers to $R_{91}OC(O)-$ wherein $R_{91}$ is loweralkyl.

The term "aryl" as used herein refers to a monocyclic or bicyclic carbocyclic ring system comprising an aromatic carbocyclic ring. Aryl groups include, but are not limited to, phenyl, naphthyl, indanyl, indenyl, tetrahydronaphthyl and the like. Aryl groups can be unsubstituted or substituted with one, two or three substituents independently selected from halogen, loweralkyl, hydroxy, alkoxy, thioalkoxy, nitro, cyano, amino, alkylamino, dialkylamino, alkanoylamino, trihalomethyl and alkoxycarbonyl. Where a specific aryl group is mentioned as a substituent in a compound of this invention, it is to be understood that this invention is intended to encompass compounds comprising any aryl group in place of the specific aryl groups mentioned. In particular, where a specifically substituted phenyl group is mentioned as a substituent in a compound of this invention, it is to be understood that this invention is intended to encompass phenyl groups with other substituents selected from the list given above in place of the specific substituent(s) mentioned.

The term "arylalkyl" as used herein refers to an aryl group appended to a loweralkyl radical including, but limited to, benzyl, naphthylmethyl, 4-methoxybenzyl and the like.

The term "heterocyclic" or "heterocyclic group" as used herein refers to any 3-, 4-, 5- or 6-membered ring containing a heteroatom selected from oxygen, sulfur and nitrogen, or a 5- or 6-membered ring containing one, two or three nitrogen atoms; one nitrogen and one sulfur atom; or one nitrogen and one oxygen atom; wherein the nitrogen and sulfur heteroatoms can optionally be oxidized; wherein the nitrogen heteroatoms can optionally be quaternized; and wherein the 5-membered ring has 0-2 double bonds and the 6-membered ring has 0-3 double bonds. Heterocyclics also include any bicyclic group in which any of the above heterocyclic rings is fused to a benzene ring or another 5- or 6-membered heterocyclic ring independently defined as above. Heterocyclics include, but are not limited to, guinolyl, indolyl, benzofuryl, benzothienyl, imidazolyl, thiazolyl, benzoxazolyl, furyl, thienyl, pyridyl, pyrimidinyl, morpholinyl, piperazinyl, pyrrolidinyl, piperidinyl, thienyl, pyrazinyl, pyrazolyl, thiomorpholinyl, isoquinolyl, indazolyl and the like. Where a specific heterocyclic group is mentioned as a substituent in a compound of this invention, it is to be understood that this invention is intended to encompass compounds comprising any heterocyclic group in place of the specific heterocyclic group(s) mentioned.

Heterocyclics can be unsubstituted or substituted with substituents selected from hydroxy, halo, amino, alkylamino, dialkylamino, alkoxy, thioalkoxy, formyl, alkanoyl, alkanoylamino, benzyl, loweralkyl, cycloalkyl and trihaloalkyl.

The term "(heterocyclic)alkyl" as used herein refers to a heterocyclic group appended to a loweralkyl radical.

The term "glycosyl derivative of serine or threonine" as used herein refers to a serine or threonine residue which is bonded through its hydroxyl group (either alpha- or beta-glycosidically) to a glycosyl radical. Glycosyl radical are derived from a glycopyranose, glycofuranose or an oligosaccharide (all of which can be optionally protected). These glycosyl radicals are derived from D- or L-monosaccharides such as ribose, arabinose, xylose, lyxose, allose, altrose, glucose, mannose, gulose, idose, galactose, talose, erythrose, threose, psicose, fructose, sorbose, tagatose, xylulose, fucose, rhamnose, olivose, oliose, mycarose, rhodosamine, N-acetylglucosamine, N-acetylgalactosamine, N-acetylmannosamine; or disaccharides such as maltose, lactose, cellobiose, gentibiose, N-acetyllactosamine, chitobiose, beta-galactopyranosyl-(1,3)-N-acetylgalactosamine and beta-galactopyranosyl-(1,3)- or (1,4)-N-acetylglucosamine, as well as their synthetic derivatives, such as 2-deoxy, 2-amino, 2-acetamideo- or 2-halogeno derivatives.

Protecting groups for glycosyl radicals include those commonly used in carbohydrate chemistry including, but not limited to, $C_1$ to $C_{10}$ acyl groups (such as acetyl, benzoyl, trichloroacetyl and the like) and various ethers and acetals such as methyl ethers, methoxymethyl ethers, benzyl ethers, tetrahydropyranyl ethers, benzylidene acetals, isopropylidene acetals and trityl ethers.

Compounds of the invention include:
[N-Me-Ser$^4$-D-Trp$^6$-Pro$^9$NHEt]LHRH;
[N-Me-Ser-$^4$-D-Leu$^6$-Pro$^9$NHEt]LHRH;
[N-Me-Ser$^4$-D-2 Nal$^6$]LHRH;
[M-Me-Ser$^4$-D-Trp$^6$-N-Me-Leu$^7$-Pro$^9$NHEt]LHRH;
[N-Me-Ser$^4$-D-Trp$^6$-N-Me-Leu$^7$-Pro$^9$-AzaGly-10]LHRH;
[N-Me-Ser$^4$-D-O-t-butyl-Ser$^6$-Pro$^9$NHEt]LHRH;
[N-Me-Ser$^4$-D-Arg$^6$-Pro$^9$NHEt]LHRH;
[N-Me-Ser$^4$-D-Lys$^6$-(N-epsilon-isp) Pro$^9$NHEt]LHRH;
[N-Ac-Sar$^1$-N-Me-Ser$^4$-D-Trp$^6$-Pro$^9$NHEt]LHRH;
[N-Ac-Sar$^1$-N-Me-Ser$^4$-D-2-Nal$^6$]LHRH;
[N-Ac-Sar$^1$-Phe$^2$-N-Me-Ser$^4$-D-Trp$^6$-Pro$^9$NHEt]LHRH;
[Phe$^2$-N-Me-Ser$^4$-D-Trp$^6$-Pro$^9$NHEt]LHRH;

[Phe²-N-Me-Ser⁴-D-2-Nal⁶]LHRH;
[Phe²-N-Me-Ser⁴-D-Arg⁶-Pro⁹NHEt]LHRH;
[D-4-Cl-Phe¹,²-D-Trp³-N-Me-Ser⁴-D-Arg⁶-D-Ala¹⁰]LHRH;
[N-Ac-Sar¹-(2)-N-Me-(3)-N-Et-Dap⁴-D-Trp⁶-Pro⁹NHEt]LHRH;
[(2)-N-Me-(3)-N-Et-Dap⁴-D-(2)-Nal⁶]LHRH;
[(2)-N-Me-(3)-N-Et-Dap⁴-D-Trp⁶-Pro⁹NHEt]LHRH;
[(2)-N-Me-(3)-N-Et-Dap⁴-D-Arg⁶-Pro⁹NHEt]LHRH;
[(2)-N-Me-(3)-N-Et-Dap⁴-D-Leu⁶-Pro⁹NHEt]LHRH;
[(2)-N-Me-(3)-N-Et-Dap⁴-D-O-t-butyl-Ser⁶-Pro⁹NHEt]LHRH;
[(2)-N-Me-(3)-N-Et-Dap⁴-D-Trp⁶-N-Me-Leu⁷-Pro⁹NHEt]LHRH;
[(2)-N-(Ethylaminocarbonyl)-(5)-N-Ethylamido-Glu¹-N-Me-Ser⁴-D-2-Nal]LHRH;
[N-Me-Ser⁴-[2-(S -3-amino-2-oxo-pyrrolidin-1-yl)-S-2-isopropylmethylacetyl]⁶,⁷-Pro⁹NHEt]LHRH;
[N-Ac-Sar¹-N-Me-Ser⁴-[2-(S-3-amino-2-oxo-pyrrolidin-1-yl)-S-isopropylmethylacetyl]⁶,⁷-Pro⁹NHEt]LHRH;
[Phe²-N-Me-Ser⁴-[2-(S-3-amino-2-oxo-pyrrolidin-1-yl) S2-isopropylmethylacetyl]⁶,⁷-Pro⁹NHEt]LHRH;
[N-Ac-D-4-Cl-Phel-D-4-Cl-Phe²-D-Trp³,⁶-N-Me-Ser⁴-D-Ala¹⁰]LHRH;
[N-Ac-Pro¹-D-Cl-Phe²-D-Trp³-N-Me-Ser⁴-D-Arg⁶-D-Ala¹⁰]LHRH:
[N-Me-Phe²-D-2-Nal⁶-Pro⁹NHEt]LHRH;
[N-Me-Tyr⁵-D-Trp⁶-Pro⁹NHEt]LHRH;
N-Me-Trp³-D-Trp⁶-Pro⁹NHEt]LHRH;
N-Me-1-Nal³-D-Tyr⁶-Pro⁹NHEt]LHRH;
N-Me-D-2-Nal⁶-Pro⁹NHEt]LHRH;
D-Trp⁶-N-Me-Arg⁸-Pro⁹NHEt]LHRH
D-Trp⁶-Sar¹⁰]LHRH;
[N-Ac-Sar¹-D-Phe²,⁶-D-1-Nal³-N-Me-Tyr⁵-D-Ala¹⁰]LHRH;
[N-Ac-3,4-dehydro-Pro¹-4-Cl-D-Phe²-D-Trp³,⁶-N-Me-Tyr⁵-D-Ala¹⁰]LHRH;
[N-Ac-D-4-Cl-Phe¹,²-D-Bal³-N-Me-Tyr⁵-D-Lys⁶-D-Ala¹⁰]LHRH;
[N-Me-Phe²-N-Me-Tyr⁵-D-Trp⁶-Pro⁹NHEt]LHRH;
[N-Ac-3,4-dehydro-Pro¹-4-Cl-D-Phe²-D-Trp³-N-Me-Tyr⁵-D-Arg⁶-N-Me-Leu⁷-D-Ala¹⁰]LHRH;
[N-Ac-D-2-Nal¹-4-Cl-D-Phe²-D-3-Pal³-N-Me-Ser⁴-Lys⁵-(N-epsilon-nicotinyl)-D-Lys⁶-(N-epsilon-nicotinyl)-Lys⁸-(N-epsilon-isopropyl)-D-Ala¹⁰]LHRH;
[N-Ac-D-2-Nal¹-4-Cl-D-Phe²-D-3-Pal³-N-Me-Tyr⁵-D-Lys⁶-(N-epsilon-nicotinyl)-Lys⁸(N-epsilon-isopropyl)-D-Ala¹⁰]LHRH;
[N-Ac-D-2-Nal¹-4-Cl-D-Phe²-D-3-Pal-N-Me-Ser⁴-Lys⁵-(N-epsilon-nicotinyl)-D-Lys⁶-(N-epsilon-2-carbonylpyrazinyl)-Lys⁸(N-epsilon-isopropyl)-D-Ala¹⁰]LHRH;
[N-Me-Tyr⁵-D-Ser⁶(O-t-butyl)-Pro⁹NHEt]LHRH;
[N-Me-Tyr⁵-D-Leu⁶-Pro⁹NHEt]LHRH;
[N-Me-Tyr⁵-D-2-Nal⁶]LHRH;
[N-Me-D-Trp⁶-Pro⁹NHEt]LHRH;
[N-Me-D-2-Nal⁶]LHRH;
[N-Me-Tyr⁵-N-Me-D-Ser⁶(O-t-butyl)-Pro⁹NHEt]LHRH;
[N-Me-Phe²-D-2-Nal⁶]LHRH;
[N-Me-Phe²-N-Me-Tyr⁵-D-Leu⁶-Pro⁹NHEt]LHRH;
[N-Me-Phe²-N-Me-Tyr⁵-D-Ser⁶(O-t-butyl)-Pro⁹NHEt]LHRH;
[N-Me-Tyr⁵-D-His⁶(N-im-Bzl)-Pro⁹NHEt]LHRH;
[N-Ac-D-4-Cl-Phe¹,²-D-2-Thia³-N-Me-Ser⁴-D-Lys⁶-D-Ala¹⁰]LHRH;
[N-Ac-D-4-Cl-Phe¹,²-D-2-Thia³-N-Me-Tyr⁵-D-Lys⁶-D-Ala¹⁰]LHRH;
[N-Ac-D-2-Nal¹-D-4-Cl-Phe²,³-N-Me-Ser⁴-N-Me-Tyr⁵-D-Lys⁶-D-Ala¹⁰]LHRH;
[N-Ac-D-4-Cl-Phe¹,²-D-2-Thia³-D-Lys⁶-N-Me-Arg⁸-D-Ala¹⁰]LHRH;
[N-Ac-D-4-Cl-Phe¹-N-Me-D-4-Cl-Phe²-D-2-Thia³-D-Lys⁶-D-Ala¹⁰]LHRH;
[N-Ac-D-2-Nal¹-N-Me-D-4-Cl-Phe²-D-3-Pal³-Lys⁵(N-epsilon-nicotinyl)-D-Lys⁶(N-epsilon-nicotinyl)-Lys⁸(N-epsilon-isopropyl)-D-Ala¹⁰]LHRH;
[N-Ac-D-2-Nal¹-D-4-Cl-Phe²-D-3-Pal³,⁶-N-Me-Tyr⁵-Lys⁸(N-epsilon-isopropyl)-D-Ala¹⁰]LHRH;
[N-Ac-D-2-Nal¹-D-4-Cl-Phe²-D-3-Pal³-N-Me-Tyr⁵-D-Lys⁶(N-epsilon-carbonyl-N'-morpholino)-Lys⁸(N-epsilon-isopropyl)-D-Ala¹⁰]LHRH;
[N-Ac-D-2-Nal¹-D-4-Cl-Phe²-D-3-Pal³-N-Me-Tyr⁵-D-Lys⁶(N-epsilon-carbonyl-N'-piperazinyl-N''-methyl)-Lys⁸(N-epsilon-isopropyl)-D-Ala¹⁰]LHRH;
[N-Ac-D-2-Nal¹-D-4-Cl-Phe²-D-3-Pal³-N-Me-Tyr⁵-D-Lys⁶(N-epsilon-nicotinyl)-Lys⁸(N-epsilon-cyclohexyl)-D-Ala¹⁰]LHRH;
[N-Ac-D-2-Nal¹-D-4-Cl-Phe²-D-4-Thiaz³-N-Me-Tyr⁵-D-Lys⁶(N-epsilon-nicotinyl)-Lys⁸(N-epsilon-isopropyl)-D-Ala¹⁰]LHRH;
[N-Ac-D-2-Nal¹-D-4-Cl-Phe²-D-3-Pal³-N-Me-Tyr⁵-D-Lys⁶(N-epsilon-nicotinyl)-N-Me-Leu⁷-Lys⁸(N-epsilon-isopropyl)-D-Ala¹⁰]LHRH;
[N-Ac-D-2-Nal¹-D-4-Cl-Phe²-D-3-Pal³-N-Me-Tyr⁵-D-Lys⁶(N-epsilon-nicotinyl)-Cha⁷-Lys⁸(N-epsilon-isopropyl)-D-Ala¹⁰]LHRH;
[N-Ac-D-2-Nal¹-D-4-Cl-Phe²-D-3-Pal³-N-Me-Tyr⁵-D-Lys⁶(N-epsilon-nicotinyl)-Lys⁸(N-epsilon-isopropyl)-Sar¹⁰]LHRH;
[N-Ac-D-2-Nal¹-D-4-Cl-Phe²-D-3-Pal³-N-Me-Tyr⁵-D-Lys⁶(N-epsilon-nicotinyl)-Cha⁷-D-Ala¹⁰]LHRH;
[N-Ac-Sar¹-D-4-Cl-Phe2-D-1-Nal³-N-Me-Tyr⁵-D-Lys⁶(N-epsilon-nicotinyl)-Lys⁸(N-epsilon-isopropyl)-D-Ala¹⁰]LHRH;
[N-Ac-Sar¹-D-4-Cl-Phe²-D-3-Bal³-N-Me-Tyr⁵-D-Lys⁶(N-epsilon-nicotinyl)-Lys⁸(N-epsilon-isopropyl)-D-Ala¹⁰]LHRH;
[N-Ac-aza-Gly¹-D-4-Cl-Phe²-D-1-Nal³-N-Me-Tyr⁵-D-Lys⁶(N-epsilon-nicotinyl)-Lys⁸(N-epsilon-isopropyl)-D-Ala¹⁰]LHRH;
[N-Ac-aza-Gly¹-D-4-Cl-Phe²-D-3-Bal³-N-Me-Tyr⁵-D-Lys⁶(N-epsilon-nicotinyl)-Lys⁸(N-epsilon-isopropyl)-D-Ala¹⁰]LHRH;
[N-Ac-Sar¹-D4-Cl-Phe²-D-¹-Nal³-N-Me-Tyr⁵-D-Lys⁶(N-epsilon-nicotinyl-D-Ala¹⁰]LHRH;
[N-Ac-Sar¹-D-4-Cl-Phe²-D-1-Nal³-N-Me-Tyr⁵-D-3-Pal⁶-D-Ala¹⁰]LHRH;
[N-Ac-D-4-Cl-Phe¹-D-4-Cl-Phe²-D-3-Bal³-N-Me-Tyr⁵-D-Lys⁶-D-Ala¹⁰]LHRH;
[N-Ac-D-4-Cl-Phe¹-D-4-Cl-Phe²-D-1-Nal³-N-Me-Tyr⁵-D-Lys⁶-D-Ala¹⁰]LHRH;
[N-Ac-D-4-Cl-Phe¹-D-4-Cl-Phe²-D-1-Nal³-N-Me-Tyr⁵-D-Lys⁶(N-epsilon-nicotinyl)-Lys⁸-D-Ala¹⁰]LHRH;
[N-Ac-D-2-Nal¹-D-4-Cl-Phe²-D-1-Nal³-N-Me-Tyr⁵-D-Lys⁶ (N-epsilon-nicotinyl)-Lys⁸(N-epsilon-isopropyl)-D-Ala¹⁰]LHRH;
[N-Ac-aza-Gly¹-D-4-(Cl-Phe²-D-1-Nal³-N-Me-Tyr⁵-D-Lys⁶(N-epsilon-nicotinyl)-Lys⁸(N-epsilon-isopropyl)-Sar¹⁰]LHRH;
[N-Ac-D-2-Nal¹-D-4-Cl-Phe²-D-1-Nal³-N-Me-Tyr⁵-D-Hcit⁶-Lys⁸(N-epsilon-isopropyl)-D-Ala¹⁰]LHRH;

[N-Ac-D-4-Cl-Phe$^1$-4-Cl-Phe$^2$-D-3-Bal$^3$-N-Me-Tyr$^5$-D-Lys$^6$(N-epsilon-nicotinyl)-D-Ala$^{10}$]LHRH;

[N-Ac-D-2-Nal$^1$-D-4-Cl-Phe$^2$-D-3-Pal$^3$-N-Me-Tyr$^5$-D-Lys$^6$(N-epsilon-nicotinyl)-Lys$^8$(N-epsilon-isopropyl)-D-Ser$^{10}$]LHRH;

[N-Ac-D-2-Nal$^1$-D-4-Cl-Phe$^2$-D-1-Nal$^3$-N-Me-Tyr$^5$-D-Lys$^6$(N-epsilon-nicotinyl)-N-Me-Arg$^8$-D-Ala$^{10}$]LHRH;

[N-Ac-D-2-Nal$^1$-D-4-Cl-Phe$^2$-D-3-Pal$^3$-NMe-Tyr$^5$-D-Arg$^6$-(N$^G$,N$'^G$-diEt)-Arg$^8$(N$^G$,N$'^G$-diEt)-D-Ala$^{10}$]LHRH;

N-Ac-D-2-Nal$^1$-D-4-Cl-Phe$^2$-D-Trp$^3$-NMeTyr$^5$-D-Ser$^6$-(O-alpha-L-Rha)-Azagly$^{10}$]LHRH;

[N-Ac-D-2-Nal$^1$-D-4-Cl-Phe$^2$-D-Pal$^3$-NMeTyr$^5$-D-Cit$^6$-D-Ala$^{10}$]LHRH;

[N-Ac-D-2-Nal$^1$-D-4-Cl-Phe$^2$-D-Pal$^3$-NMeTyr$^5$-D-Hcit$^6$-D-Ala$^{10}$]LHRH;

[N-Ac-D-2-Nal$^1$-D-4-Cl-Phe$^2$-D-Pal$^3$-NMeArg$^5$-D-4-(4-methoxybenzoyl)Hala$^6$-D-Ala$^{10}$]LHRH;

[N-Ac-D-2-Nal$^1$-D-4-Cl-Phe$^2$-D-Pal$^3$-NMeTyr$^5$-D-Lys$^6$(N-epsilon-nicotinyl)-Lys$^8$(N-epsilon-isopropyl)-Azagly$^{10}$]-LHRH;

N-Ac-Azagly$^1$-D-4-Cl-Phe$^2$-D-1-Nal$^3$-NMeTyr$^5$-D-Lys$^6$-(N-epsilon-nicotinyl)-Lys$^8$(N-epsilon-isopropyl)-Azagly$^{10}$]-LHRH;

[N-Ac-D-2-Nal$^1$-D-4-Cl-Phe$^2$-D-Pal$^3$-NEtTyr$^5$-D-Lys$^6$(N-epsilon-nicotinyl)-Lys$^8$(N-epsilon-isopropyl)-D-Ala$^{10}$]-LHRH;

[N-Ac-D-2-Nal$^1$-D-4-Cl-Phe$^2$-D-Pal$^3$-N-isopropyl-Tyr$^5$-D-Lys$^6$(N-epsilon-nicotinyl)-Lys$^8$(N-epsilon-isopropyl)-D-Ala$^{10}$]LHRH;

[N-Ac-D-2-Nal$^1$-D-4-Cl-Phe$^2$-D-Pal$^3$-Ser$^4$(O-PO$_3$H$_2$)-NMeTyr$^5$-D-Lys$^6$(N-epsilon-nicotinyl)-Lys$^8$(N-epsilon-isopropyl)-D-Ala$^{10}$]LHRH;

[N-Ac-D-2-Nal$^1$-D-4-Cl-Phe$^2$-D-Pal$^3$-Ser$^4$-NMeTyr$^5$-(O-PO$_3$H$_2$)-D-Lys$^6$(N-epsilon-nicotinyl)-Lys$^8$(N-epsilon-isopropyl)-D-Ala$^{10}$]LHRH;

[N-Ac-Azagly$^1$-D-4-Cl-Phe$^2$-D-Nal$^3$-Ser$^4$(O-PO$_3$H$_2$)-NMeTyr$^5$-D-Lys$^6$(N-epsilon-nicotinyl)-Lys$^8$(N-epsilon-isopropyl)-D-Ala$^{10}$]LHRH;

[N-Ac-Azagly$^1$-D-4-Cl-Phe$^2$-D-Nal$^3$-NMeTyr$^5$-(O-PO$_3$H$_2$)-D-Lys$^6$(N-epsilon-nicotinyl)-Lys$^8$(N-epsilon-isopropyl)-D-Ala$^{10}$]LHRH;

NMeTyr$^5$-D-Lys$^6$(N-epsilon-nicotinyl)-Lys$^8$(N-epsilon-isopropyl)-D-Ala$^{10}$]LHRH;

[N-Ac-D-2-Nal$^1$-D-4-Cl-Phe$^2$-D-Pal$^3$-NMeTyr$^5$-D-Lys$^6$(N-epsilon-nicotinyl-N'-oxide)-Lys$^8$(N-epsilon-isopropyl)-D-Ala$^{10}$]LHRH;

N-Ac-Gly-D-4-Cl-Phe-D-3-Pal-Ser-N-Me-Tyr-D-Lys(N-epsilon-nicotinyl)-Leu-Lys(N-epsilon-isopropyl)-Pro-D-AlaNH$_2$;

N-Ac-D-2-Nal-D-4-Cl-Phe-D-4-Thiaz-Ser-N-Me-Tyr-D-Lys(N-epsilon-nicotinyl)-Leu-Lys(N-epsilon-isopropyl)-Pro-D-AlaNH$_2$;

N-Ac-D-2-Nal-D-4-Cl-Phe-D-3-Pal-Ser-N-Me-Tyr-D-Lys(N-epsilon-nicotinyl)-Leu-Lys(N-epsilon-isopropyl)-Pro-SarNH$_2$;

N-Ac-D-4-Cl-Phe-D-4-Cl-Phe-D-2-Thia-Ser-N-Me-Tyr-D-Lys-N-Me-Leu-Arg-Pro-D-AlaNH$_2$;

N-Ac-D-4-Cl-Phe-D-4-Cl-Phe-D-1-Nal-Ser-N-Me-Tyr-D-Lys-Leu-Arg-Pro-D-AlaNH$_2$;

N-Ac-D-4-Cl-Phe-D-4-Cl-Phe-D-1-Nal-Ser-N-Me-Tyr-D-Lys-Cha-Arg-Pro-D-AlaNH$_2$;

N-Ac-Sar-D-4-Cl-Phe-D-1-Nal-Ser-N-Me-Tyr-D-Lys-Leu-Arg-Pro-D-AlaNH$_2$;

N-Ac-Sar-D-4-Cl-Phe-D-2-Thia-Ser-N-Me-Tyr-D-Lys-Leu-Arg-Pro-D-AlaNH$_2$;

N-Ac-Sar-D-4-Cl-Phe-D-1-Nal-Ser-N-Me-Tyr-D-3-Pal-Leu-Arg-Pro-D-AlaNH$_2$;

N-Ac-Sar-D-4-Cl-Phe-D-1-Nal-Ser-N-Me-Tyr-D-Lys(N-epsilon-nicotinyl)-Leu-Arg-Pro-D-AlaNH$_2$;

N-Ac-Sar-D-4-Cl-Phe-1-Nal-Ser-N-Me-Tyr-D-Lys-Leu-Arg-Pro-D-AlaNH$_2$;

N-Ac-Gly-D-4-Cl-Phe-D-1-Nal-Ser-N-Me-Tyr-D-Lys-Leu-Arg-Pro-D-AlaNH$_2$;

N-Ac-D-4-Cl-Phe-D-4-Cl-Phe-D-3-Bal-Ser-N-Me-Tyr-D-Lys-Leu-Arg-Pro-D-AlaNH$_2$;

N-Ac-D-4-Cl-Phe-D-4-Cl-Phe-D-Trp(formyl)-Ser-N-Me-Tyr-D-Lys-Leu-Arg-Pro-D-AlaNH$_2$;

N-Ac-D-4-Cl-Phe-D-4-Cl-Phe-N-Me-D-1-Nal-Ser-N-Me-Tyr-D-Lys-Leu-Arg-Pro-D-AlaNH$_2$;

N-Ac-D-4-Cl-Phe-D-4-Cl-Phe-D-2-Nal-Ser-N-Me-Tyr-D-Lys(N-epsilon-nicotinyl)-N-Me-Leu-Arg-Pro-D-AlaNH$_2$;

N-Ac-D-4-Cl-Phe-D-4-Cl-Phe-D-2-Thia-Ser-Tyr-D-Lys-Leu-Arg-Pro-SarNH$_2$;

N-Ac-D-4-Cl-Phe-D-4-Cl-Phe-D-1-Nal-Ser-N-Me-Tyr-D-H-Cit-Leu-Arg-Pro-D-AlaNH$_2$;

N-Ac-D-4-Cl-Phe-D-4-Cl-Phe-D-3-Bal-Ser-N-Me-Tyr-D-Lys(N-epsilon-isopropyl)-Leu-Arg-Pro-D-AlaNH$_2$;

N-Ac-D-2-Nal-D-4-Cl-Phe-D-3-Pal-Ser-N-Me-Tyr-D-3-Pal-Leu-Lys(N-epsilon-isopropyl)-Pro-D-AlaNH$_2$;

N-Ac-D-2-Nal-D-4-Cl-Phe-D-3-Pal-Ser-N-Me-Tyr-D-Lys(N-epsilon-2-pyrazincarbonyl)-Leu-Lys(N-epsilon-isopropyl)-Pro-D-AlaNH$_2$;

N-Ac-Sar-D-4-Cl-Phe-D-1-Nal-Ser-N-Me-Tyr-D-Lys(N-epsilon-nicotinyl)-Leu-Lys(N-epsilon-isopropyl)-Pro-D-AlaNH$_2$;

N-Ac-Sar-D-4-Cl-Phe-D-3-Bal-Ser-N-Me-Tyr-D-Lys(N-epsilon-nicotinyl)-Leu-Lys(N-epsilon-isopropyl)-Pro-D-AlaNH$_2$;

N-Ac-alpha-Azagly-D-4-Cl-Phe-D-1-Nal-Ser-N-Me-Tyr-D-Lys(N-epsilon-nicotinyl)-Leu-Lys(N-epsilon-isopropyl)-Pro-D-AlaNH$_2$;

N-Ac-D-2-Nal-D-4-Cl-Phe-D-3-Pal-Ser-N-Me-Tyr-D-Lys(N-epsilon-nicotinyl)-Cha-Arg-Pro-D-AlaNH$_2$;

N-Ac-D-2-Nal-D-4-Cl-Phe-D-3-Pal-Ser-N-Me-Tyr-D-Lys(N-epsilon-nicotinyl)-N-Me-Leu-Lys(N-epsilon-isopropyl)-Pro-D-AlaNH$_2$;

N-Ac-D-4-Cl-Phe-D-4-Cl-Phe-D-2-Thia-Ser-N-Me-Tyr-D-Lys(N-epsilon-nicotinyl)-N-Me-Leu-Arg-Pro-D-Ala-NH$_2$;

N-Ac-D-2-Nal-D-4-Cl-Phe-D-3-Pal-Ser-N-Me-Tyr-D-Lys(N-epsilon-CO-Morph)-Leu-Lys(N-epsilon-isopropyl)-Pro-D-AlaNH$_2$;

N-Ac-D-2-Nal-D-4-Cl-Phe-D-3-Pal-Ser-N-Me-Tyr-D-Lys(N-epsilon-CO-NMePip)-Leu-Lys(N-epsilon-isopropyl)-Pro-D-AlaNH$_2$;

N-acetyl-alpha-aza-alanyl-D-3-(4-chlorophenyl)alanyl-D-3-(1-naphthyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-3-(4-chlorophenyl)alanyl-D-3-(4-chlorophenyl)alanyl-D-3-(1-naphthyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-3-(2-naphthyl)alanyl-D-3-(4-chlorophenyl)alanyl-D-3-(1-naphthyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-phenylalanyl-D-3-(4-chlorophenyl)alanyl-D-3-(1-naphthyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-3-(4-fluorophenyl)alanyl-D-3-(4-chlorophenyl)alanyl-D-3-(1-naphthyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-sarcosyl-D-3-(4-chlorophenyl)alanyl-D-3-(1-naphthyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-methyl-alpha-aza-pyroglutamyl-D-3-(4-chlorophenyl)alanyl-D-3-(1-naphthyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-tyrosyl(O-methyl)-D-3-(4-chlorophenyl)alanyl-D-3-(1-naphthyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-3-(3-benzthienyl)alanyl-D-3-(4-chlorophenyl)alanyl-D-3-(1-naphthyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-3-(2-thienyl)alanyl-D-3-(4-chlorophenyl)alanyl-D-3-(1-naphthyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-glycyl-D-3-(4-chlorophenyl)alanyl-D-tryptyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-glycyl-D-3-(4-chlorophenyl)alanyl-D-tryptyl(N-indole-formyl)-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-glycyl-D-3-(4-chlorophenyl)alanyl-D-3-(3-benzthienyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-glycyl-D-3-(4-chlorophenyl)alanyl-D-3-(4-chlorophenyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-glycyl-D-3-(4-chlorophenyl)alanyl-D-3-(cyclohexyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-glycyl-D-3-(4-chlorophenyl)alanyl-D-3-(2-thienyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-glycyl-D-3-(4-chlorophenyl)alanyl-D-3-(4-thiazolyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-glycyl-D-3-(4-chlorophenyl)alanyl-D-3-(3-pyridyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-glycyl-D-3-(4-chlorophenyl)alanyl-D-tryptyl-seryl-N-alpha-methyl-tyrosyl(O-methyl)-D-lysyl(N-epsilon-nicotinyl)-leucyl-lysyl(N-epsilon-isopropyl)-prolyl-D-alanylamide;

N-acetyl-alpha-aza-glycyl-D-3-(4-chlorophenyl)alanyl-D-tryptyl(N-indole-formyl)-seryl-N-alpha-methyl-tyrosyl(O-methyl)-D-lysyl(N-epsilon-nicotinyl)-leucyl-lysyl(N-epsilon-isopropyl)-prolyl-D-alanylamide;

N-acetyl-alpha-aza-glycyl-D-3-(4-chlorophenyl)alanyl-D-3-(3-benzthienyl)alanyl-seryl-N-alpha-methyl-tyrosyl(O-methyl)-D-lysyl(N-epsilon-nicotinyl)-leucyl-lysyl(N-epsilon-isopropyl)-prolyl-D-alanylamide;

N-acetyl-alpha-aza-glycyl-D-3-(4-chlorophenyl)alanyl-D-3-(4-chlorophenyl)alanyl-seryl-N-alpha-methyl-tyrosyl(O-methyl)-D-lysyl(N-epsilon-nicotinyl)-leucyl-lysyl(N-epsilon-isopropyl)-prolyl-D-alanylamide;

N-acetyl-alpha-aza-glycyl-D-3-(4-chlorophenyl)alanyl-D-3-(cyclohexyl)alanyl-seryl-N-alpha-methyl-tyrosyl(O-methyl)-D-lysyl(N-epsilon-nicotinyl)-leucyl-lysyl(N-epsilon-isopropyl)-prolyl-D-alanylamide;

N-acetyl-alpha-aza-glycyl-D-3-(4-chlorophenyl)alanyl-D-3-(2-thienyl)alanyl-seryl-N-alpha-methyl-tyrosyl(O-methyl)-D-lysyl(N-epsilon-nicotinyl)-leucyl-lysyl(N-epsilon-isopropyl)-prolyl-D-alanylamide;

N-acetyl-alpha-aza-glycyl-D-3-(4-chlorophenyl)alanyl-D-3-(4-thiazolyl)alanyl-seryl-N-alpha-methyl-tyrosyl(O-methyl)-D-lysyl(N-epsilon-nicotinyl)-leucyl-lysyl(N-epsilon-isopropyl)-prolyl-D-alanylamide;

N-acetyl-alpha-aza-glycyl-D-3-(4-chlorophenyl)alanyl-D-3-(3-pyridyl)alanyl-seryl-N-alpha-methyl-tyrosyl(O-methyl)-D-lysyl(N-epsilon-nicotinyl)-leucyl-lysyl(N-epsilon-isopropyl)-prolyl-D-alanylamide;

N-acetyl-alpha-aza-glycyl-D-3-(4-chlorophenyl)alanyl-D-3-(3-benzthienyl)alanyl-seryl-N-alpha-methyl-tyrosyl(O-methyl)-D-lysyl(N-epsilon-nicotinyl)-leucyl-lysyl(N-epsilon-isopropyl)-prolyl-D-alanylamide;

N-acetyl-sarcosyl-D-3-(4-chlorophenyl)alanyl-D-tryptyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-sarcosyl-D-3-(4-chlorophenyl)alanyl-D-tryptyl(N-indole-formyl)-seryl-N-alpha-methyl-tyrosyl-D-lysyl(N-epsilon-nicotinyl)-leucyl-lysyl(N-epsilon-isopropyl)-prolyl-D-alanylamide;

N-acetyl-sarcosyl-D-3-(4-chlorophenyl)alanyl-D-3-(3-benzthienyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-sarcosyl-D-3-(4-chlorophenyl)alanyl-D-3-(4-chlorophenyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-sarcosyl-D-3-(4-chlorophenyl)alanyl-D-3-(cyclohexyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-sarcosyl-D-3-(4-chlorophenyl)alanyl-D-3-(2-thienyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-sarcosyl-D-3-(4-chlorophenyl)alanyl-D-3-(3-pyridyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-glycyl-D-3-(4-chlorophenyl)alanyl-D-tryptyl-seryl-N-alpha-methyl-tyrosyl-D-3-(3-pyridyl)alanyl-leucyl-lysyl(N-epsilon-isopropyl)-prolyl-D-alanylamide;

N-acetyl-alpha-aza-glycyl-D-3-(4-chlorophenyl)alanyl-D-tryptyl(N-indole-formyl)-seryl-N-alpha-methyl-tyrosyl-D-3-(3-pyridyl)alanyl-leucyl-lysyl(N-epsilon-isopropyl)-prolyl-D-alanylamide;

N-acetyl-alpha-aza-glycyl-D-3-(4-chlorophenyl)alanyl-D-3-(3-benzthienyl)alanyl-seryl-N-alpha-methyl-tyrosyl-D-3-(3-pyridyl)alanyl-leucyl-lysyl(N-epsilon-isopropyl)-prolyl-D-alanylamide;

N-acetyl-alpha-aza-glycyl-D-3-(4-chlorophenyl)alanyl-D-3-(4-chlorophenyl)alanyl-seryl-N-alpha-methyl-tyrosyl-D-3-(3-pyridyl)alanyl-leucyl-lysyl(N-epsilon-isopropyl)-prolyl-D-alanylamide;

N-acetyl-alpha-aza-glycyl-D-3-(4-chlorophenyl)alanyl-D-3-(cyclohexyl)alanyl-seryl-N-alpha-methyl-tyrosyl-D-3-(3-pyridyl)alanyl-leucyl-lysyl(N-epsilon-isopropyl)-prolyl-D-alanylamide;

N-acetyl-alpha-aza-glycyl-D-3-(4-chlorophenyl)alanyl-D-3-(2-thienyl)alanyl-seryl-N-alpha-methyl-tyrosyl-D-3-(3-pyridyl)alanyl-leucyl-lysyl(N-epsilon-isopropyl)-prolyl-D-alanylamide;

N-acetyl-alpha-aza-glycyl-D-3-(4-chlorophenyl)alanyl-D-3-(4-thiazolyl)alanyl-seryl-N-alpha-methyl-tyrosyl-D-3-(3-pyridyl)alanyl-leucyl-lysyl(N-epsilon-isopropyl)-prolyl-D-alanylamide;

N-acetyl-alpha-aza-glycyl-D-3-(4-chlorophenyl)alanyl-D-3-(3-pyridyl)alanyl-seryl-N-alpha-methyl-tyrosyl-D-3-(3-pyridyl)alanyl-leucyl-lysyl(N-epsilon-isopropyl)-prolyl-D-alanylamide;

N-acetyl-alpha-aza-glycyl-D-3-(4-fluorophenyl)alanyl-D-tryptyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-glycyl-D-3-(4-fluorophenyl)alanyl-D-tryptyl(N-indole-formyl)-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-glycyl-D-3-(4-fluorophenyl)alanyl-D-3-(3-benzthienyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-glycyl-D-3-(4-fluorophenyl)alanyl-D-3-(4-chlorophenyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-glycyl-D-3-(4-fluorophenyl)alanyl-D-3-(cyclohexyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-glycyl-D-3-(4-fluorophenyl)alanyl-D-3-(2-thienyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-glycyl-D-3-(4-fluorophenyl)alanyl-D-3-(4-thiazolyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-glycyl-D-3-(4-fluorophenyl)alanyl-D-3-(3-pyridyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-glycyl-D-3-(4-fluorophenyl)alanyl-D-3-(3-quinolyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-glycyl-D-3-(2-naphthyl)alanyl-D-tryptyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-glycyl-D-3-(2-naphthyl)alanyl-D-tryptyl(N-indole-formyl)-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-glycyl-D-3-(2-naphthyl)alanyl-D-3-(3-benzthienyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-glycyl-D-3-(2-naphthyl)alanyl-D-3-(4-chlorophenyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-glycyl-D-3-(2-naphthyl)alanyl-D-3-(cyclohexyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-glycyl-D-3-(2-naphthyl)alanyl-D-3-(2-thienyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-glycyl-D-3-(2-naphthyl)alanyl-D-3-(4-thiazolyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-glycyl-D-3-(2-naphthyl)alanyl-D-3-(3-pyridyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-glycyl-D-3-(2-naphthyl)alanyl-D-3-(3-quinolyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-glycyl-D-phenylalanyl-D-tryptyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-glycyl-D-phenylalanyl-D-tryptyl(N-indole-formyl)-seryl-N-alpha-methyl06851-tyrosyl-D-lysyl(N-epsilon-nicotinyl)-leucyl-lysyl(N-epsilon-isopropyl)-prolyl-D-alanylamide;

N-acetyl-alpha-aza-glycyl-D-phenylalanyl-D-3-(3-benzthienyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-glycyl-D-phenylalanyl-D-3-(4-chlorophenyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-glycyl-D-phenylalanyl-D-3-(cyclohexyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-glycyl-D-phenylalanyl-D-3-(2-thienyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-glycyl-D-phenylalanyl-D-3-(4-thiazolyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-glycyl-D-phenylalanyl-D-3-(3-pyridyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-Ac-D-2-Nal-alpha-aza-4-Cl-Phe-D-3-Pal-Ser-N-Me-Tyr-D-Lys(N-epsilon-nicotinyl)-Leu-Lys(N-epsilon-isopropyl)-Pro-D-AlaNH$_2$;

N-acetyl-D-3-(2-naphthyl)alanyl-alpha-aza-3-(2-naphthyl)alanyl-D-3-(3-pyridyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-D-3-(2-naphthyl)alanyl-alpha-aza-3-(4-fluorophenyl)alanyl-D-3-(3-pyridyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-D-3-(2-naphthyl)alanyl-alpha-aza-3-(4-methoxyphenyl)alanyl-D-3-(3-pyridyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-D-3-(2-naphthyl)alanyl-alpha-aza-tryptyl-D-3-(3-pyridyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-D-3-(2-naphthyl)alanyl-alpha-aza-3-(3-benzthienyl)alanyl-D-3-(3-pyridyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-D-3-(2-naphthyl)alanyl-alpha-aza-3-(cyclohexyl)alanyl-D-3-(3-pyridyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-D-3-(2-naphthyl)alanyl-alpha-aza-3-(2-thienyl)alanyl-D-3-(3-pyridyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-Ac-alpha-aza-Gly-alpha-aza-4-Cl-Phe-D-1-Nal-Ser-N-Me-Tyr-D-Lys(N-epsilon-nicotinyl)-Leu-Lys(N-epsilon-isopropyl)-Pro-D-AlaNH$_2$;

N-acetyl-alpha-aza-glycyl-alpha-aza-3-(4-chlorophenyl)alanyl-D-3-(3-benzthienyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-glycyl-alpha-aza-3-(4-chlorophenyl)alanyl-D-tryptyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-glycyl-alpha-aza-3-(4-chlorophenyl)alanyl-D-tryptyl(N-indole-formyl)-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-glycyl-alpha-aza-3-(4-chlorophenyl)alanyl-D-3-(4-chlorophenyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-glycyl-alpha-aza-3-(4-chlorophenyl)alanyl-D-3-(2-thienyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-glycyl-alpha-aza-3-(4-chlorophenyl)alanyl-D-3-(2-naphthyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-Ac-Sar-alpha-aza-4-Cl-Phe-D-1-Nal-Ser-N-Me-Tyr-D-Lys(N-epsilon-nicotinyl)-Leu-Lys(N-epsilon-isopropyl)-Pro-D-AlaNH$_2$;

N-acetyl-sarcosyl-alpha-aza-3-(4-chlorophenyl)alanyl-D-3-(3-benzthienyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-sarcosyl-alpha-aza-3-(4-chlorophenyl)alanyl-D-3-(2-thienyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-sarcosyl-alpha-aza-3-(4-chlorophenyl)alanyl-D-tryptyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-sarcosyl-alpha-aza-3-(4-chlorophenyl)alanyl-D-tryptyl(N-indole-formyl)-seryl-N-alpha-methyl-tyrosyl-D-lysyl(N-epsilon-nicotinyl)-leucyl-lysyl(N-epsilon-isopropyl)-prolyl-D-alanylamide;

N-acetyl-sarcosyl-alpha-aza-3-(4-chlorophenyl)alanyl-D-3-(4-chlorophenyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-sarcosyl-alpha-aza-3-(4-chlorophenyl)alanyl-D-3-(4-methoxyphenyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-D-3-(2-naphthyl)alanyl-D-3-(4-chlorophenyl)alanyl-D-3-(1-naphthyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-D-3-(2-naphthyl)alanyl-D-3-(4-chlorophenyl)alanyl-D-3-(3-benzthienyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-D-3-(2-naphthyl)alanyl-D-3-(4-chlorophenyl)alanyl-D-3-(2-thienyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-D-3-(2-naphthyl)alanyl-D-3-(4-chlorophenyl)alanyl-D-tryptyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-D-3-(2-naphthyl)alanyl-D-3-(4-chlorophenyl)alanyl-D-tryptyl(N-indole-formyl)-seryl-N-alpha-methyl-tyrosyl-D-lysyl(N-epsilon-nicotinyl)-leucyl-lysyl(N-epsilon-isopropyl)-prolyl-D-alanylamide;

N-acetyl-D-3-(2-naphthyl)alanyl-D-3-(4-chlorophenyl)alanyl-D-3-(4-methoxyphenyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-D-3-(2-naphthyl)alanyl-D-3-(4-chlorophenyl)alanyl-D-tyrosyl(O-methyl)-seryl-N-alpha-methyl-tyrosyl-D-lysyl(N-epsilon-nicotinyl)-leucyl-lysyl(N-epsilon-isopropyl)-prolyl-D-alanylamide;

N-acetyl-D-3-(2-naphthyl)alanyl-D-3-(4-chlorophenyl)alanyl-D-3-(3-quinolyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-D-3-(2-naphthyl)alanyl-D-3-(4-chlorophenyl)alanyl-D-3-(cyclohexyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-Ac-D-2-Nal-D-4-Cl-Phe-N-alpha-aza-3-Pal-Ser-N-Me-Tyr-D-Lys(N-epsilon-nicotinyl)-Leu-Lys(N-epsilon-isopropyl)-Pro-D-AlaNH$_2$;

N-acetyl-D-3-(2-naphthyl)alanyl-D-3-(4-chlorophenyl)alanyl-N-alpha-aza-3-(1-naphthyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-D-3-(2-naphthyl)alanyl-D-3-(4-chlorophenyl)alanyl-N-alpha-aza-3-(3-benzthienyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-D-3-(2-naphthyl)alanyl-D-3-(4-chlorophenyl)alanyl-N-alpha-aza-tryptyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-D-3-(2-naphthyl)alanyl-D-3-(4-chlorophenyl)alanyl-N-alpha-aza-tryptyl(N-indole-formyl)-seryl-N-alpha-methyl-tyrosyl-D-lysyl(N-epsilon-nicotinyl)-leucyl-lysyl(N-epsilon-isopropyl)-prolyl-D-alanylamide;

N-acetyl-D-3-(2-naphthyl)alanyl-D-3-(4-chlorophenyl)alanyl-N-alpha-aza-tryptyl(N-indole-methyl)-seryl-N-alpha-methyl-tyrosyl-D-lysyl(N-epsilon-nicotinyl)-leucyl-lysyl(N-epsilon-isopropyl)-prolyl-D-alanylamide;

N-acetyl-D-3-(2-naphthyl)alanyl-D-3-(4-chlorophenyl)alanyl-N-alpha-aza-3-(4-methylphenyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-D-3-(2-naphthyl)alanyl-D-3-(4-chlorophenyl)alanyl-N-alpha-aza-3-(2-thienyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-D-3-(2-naphthyl)alanyl-D-3-(4-chlorophenyl)alanyl-N-alpha-aza-3-(4-chlorophenyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-D-3-(2-naphthyl)alanyl-D-3-(4-chlorophenyl)alanyl-N-alpha-aza-3-(4-methoxyphenyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-D-3-(2-naphthyl)alanyl-D-3-(4-chlorophenyl)alanyl-N-alpha-aza-3-(3-quinolyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-D-3-(2-naphthyl)alanyl-D-3-(4-chlorophenyl)alanyl-N-alpha-aza-3-(cyclohexyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-Ac-aza-Gly-D-4-Cl-Phe-D-1-Nal-N-Me-Ser-Tyr-D-Lys(N-epsilon-nicotinyl)-N-Me-Leu-Lys(N-epsilon-isopropyl)-Pro-D-AlaNH$_2$;

N-Ac-aza-Gly-D-4-Cl-Phe-D-1-Nal-N-Me-Ser-N-Me-Tyr-D-Lys(N-epsilon-nicotinyl)-Leu-Lys(N-epsilon-isopropyl)-Pro-D-AlaNH$_2$;

N-Ac-aza-Gly-D-4-Cl-Phe-D-1-Nal-Tyr-N-Me-Tyr-D-Lys(N-epsilon-nicotinyl)-Leu-Lys(N-epsilon-isopropyl)-Pro-D-AlaNH$_2$;

N-Ac-aza-Gly-D-4-Cl-Phe-D-1-Nal-Ala-N-Me-Tyr-D-Lys(N-epsilon-nicotinyl)-N-Me-Leu-Lys(N-epsilon-isopropyl)-Pro-D-AlaNH$_2$; epsilon-nicotinyl)-Leu-Lys(N-epsilon-isopropyl)-Pro-D-AlaNH$_2$;

N-Ac-aza-Gly-D-4-Cl-Cl-Phe-D-1-Nal-Gln-N-Me-Tyr-D-Lys(N-epsilon-nicotinyl)-Leu-Lys(N-epsilon-isopropyl)-Pro-D-AlaNH$_2$;

N-Ac-D-2-Nal-D-4-Cl-Phe-D-3-Pal-Ser-N-Me-Tyr(O-Me)-D-Lys(N-epsilon-nicotinyl)-Leu-Lys(N-epsilon-isopropyl)-Pro-D-AlaNH$_2$;

N-Ac-aza-Gly-D-4-Cl-Phe-D-1-Nal-Ser-N-Me-Tyr(O-Me)-D-Lys(N-epsilon-nicotinyl)-Leu-Lys(N-epsilon-isopropyl)-Pro-D-AlaNH$_2$;

N-Ac-aza-Gly-D-4-Cl-Phe-D-1-Nal-Ser-N-Me-Phe-D-Lys(N-epsilon-nicotinyl)-Leu-Lys(N-epsilon-isopropyl)-Pro-D-AlaNH$_2$;

N-Ac-aza-Gly-D-4-Cl-Phe-D-1-Nal-Ser-N-Me-4-F-Phe-D-Lys(N-epsilon-nicotinyl)-Leu-Lys(N-epsilon-isopropyl)-Pro-D-AlaNH$_2$;

N-Ac-Sar-D-4-Cl-Phe-D-3-Bal-Ser-N-Me-Tyr(O-Me)-D-Lys(N-epsilon-nicotinyl)-Leu-Lys(N-epsilon-isopropyl)-Pro-D-AlaNH$_2$;

N-Ac-aza-Gly-D-4-Cl-Phe-D-1-Nal-Ser-N-Me-Arg-D-Lys(N-epsilon-nicotinyl)-Leu-Lys(N-epsilon-isopropyl)-Pro-D-AlaNH$_2$;

N-Ac-D-2-Nal-D-4-Cl-Phe-D-3-Pal-Ser-N-Me-Lys(N-epsilon-nicotinyl)-D-Lys(N-epsilon-nicotinyl)-Leu-Lys(N-epsilon-isopropyl)-Pro-D-AlaNH$_2$;

N-Ac-D-2-Nal-D-4-Cl-Phe-D-3-Pal-Ser-N-Me-Orn(N-delta-nicotinyl)-D-Trp-Leu-Lys(N-epsilon-isopropyl)-Pro-D-AlaNH$_2$;

N-Ac-aza-Gly-D-4-Cl-Phe-D-1-Nal-Ser-N-Me-Arg-D-Lys(N-epsilon-anisic)-Leu-Arg-Pro-D-AlaNH$_2$;

N-Ac-D-2-Nal-D-4-Cl-Phe-D-3-Pal-Ser-N-Me-Arg-D-Lys(N-epsilon-anisic)-Leu-Lys(N-epsilon-isopropyl)-Pro-D-AlaNH$_2$;

N-Ac-D-2-Nal-D-4-Cl-Phe-D-3-Pal-Ser-N-Me-Hcit(NH$_2$)-D-Lys(N-epsilon-nicotinyl)-Leu-Lys(N-epsilon-isopropyl)-Pro-D-AlaNH$_2$;

N-Ac-D-2-Nal-D-4-Cl-Phe-D-3-Pal-Ser-N-Me-Hcit(N-HAc)-D-Lys(N-epsilon-nicotinyl)-Leu-Lys(N-epsilon-isopropyl)-Pro-D-AlaNH$_2$;

N-Ac-aza-Gly-D-4-Cl-Phe-D-Tmp-Ser-N-Me-Tyr-D-Lys(N-epsilon-nicotinic)-Leu-Lys(N-epsilon-isopropyl)-Pro-D-AlaNH$_2$;

N-Ac-D-2-Nal-D-4-Cl-Phe-D-3-Pal-Ser-N-Me-Tyr-D-3-Bal-Leu-Lys(N-epsilon-isopropyl)-Pro-D-AlaNH$_2$;

N-acetyl-D-3-(2-naphthyl)alanyl-D-3-(4-chlorophenyl)alanyl-D-3-(3-pyridyl)alanyl-seryl-N-alpha-methyl-tyrosyl-D-lysyl-leucyl-lysyl(N-epsilon-isopropyl)-prolyl-D-alanylamide;

N-acetyl-D-3-(2-naphthyl)alanyl-D-3-(4-chlorophenyl)alanyl-D-3-(3-pyridyl)alanyl-seryl-N-alpha-methyl-tyrosyl-D-ornithyl-leucyl-lysyl(N-epsilon-isopropyl)-prolyl-D-alanylamide;

N-acetyl-D-3-(2-naphthyl)alanyl-D-3-(4-chlorophenyl)alanyl-D-3-(3-pyridyl)alanyl-seryl-N-alpha-methyl-tyrosyl-D-citrullyl-leucyl-lysyl(N-epsilon-isopropyl)-prolyl-D-alanylamide;

N-acetyl-D-3-(2-naphthyl)alanyl-D-3-(4-chlorophenyl)alanyl-D-3-(3-pyridyl)alanyl-seryl-N-alpha-methyl-tyrosyl-D-homocitrullyl-leucyl-lysyl(N-epsilon-isopropyl)-prolyl-D-alanylamide;

N-acetyl-D-3-(2-naphthyl)alanyl-D-3-(4-chlorophenyl)alanyl-D-3-(3-pyridyl)alanyl-seryl-N-alpha-methyl-tyrosyl-D-arginyl(N$^G$-diethyl)-leucyl-lysyl(N-epsilon-isopropyl)-prolyl-D-alanylamide;

N-acetyl-D-3-(2-naphthyl)alanyl-D-3-(4-chlorophenyl)alanyl-D-3-(3-pyridyl)alanyl-seryl-N-alpha-methyl-tyrosyl-D-arginyl-leucyl-lysyl(N-epsilon-isopropyl)-prolyl-D-alanylamide;

N-Ac-D-2-Nal-D-4-Cl-Phe-D-3-Pal-Ser-N-Me-Tyr-D-Lys(N-epsilon-anisic)-Leu-Lys(N-epsilon-isopropyl)-Pro-D-AlaNH$_2$;

N-Ac-D-2-Nal-D-4-Cl-Phe-D-1-Nal-Ser-N-Me-Tyr-D-Ser(O-alpha-L-Rha)-Leu-Lys(N-epsilon-isopropyl)-Pro-D-AlaNH$_2$;

N-Ac-D-2-Nal-D-4-Cl-Phe-D-3-Pal-Ser-N-Me-Tyr-D-Lys(N-epsilon-nicotinyl)-Cha-Lys(N-epsilon-isopropyl)-Pro-D-AlaNH$_2$;

N-Ac-Sar-D-4-Cl-Phe-D-1-Nal-Ser-N-Me-Tyr-D-Lys(N-epsilon-nicotinyl)-N-Me-Cha-Lys(N-epsilon-isopropyl)-Pro-D-AlaNH$_2$;

N-Ac-aza-Gly-D-4-Cl-Phe-D-1-Nal-Ser-N-Me-Tyr-D-Lys(N-epsilon-nicotinyl)-Ileu-Lys(N-epsilon-isopropyl)-Pro-D-AlaNH$_2$;

N-Ac-Sar-D-4-Cl-Phe-D-1-Nal-Ser-N-Me-Tyr-D-Lys(N-epsilon-nicotinyl)-Ser-Lys(N-epsilon-isopropyl)-Pro-D-AlaNH$_2$;

N-Ac-Sar-D-4-Cl-Phe-D-1-Nal-Ser N-Me-Tyr-D-Lys(N-epsilon-nicotinyl)-Ser-N-Me-Arg-Pro-D-AlaNH$_2$;

N-Ac-D-2-Nal-D-4-Cl-Phe-D-3-Pal-Ser-N-Me-Tyr-D-Lys(N-epsilon-nicotinyl)-Leu-Lys-Pro-D-AlaNH$_2$;

N-Ac-D-2-Nal-D-4-Cl-Phe-D-3-Pal-Ser-N-Me-Tyr-D-Lys(N-epsilon-nicotinyl)-Leu-Lys(N-epsilon-cyclohexyl)-Pro-D-AlaNH$_2$;

N-Ac-D-2-Nal-D-4-Cl-Phe-D-3-Pal-Ser-N-Me-Tyr-D-Lys(N-epsilon-nicotinyl)-Leu-Hcit-Pro-D-AlaNH$_2$;

N-Ac-D-2-Nal-D-4-Cl-Phe-D-3-Pal-Ser-N-Me-Tyr-D-Lys(N-AlaNH$_2$;

N-Ac-D-2-Nal-D-4-Cl-Phe-D-3-Pal-Ser-N-Me-Tyr-D-Lys(N-epsilon-nicotinyl)-Leu-Lys(N-epsilon-CO-hyzAc)-Pro-D-AlaNH$_2$;

N-Ac-Sar-D-4-Cl-Phe-D-1-Nal-Ser-N-Me-Tyr-D-Lys(N-epsilon-nicotinyl)-Leu-Lys(N-epsilon-isopropyl)-Pro-aza-GlyNH$_2$;

N-Ac-aza-Gly-D-4-Cl-Phe-D-1-Nal-Ser-N-Me-Tyr-D-Lys(N-epsilon-nicotinyl)-Leu-Lys(N-epsilon-isopropyl)-Pro-D-SerNH$_2$;

N-Ac-D-2-Nal-D-4-Cl-Phe-D-3-Pal-Ser-NMe-Tyr-D-Lys(N-epsilon-nicotinyl)-Leu-Lys(N-epsilon-isopropyl)-Pro-AzaglyNH$_2$;

N-Ac-D-2-Nal-D-4-Cl-Phe-D-3-Pal-Ser-N-Me-Arg-D-Mbha-Leu-Arg-Pro-D-AlaNH$_2$;

N-Ac-D-2-Nal-D-4-Cl-Phe-D-3-Pal-Ser-N-Me-Tyr-D-Harg(N$^G$,N$^G$-diEt)-Leu-Harg(N$^G$,N$^G$-diEt)-Pro-D-AlaNH$_2$; and N-Ac-D-2-Nal-D-4-Cl-Phe-D-3-Pal-Ser-NMeTyr-D-Cit-Leu-Arg-Pro-D-AlaNH$_2$.

Effect and Utilities of LHRH Agonists and Antagonists

The LHRH agonist and antagonist compounds of the invention are useful for treatment of precocious puberty, prostate cancer, benign prostatic hypertrophy, endometriosis, uterine fibroids, breast cancer, acne, premenstrual syndrome, polycystic ovary syndrome and diseases which result from excesses or deficiencies in gonadal hormone production in either sex of humans and animals. The LHRH agonists and antagonists of the invention are also useful for controlling reproduction in both females and males. LHRH agonists, when administered in pulses, are useful as fertility promoters. Compounds of the invention are useful for suppressing levels of dihydrotestosterone (DHT). The LHRH agonist compounds of the invention are also useful for growth promotion in female animals and for spawning promotion in fish.

The compounds of the invention are also useful when administered in combination with a steroidal or non-steroidal antiandrogenic agent. Examples of suitable antiandrogenic agents include, but are not limited to, 5,5-dimethyl-3-(4-nitro-3-trifluoromethylphenyl)-2,4-imidazolinedione and 2-methyl-N-(4-nitro 3-trifluoromethylphenyl)-propanamide.

In the practice of the method of this invention an effective amount of a compound of the invention or a pharmaceutical composition containing the same is administered to the human or animal in need of, or desiring, such treatment. These compounds or compositions may be administered by any of a variety of routes depending upon the specific end use, including orally, parenterally (including subcutaneous, intramuscular and intraveneous administration), vaginally (particularly for contraception), rectally, buccally (including sublingually), transdermally or intranasally. The most suitable route in any given case will depend upon the use, particular active ingredient, the subject involved, and the judgment of the medical practitioner. The compound or composition may also be administered by means of slow-release, depot or implant formulations as described more fully herein below.

In general, to modulate levels of sex hormones in male or female mammals for the uses herein above described, it is expedient to administer the active ingredient in amounts between about 0.01 and 10 mg/kg body weight per day, preferably between about 0.1 and 5.0 mg/kg body weight per day. This administration may be accomplished by a single daily administration, by distribution over several applications or by slow release in order to achieve the most effective results.

The exact dose and regimen for administration of these compounds and compositions will necessarily be dependent upon the needs of the individual subject being treated, the type of treatment, the degree of affliction or need and, of course, the judgment of the medical practitioner. In general, parenteral administration requires lower dosage than other methods of administration which are more dependent upon absorption.

A further aspect of the present invention relates to pharmaceutical compositions containing as active ingredient a compound of the present invention which compositions comprise such compound in admixture with a pharmaceutically acceptable, non-toxic carrier. As mentioned above, such compositions may be prepared for use for parenteral (subcutaneous, intramuscular or intraveneous) administration, particularly in the form of liquid solutions or suspensions; for use in vaginal or rectal administration, particularly in semisolid forms such as creams and suppositories; for oral or buccal administration, particularly in the form of tablets or capsules, or intranasally, particularly in the form of powders, nasal drops or aerosols.

The compositions may conveniently be administered in unit dosage form and may be prepared by any of the methods well-known in the pharmaceutical art, for example as described in *Remington's Pharmaceutical Sciences*, Mack Publishing Company, Easton, Pa., 1970. Formulations for parenteral administration may contain as common excipients sterile water or saline, polyalkylene glycols such as polyethylene glycol, oils of vegetable origin, hydrogenated naphthalens and the like. Formulations for inhalation administration may be solid and contain as excipients, for example, lactose, or may be aqueous or oily solutions for administration in the form of nasal drops. For buccal administration typical excipients include sugars, calcium stearate, magnesium stearate, pregelatinated starch, and the like.

It is particularly desirable to deliver the compounds of the present invention to the subject over prolonged periods of time, for example, for periods of one week to one year from a single administration. Various slow release, depot or implant dosage forms may be utilized. For example, a dosage form may contain a pharmaceutically acceptable non-toxic salt of a compound of the invention which has a low degree of solubility in body fluids, for example, (a) an acid addition salt with a polybasic acid such as phosphoric acid, sulfuric acid, citric acid, tartaric acid, tannic acid, pamoic acid, alginic acid, polyglutamic acid, naphthalene mono- or di-sulfonic acids, polygalacturonic acid, and the like; (b) a salt with a polyvalent metal cation such as zinc, calcium, bismuth, barium, magnesium, aluminum, copper, cobalt, nickel, cadmium and the like, or with an organic cation formed from e.g., N,N'-dibenzylethylenediamine or ethylenediamine; or (c) combinations of (a) and (b) e.g.

a zinc tannate salt. Additionally, the compounds of the present invention or, preferably, a relatively insoluble salt such as those just described, may be formulated in a gel, for example, an aluminum monostearate gel with, e.g. sesame oil, suitable for injection. Particularly preferred salts are zinc salts, zinc tannate salts, pamoate salts, and the like. Another type of slow release depot formulation for injection would contain the compound or salt dispersed or encapsulated in a slow degrading, non-toxic, non-antigenic polymer such as a polylactic acid/polyglycolic acid polymer for example as described in U.S. Pat. No. 3,773,919. The compounds of the invention or, preferably, relatively insoluble salts such as those described above may also be formulated in cholesterol matrix pellets, particularly for use in animals. Additional slow release, depot or implant formulations, e.g. liposomes, are well known in the literature. See, for example, *Sustained and Controlled Release Drug Delivery Systems*, J. R. Robinson ed., Marcel Dekker, Inc., New York, 1978. Particular reference with respect to LHRH type compounds may be found, for example, in U.S. Pat. No. 4,010,125.

Synthesis of the Peptides

The polypeptides of the present invention may be synthesized by any techniques that are known to those skilled in the art. For solid phase peptide synthesis, a summary of the many techniques may be found in J. M. Stewart and J. D. Young, *Solid Phase Peptide Synthesis*, W. H. Freeman Co., San Francisco, 1963 and J. Meienhofer, *Hormonal Proteins and Peptides*, Vol. 2., p.46, Academic Press (New York), 1973. For classical solution synthesis see G. Schroder and K. Lupke, *The Peptides*, vol. 1, Academic Press (New York), 1965.

In general, these methods comprise the sequential addition of one or more amino acids or suitably protected amino acids to a growing peptide chain. Normally, either the amino or carboxyl group of the first amino acid is protected by a suitable protecting group. The protected or derivatized amino acid can then be either attached to an inert solid support or utilized in solution by adding the next amino acid in the sequence having the complimentary (amino or carboxyl) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting groups (and any solid support) are removed sequentially or concurrently, to afford the final polypeptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide.

A particularly preferred method of preparing compounds of the present invention involves solid phase peptide synthesis.

In this particularly preferred method the alpha-amino function of the amino acids is protected by an acid or base sensitive group. Such protecting groups should have the properties of being stable to the conditions of peptide linkage formation, while being readily removable without destruction of the growing peptide chain or racemization of any of the chiral centers contained therein. Suitable protecting groups are t-butyloxycarbonyl (Boc), benzyloxycarbonyl (Cbz), biphenylisopropyloxycarbonyl, t-amyloxycarbonyl, isobornyloxycarbonyl, (alpha,alpha)-dimethyl-3,5-dimethoxybenzyloxycarbonyl, o-nitrophenylsulfenyl, 2-cyano-t-butyloxycarbonyl, 9-fluorenylmethyloxycarbonyl and the like. The t-butyloxycarbonyl (Boc) protecting group is preferred.

Particularly preferred side chain protecting groups are, for arginine: nitro, p-toluenesulfonyl, 4-methoxybenzenesulfonyl, Cbz, Boc and adamantyloxycarbonyl; for tyrosine: benzyl, o-bromobenzyloxycarbonyl, 2,6-dichlorobenzyl, isopropyl, cyclohexyl, cyclopentyl and acetyl; for serine: benzyl and tetrahydropyranyl; for histidine: benzyl, Cbz, p-toluenesulfonyl and 2,4-dinitrophenyl; for tryptophan: formyl.

In the solid phase peptide synthesis method, the C-terminal amino acid is attached to a suitable solid support. Suitable solid supports useful for the above synthesis are those materials which are inert to the reagents and reaction conditions of the stepwise condensation-deprotection reactions, as well as being insoluble in the media used. Suitable solid supports are chloromethylpolystyrene-divinylbenzene polymer, hydroxymethylpolystyrene-divinylbenzene polymer, and the like. Chloromethyl-polystyrene-1% divinylbenzene polymer is especially preferred. For the special case where the C-terminus of the compound will be glycinamide, a particularly useful support is the benzhydrylaminopolystyrene-divinylbenzene polymer described by P. Rivaille, et al, *Helv. Chim. Acta.*, 54, 2772 (1971). The coupling to the chloromethyl polystyrene-divinylbenzene type of resin is made by means of the reaction of the alpha-N-protected amino acid, especially the Boc-amino acid, as its cesium, tetramethylammonium, triethylammonium, 1,5-diazabicyclo-[5.4.0]undec-5-ene, or similar salt. The coupling reaction is accomplished in a solvent such as ethanol, acetonitrile, N,N-dimethylformamide (DMF), and the like, with the chloromethyl resin at an elevated temperature, for example between about 40° and 60° C., for from about 12 to 48 hours. Preferred reagents and reaction conditions involve the coupling of an alpha-N-Boc amino acid cesium salt with the resin in DMF at about 50° C. for about 24 hours. The alpha-N-Boc-amino acid is attached to the benzhydrylamine resin by means of N,N'-dicyclohexylcarbodiimide (DCC) or N,N'-diisopropylcarbodiimide (DIC) with or without 1-hydroxybenzotriazole (HOBT), benzotriazol-1-yloxy-tris-(dimethylamino)-phosphonium-hexafluorophosphate (BOP) or bis(2-oxo-3-oxazolidinyl)phosphine chloride (BOPCl), mediated coupling for from about 1 to about 24 hours, preferably about 12 hours at a temperature of between about 10° and 50° C., preferably 25° C. in a solvent such as dichloromethane or DMF, preferably dichloromethane. The coupling of the carboxyl group to the N-methyl-Ser-(OBzl) attached to the peptide resin requires catalysis by 4-dimethylaminopyridine (DMAP), in addition to the carbodiimide reagent.

The coupling of successive protected amino acids can be carried out in an automatic polypeptide synthesizer as is well known in the art. The removal of the alpha-N-protecting groups may be performed in the presence of, for example, a solution of trifluoroacetic acid in methylene chloride, hydrogen chloride in dioxane, hydrogen chloride in acetic acid, or other strong acid solution, preferably 50% trifluoroacetic acid in dichloromethane at about ambient temperature. Each protected amino acid is preferably introduced in 0.4M concentration and approximately 3.5 molar excess and the coupling may be carried out in dichloromethane, dichloromethane/DMF mixtures, DMF and the like, especially in methylene chloride at about ambient temperature. The coupling agent is normally DCC in dichloromethane but may be N,N'-di-isopropylcarbodiimide (DIC) or other carbodiimide either alone or in the presence of HOBT, N-hydroxysuccinimide, other N-hydroxyimides or oximes. Alternately, protected amino acid active ester (e.g. p-nitrophenyl, pentafluorophenyl and the like) or symmetrical anhydrides may be used.

At the end of the solid phase synthesis the fully protected polypeptide is removed from the resin. When the linkage to the resin support is of the benzyl ester type, cleavage is by means of aminolysis with an alkylamine or fluoroalkylamine for peptides with a proline C-terminus, or by aminolysis with, for example, ammonia/methanol or ammonia/ethanol for peptides with a glycine C-terminus at a temperature between about 10° and 50° C., preferably about 25° C., for between about 12 and 48 hours preferably about 18 hours. Alternatively, the peptide may be removed from the resin by transesterification, e.g., with methanol, followed by aminolysis or by direct transamidation. The protected peptide may be purified at this point by silica gel chromatography or taken to the next step directly. The removal of the side chain protecting groups from the polypeptide is performed by treating the aminolysis product with, for example, anhydrous liquid hydrogen fluoride in the presence of anisole and dimethylphosphite or other carbonium scavenger, treatment with hydrogen fluoride/pyridine complex, treatment with tris(trifluoroacetyl)boron and trifluoroacetic acid, by reduction with hydrogen and palladium on carbon on polyvinylpyrrolidone, or by reduction with sodium in liquid ammonia. Side chain protecting groups are preferably removed with liquid hydrogen fluoride in the presence of anisole and dimethylphosphite at a temperature between about $-10°$ and $+10°$ C., preferably about 0° C., for between about 15 minutes and 1 hour. The fully deprotected polypeptide is then purified by a sequence of chromatographic steps employing any or all of the following types: ion exchange on a weakly basic resin in the acetate form; hydrophobic adsorption chromatography on underivatized polystyrene-divinylbenzene (for example Amberlite XAD); silica gel adsorption chromatography; ion exchange chromatography on carboxymethylcellulose; partition chromatography, e.g., on Sephadex G-25, LH-20, or countercurrent distribution; high performance liquid chromatography (HPLC), especially reverse phase HPLC on octyl- or octadecylsilyl-silica bonded phase column packing.

If a racemic amino acid is used in the 6 position, the diastereomeric nonapeptide or decapeptide final products are separated, and the desired peptide containing a D-amino acid in the appropriate position is isolated and purified, preferably during the above-described chromatographic process.

The preparation of peptides having C-terminal azaglycine amides is preferably done using classical peptide solution synthesis using known peptide intermediates. This is described in more detail in Example 9.

The details for the preparation of peptides using classical peptide solution synthesis are described in Example 2.

The following examples will serve to further illustrate the preparation of the novel compounds of the invention.

Preparation A

N-(t-Butoxycarbonyl)-N-Methyl-O-Benzyl-L-Serine Cyclohexylamine Salt

Methyl iodide (227.2 g) was added to a solution of N-Boc-O-benzyl-L-serine (23.68 g) in dry and freshly distilled dimethoxyethane (DME) (370 ml) stirred under nitrogen and cooled to 0° C. Subsequently, sodium hydride (50% oil dispersion) (6.4 g) was added in portions over 15 minutes. The reaction mixture was further stirred at 0°–5° C. for 22 hours and then decomposed by water, and the organic layer was concentrated. The residue was taken up in water (500 ml) and washed with ether (3×100 ml). The aqueous layer was acidified with cold 1N HCl to pH 3.0, and the oil that separated was extracted into ether (3×300 ml). The ethereal layer was washed with cold 1N sodium thiosulfate solution (2×150 ml) and sodium chloride solution (2×150 ml), dried ($Na_2SO_4$) and concentrated. The crude product was dissolved in ether (300 ml), and cyclohexylamine (8.3 g) was added. The salt that separated was filtered and dried to give N-(t-butoxycarbonyl)-N-methyl-O-benzyl-L-serine cyclohexylamine salt (CHA), m.p. 134°–136° C. [alpha]$_D^{24}$ −8.6(C 1,EtOH); Anal. for $C_{22}H_{34}N_2O_5$, Calcd: C, 65.00; H, 8.43; N, 6.89; Found: C, 65.05; H, 8.88; N, 6.91.

Preparation B

N-Acetyl-Sarcosine

4-Dimethylaminopyridine (3.66 g) was added to a solution of sarcosine (26.7 g) and triethylamine (50 ml) in (1:1) dioxane water (150 ml) cooled at 0° C. A solution of acetyl chloride (22.37 ml) in dioxane (20 ml) was added dropwise over a period of 30 min. The reaction solution was then stirred at room temperature for 1 hour and subsequently was acidified to pH 3 with cold 50% aqueous HCl. The mixture was extracted three times with ethyl acetate. The extracts were washed with a saturated NaCl solution, dried over $Na_2SO_4$ and concentrated. The residue was crystallized from ethyl acetate to give N-acetyl-sarcosine, m.p. 135°–137° C. Fab Mass spec. m/e 132 (M+H); Anal. for $C_5H_9NO_3$, Calcd: C, 45.79; H, 6.91; N, 10.68; Found: C, 45.78; H, 7.03; N, 10.64.

Preparation C

The following intermediates were prepared according to the literature:

| Compound | Reference |
| --- | --- |
| L-3-(1-Naphthyl)-alanine | Y. Yabe et al., Chem. Pharm. Bull. 24, 3149 (1976) |
| D-3-(2-Naphthyl)-alanine | J. J. Nestor et al., J. Med. Chem. 25, 795 (1982) |
| D-3-(3-Pyridyl)-alanine | P. N. Rao et al., Int. J. Peptide Protein Res. 29, 118 (1987). |

EXAMPLE 1

(pyro)Glu-His-Trp-N-Me-Ser-Tyr-D-Leu-Leu-Arg-Pro-NHEt

In the reaction vessel of a Biosearch 9500 Peptide Synthesizer was placed 1.5 g (1.05 mmol) of Boc-Pro-O-Resin (Merrifield resin). Amino acids were added sequentially to this resin according to the following synthetic cycle:

1. Deblocking, to remove the t-Boc group from the alpha-amino function of the peptide, is carried out using a solution of 45% trifluoroacetic acid (TFA), 2.5% anisole, 2.0% dimethyl phosphite, and 50.5% methylene chloride. The resin is prewashed with the deblocking solution previously described for one minute and then the deblocking reaction is run for 20 minutes.
2. Base wash, to remove and neutralize the TFA used for deprotection, is carried out using a solution of 10% N,N'-diisopropylethylamine in methylene chloride. The resin is washed with base three times for one minute each time after each deblocking step.
3. Coupling reaction is carried out using a 3.5-fold molar excess of 0.4M DMF solution of a t-Boc protected amino acid derivative along with a 3.5-fold molar excess of 0.4M methylene chloride solution of diisopropylcarbodiimide as activator. The activated amino acid is then coupled to the free alpha amino group of the peptide-resin. The reaction time is as described in the following protocol.
4. Wash, each reaction step is followed by three washes of one minute each: one of methylene chloride, one of (1:1) methylene-chloride-DMF, and one of DMF.

Protocol

The amino acids are coupled to the resin in the following order using the conditions indicated:

| Amino Acid | Wash | Coupling | De-protection |
|---|---|---|---|
| Boc—Arg(Tos) | basewash | two-1 hr | deblock |
| Boc—Leu | basewash | two-1 hr | deblock |
| Boc-D-Leu | basewash | two-1 hr | deblock |
| Boc—Tyr—(o-Br—Cbz) | basewash | two-1 hr | deblock |
| Boc—N—Me—Ser(OBzl) | basewash | two-1 hr | deblock |
| Boc—N-Formyl-Trp | basewash | four-1 hr | deblock |
| with or without 0.1% DMAP | | | |
| Boc—N-im-CBZ—His | basewash | four-1 hr | deblock |
| Cbz-p-Glu | basewash | four-1 hr | none |

Upon the completion of the synthesis the resin is removed from the reaction vessel and dried in vacuo to give the protected polypeptide resin. The protected peptide is removed from the resin upon treatment at room temperature with anhydrous ethylamine with or without 10% DMF or methanol for 48 hours. The resin beads are filtered and washed with methanol. The filtrate is concentrated in vacuo and the residue is triturated with water to give, after filtration and drying, the protected peptide as a white powder. The protecting groups are finally removed upon treatment at 0° C. for 1 hour with 5 to 10 ml anhydrous liquid HF in the presence of 1 ml of anisole and 0.5 ml of dimethyl phosphite. The HF is evaporated and the residue is dissolved in methanol and concentrated in vacuo. The residue is washed twice with ether and then dissolved in a solution of (1:1:0.1) water:acetonitrile:acetic acid, filtered, and lyophilized to give 0.7 g of the crude product. The crude peptide is purified by high performance liquid chromatography on a 25 cm×2.5 cm Dynamax C-18 column (25–40 micron) using solvent mixtures in a gradient ranging from 89% $H_2O$/11% $CH_3CN$/0.1% TFA to 49% $H_2O$/51% $CH_3CN$/0.1% TFA over a period of 50 min, and afterwards changing to 100% $CH_3CN$/0.1% TFA over a period of 10 min. The flow rate is 15 ml/min and UV detection is at 260 nM. The product is eluted at 33.7 min as a single peak, collected and lyophilized to give pure (pyro)Glu-His-Trp-N-Me-Ser-Tyr-D-Leu-Leu-Arg-Pro-NHEt as the trifluoroacetate salt. Fab (fast atom bombardment) Mass spec. m/e 1296 $(M+H)^+$. Amino Acid Anal.: 0.8 Pro; 0.8 Arg; 1.0 Leu; 1.0 Tyr; 1.6 Trp; 1.0 His; 1.0 Glu.

EXAMPLE 2

(pyro)Glu-His-Trp-N-Me-Ser-Tyr-D-Leu-Leu-Arg-Pro-NHEt (pyro)Glu-His-Trp-N-Me-Ser-Tyr-D-Leu-Leu-Arg-Pro-NHEt was prepared using solution synthesis according to the following scheme:

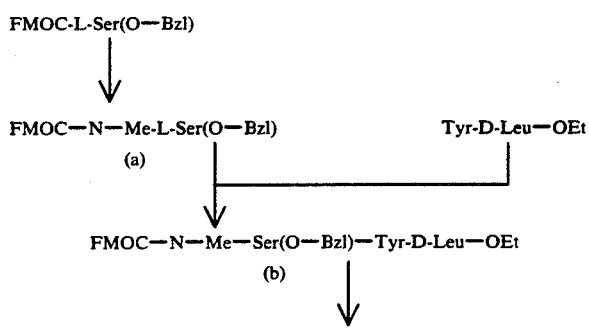

-continued

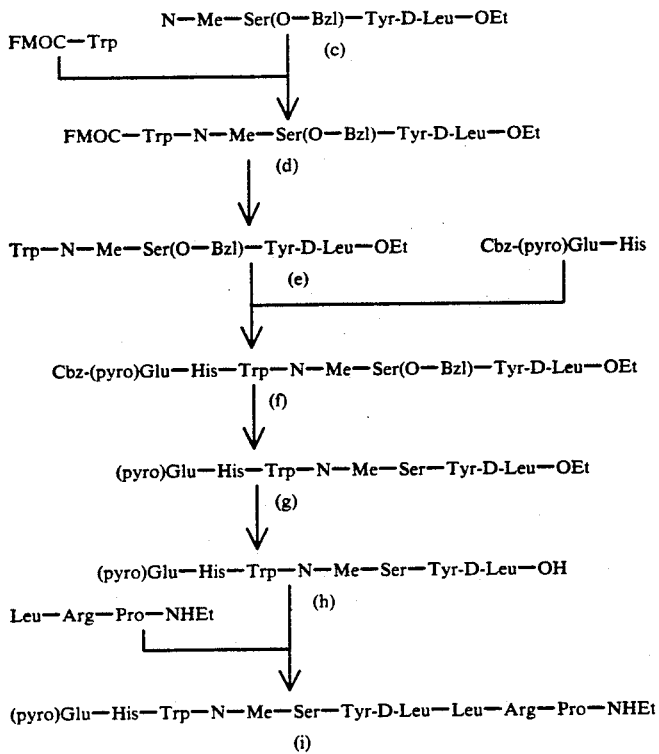

Details of the synthesis are as follows:

(a) FMOC-N-Me-Ser(O-Bzl)

A suspension of FMOC-Ser(O-Bzl) (4.16 g), paraformaldahyde (2.0 g), and p-toluenesulfonic acid (0.2 g) in toluene (400 ml) was heated under reflux with azeotropic water removal for 45 min. The solution was cooled, diluted with ethyl acetate (250 ml) and washed three times with 5% aqueous NaHCO$_3$, dried (Na$_2$SO$_4$), and concentrated in vacuo. The residue was purified by silica gel column chromatography eluting with (8:2) hexane:ethyl acetate to give FMOC-Ser(O-Bzl)-oxazolidin-4-one as a crystalline product, m.p. 108°–109° C. Fab Mass spec. m/e 430(M+H)$^+$. FMOC-Ser-(O-Bzl)-oxazolidin-4-one (3.14 g) was dissolved in chloroform (40 ml) and trifluoroacetic acid (40 ml) and triethylsilane (2.55 g) was added. The solution was stirred at room temperature for 22 hours, then concentrated in vacuo. The residue was purified by silica gel column chromatography eluting with (95:5) methylene chloride:methanol to give FMOC-N-Me-Ser(O-Bzl)-OH as a colorless oil. Fab Mass spec., m/e 432 (M+H)$^+$.

(b) FMOC-N-Me-Ser(O-Bzl)-Tyr-D-Leu-OEt

To a stirred solution of Tyr-D-Leu-OEt hydrochloride (1.649 g) in DMF (10 ml) cooled to 0° C. was added N-ethylmorpholine (0.59 ml) in DMF (1 ml), followed by a solution of FMOC-N-Me-Ser(O-Bzl)-OH (2.18 g) in DMF (5 ml), followed by a solution of HOBt (0.9315 g) in DMF (5 ml), and followed by a solution of DCC (0.947 g) in DMF (2 ml). The reaction solution was stirred at 0° C. for 1 hour and then at room temperature for 4 hours. The solvent was removed in vacuo and the residue was purified by silica gel column chromatography eluting with (95:5) methylene chloride:methanol. The product was obtained as a semisolid. Rf 0.35. Fab Mass spec. m/e 736 (M++H).

(c) N-Me-Ser(O-Bzl)-Tyr-D-Leu-OEt

A solution of FMOC-N-Me-Ser(O-Bzl)-Tyr-D-Leu-OEt (1.95 g) and N,N-diisopropylamine (10 ml) in dry and degassed DMF (10 ml) was stirred at room temperature for 2 hours. The solvent and excess reagents were removed in vacuo and the residue was purified by silica gel column chromatography eluting with (95:5) methylene chloride:methanol. The product was obtained as a low melting solid. Rf 0.24. Fab Mass spec., m/e 514 (M+H)$^+$. Anal for C$_{28}$H$_{39}$N$_3$O$_6$, Calcd: C, 65.47; H, 7.65; N, 8.18; Found: C, 65.10; H, 7.77; N, 7.98.

(d) FMOC-Trp-N-Me-Ser(O-Bzl)-Tyr-D-Leu-OEt

To a stirred solution of N-Me-Ser(O-Bzl)-Tyr-D-Leu-OEt (1.316 g), FMOC-L-Trp (1.09 g) and benzotriazol-1-yloxytris-(dimethylamino) phosphonium hexafluorophosphate (BOP) (1.13 g) in acetonitrile (50 ml) was added triethylamine (0.347 ml). The solution was stirred at room temperature for 5 hours. The solvent was removed in vacuo. The residue was dissolved in ethyl acetate, washed with 5% aqueous NaHCO$_3$, then with 1N HCl, and finally with saturated aqueous NaCl solution, dried (Na$_2$SO$_4$) and concentrated in vacuo. The residue was purified by silica gel column chromatography eluting with (95:5) methylene chloride:methanol. The product was obtained as a semisolid residue. Rf 0.25. Fab Mass spec., m/e 922 (M++H).

(e) Trp-N-Me-Ser(O-Bzl)-Tyr-D-Leu-OEt

A solution of FMOC-Trp-N-Me-Ser(O-Bzl)-Tyr-D-Leu-Et (0.280 g) in acetonitrile (5 ml) and diethylamine (5 ml) was stirred at room temperature for 1 hour. The solvent and excess reagents were removed in vacuo to give the product as a foamy residue. Fab Mass spec.

m/e 700 (M+1)+. The product was used in the next step without further purification.

(f) Cbz-(pyro)Glu-His-Trp-N-Me-Ser(O-Bzl)-Tyr-D-Leu-OEt

To a solution of Trp-N-Me-Ser(O-Bzl)-Tyr-D-Leu-OEt (0.2665 g) in DMF (5 ml) cooled to 0° C. were added sequentially Cbz-(pyro)Glu-His (0.167 g) in DMF (10 ml), HOBt (0.077 g) in DMF (2 ml), and DCC (0.078 g) in DMF (2 ml). The solution was stirred at 0° C. for 2 hours and then at room temperature overnight. The solvent was removed in vacuo and the residue was purified on a silica gel column eluting with (9:1) methylene chloride:methanol. The product was obtained as a solid. Rf 0.317. Fab Mass spec. m/e 1082 (M+H)+.

(g) (pyro)Glu-His-Trp-N-Me-Ser-Tyr-D-Leu-OEt

A solution of Cbz-(pyro)Glu-His-Trp-N-Me-Ser(O-Bzl)-Tyr-D-Leu-OEt (0.787 g) in (9:1) DMF water (15 ml) was hydrogenated overnight under 4 atm. pressure and in the presence of 10% Pd(OH)$_2$/C (0.79 g). The catalyst was filtered and the filtrate was concentrated in vacuo. The residue was triturated with water to give the desired product as an amorphous solid. Fab Mass spec. m/e 857 (M+H)+.

(h) (pyro)Glu-His-Trp-N-Me-Ser-Tyr-D-Leu-OH

To a solution of (pyro)Glu-His-Trp-N-Me-Ser-Tyr-D-Leu-OEt (0.519 g) in (1:1) dioxane-water (16 ml) cooled to 0° C. was added 2N aqueous NaOH (0.6 ml). The resulting solution was stirred at 0° C. for 4 hours, then acidified with 0.1M aqueous HCl to pH 5.0 and lyophilized. Fab Mass spec. of the crude product showed m/e 830 for (M+H). The crude product was taken to the next step without any additional purification.

(i) (pyro)Glu-His-Trp-N-Me-Ser-Tyr-D-Leu-Leu-Arg-Pro-NHEt

To a solution of Leu-Arg-Pro-NHEt dihydrochloride (0.159 g) in DMF (2 ml) cooled to 0° C. was added N-ethylmorpholine (0.042 ml) in DMF (0.2 ml), followed by sequential additions of (pyro)Glu-His-Trp-N-Me-Ser-Tyr-D-Leu-OH (0.3 g) in DMF (5 ml), HOBt (0.066 g) in DMF (2 ml), and DCC (0.0677 g) in DMF (2 ml). The resulting solution was stirred at 0° C. for 2 hours and then at room temperature overnight. The solvent was removed in vacuo. The residue was dissolved in (1:9) acetic acid-water and the insoluble material was filtered. The filtrate was lyophilized. The powder obtained was purified by high performance liquid chromatography (HPLC) using a 25 cm×2.5 cm Dynamax C-18 column (25-40 micron) and solvent mixture gradients ranging from 90% H$_2$O/11% CH$_3$CN/0.1% TFA to 49% H$_2$O/51% CH$_3$CN/0.1% TFA over a period of 50 mins. The flow rate was 15 ml/min and UV detection was at 260 nM. The product was eluted at 30.4 min, was collected and lyophilized to give pure (pyro)Glu-His-Trp-N-Me-Ser-Tyr-D-Leu Arg-Pro-NHEt as the trifluoroacetate salt. Fab Mass spec. m/e 1223 (M+H)+. Amino Acid Anal.: 0.8 Pro; 0.8 Arg; 1.8 Leu; 1.0 Tyr; 1.0 His; 1.0 Glu.

EXAMPLE 3

(pyro)Glu-His-Trp-N-Me-Ser-Tyr-D-(2)-Nal-Leu-Arg-Pro-Gly-NH$_2$

Using the same instrument and a program similar to that described in Example 1, (pyro)Glu-His-Trp-N-Me-Ser-Tyr-D-(2)-Nal-Leu-Arg-Pro-Gly-NH$_2$ was prepared starting with 1.5 g (1.12 mmol) of Boc-Gly-O-Resin and coupling the amino acids in the order described in the following protocol:

| Amino Acid | Wash | Coupling | Deprotection |
|---|---|---|---|
| Boc—Pro | basewash | two-1 hr | deblock |
| Boc—Arg(Tos) | basewash | two-1 hr | deblock |
| Boc—Leu | basewash | two-1 hr | deblock |
| Boc-D-(2)Nal | basewash | two-1 hr | deblock |
| Boc—Tyr—(2-Br—Cbz) | basewash | two-1 hr | deblock |
| Boc—N—Me—Ser(OBzl) | basewash | two-1 hr | deblock |
| Boc—N-formyl-Trp containing 0.1% DMAP | basewash | four-1 hr | deblock |
| Boc—N-im-Cbz—His | basewash | four-1 hr | deblock |
| Cbz—(pyro)Glu | basewash | four-1 hr | none |

The peptide was cleaved from the resin upon treatment with anhydrous liquid ammonia (30 ml) and methanol (5 ml) containing 10% of N,N-dimethylethanolamine at room temperature for 48 hrs. The reaction was worked up as described in Example 1. The protecting groups were removed from the peptide with HF/anisole/dimethylphosphite at 0° C. for 1 hour. The obtained crude peptide was purified by high performance liquid chromatography using the same column and solvent gradient described in Example 1. The product was eluted at 34.9 minutes as a single peak, was collected and lyophilized to give pure (pyro)Glu-His-Trp-N-Me-Ser-Tyr-D-(2)Nal-Leu-Arg-Pro-Gly-NH$_2$ as the trifluoroacetate salt. Fab Mass spec. m/e 1336 (M+H)+. Amino Acid Anal.: 1.0 Gly; 0.8 Pro; 0.9 Arg; 1.0 Leu; 1.0 Tyr; 0.9 Trp; 1.0 His; 1.0 Glu.

EXAMPLE 4

Using the method described in Example 1 and substituting the appropriate amino acids, the following compounds with a C-terminal Pro-NHCH$_2$CH$_3$ can be synthesized:

(pyro)glutamyl-phenylalanyl-tryptyl-N-methylseryl-tyrosyl-D-tryptyl-leucyl-arginyl-prolylethylamide;

(pyro)glutamyl-histidyl-3-(1-naphthyl)alanyl-N-methylseryl-tyrosyl-D-tryptyl-leucyl-arginyl-prolylethylamide;

(pyro)glutamyl-histidyl-tryptyl-N-methylseryl-arginyl-D-tryptyl-leucyl-arginyl-prolylethylamide;

N-acetylphenylalanyl-D-3-4-chlorophenylalanyl-tryptyl-N-methylseryl-tyrosyl-D-tyrosyl-leucyl-arginyl-prolylethylamide;

N-acetyl-D-3-(2-naphthyl)alanyl-D-3-4-fluorophenylalanyl-tryptyl-N-methylseryl-tyrosyl-D-lysyl-leucyl-arginyl-prolylethylamide;

(pyro)glutamyl-histidyl-tryptyl-N-methylseryl-tyrosyl-D-lysyl(N-epsilon-isopropyl)-leucyl-arginyl-prolylethylamide;

(pyro)glutamyl-histidyl-tryptyl-N-methylseryl-tyrosyl-D-seryl(O-t-butyl)-leucyl-arginyl-prolylethylamide;

(pyro)glutamyl-histidyl-tryptyl-N-methylseryl-tyrosyl-D-lysyl(N-epsilon-nicontinoyl)-leucyl-arginyl-prolylethylamide;

(pyro)glutamyl-alpha-methyl-phenylalanyl-tryptyl-N-methylseryl-tyrosyl-D-cyclohexylalanyl-leucyl-arginyl-prolylethylamide;

(pyro)glutamyl-histidyl-tryptyl-N-methylseryl-tyrosyl-D-lysyl(N-epsilon-pyrazinyl-carbonyl)-cyclohexylalanyl-arginyl-prolylethylamide;

N-acetyl-sarcosyl-D-3-4-fluorophenylalanyl-tryptyl-N-methylseryl-tyrosyl-D-tryptyl-leucyl-lysyl-(N-epsilon-isopropyl)-prolylethylamide;

N-acetyl-D-phenylalanyl-D-3-4-chlorophenyl-alanyl-D-3-(1-naphthyl)alanyl-N-methylseryl-tyrosyl-D-prolyl-leucyl-lysyl(N-epsilon-isopropyl)-prolylethylamide;

N-acetylsarcosyl-histidyl-3-(1-naphthyl)-alanyl-N-methylseryl-tyrosyl-D-tyrosyl-cyclohexylalanyl-arginyl-propylethylamide;

N-acetylsarcosyl-D-phenylalanyl-D-tyrosyl-(O-methyl)-N-methylseryl-tyrosyl-D-seryl-leucyl-arginyl-propylethylamide;

N-acetylsarcosyl-phenylalanyl-3-(1-naphthyl)-alanyl-N-methylseryl-tyrosyl-D-seryl(O-t-butyl)-leucyl-arginyl-propylethylamide;

(pyro)glutamyl-phenylalanyl-tryptyl-N-methylseryl-tyrosyl-D-tryptyl-leucyl-lysyl(N-epsilon-isopropyl)-prolylethylamide;

(pyro)glutamyl-histidyl-3-(1-naphthyl)alanyl-N-methylseryl-tyrosy-D-3-(2-naphthyl)alanyl-leucyl-lysyl(N-epsilon-isopropyl)-prolylethylamide.

EXAMPLE 5

Using the method described in Example 2 and substituting the appropriate amino acids, the following compounds can be prepared:

(pyro)glutamyl-histidyl-tryptyl-N-methylseryl-tyrosyl-D-seryl(O-t-butyl)-leucyl-arginyl-prolyl-ethylamide;

N-acetyl-sarcosyl-histidyl-3-(1-naphthyl)alanyl-N-methylseryl-tyrosyl-D-tyrosyl-leucyl-lysyl(N-epsilon-isopropyl)-prolylethylamide;

(pyro)glutamyl-D-phenylalanyl-tryptyl-N-methyseryl-tyrosyl-D-cyclohexylalanyl-leucyl-arginyl-prolylethylamide.

N-acetylsarcosyl-histidyl-tryptyl-N-methyl-seryl-tyrosyl-O-t-butyl-D-seryl-cyclohexylalanyl-lysyl(N-epsilon-isopropyl)-prolylethylamide;

N-acetyl-sarcosyl-D-alpha-methyl-phenylalanyl-3-(1-naphthyl)alanyl-N-methylseryl-tyrosyl-O-t-butyl-D-seryl-leucyl-arginyl-prolylethylamide;

N-acetyl-D-3-(2-naphthyl)alanyl-D-3-4-chlorophenylalanyl-D-tryptyl-N-methyl-seryl-tyrosyl-D-tyrosyl-leucyl-arginyl-prolylethylamide;

N-acetylsarcosyl-histidyl-tryptyl-N-methyl-seryl-lysyl(N-epsilon-pyrazinyl-2-carbonyl)-D-lysyl(N-epsilon-nicotinyl)-leucyl arginyl-prolylethylamide;

(pyro)glutamyl-histidyl-3-(1-naphthyl)alanyl-N-methylseryl-tyrosyl-D-prolyl-leucyl-arginyl-prolyl-ethylamide;

N-acetylsarcosyl-histidyl-tryptyl-N-methyl-seryl-lysyl(N-epsilon-pyrazinyl-2-carbonyl)-D-cyclohexylalanyl-cyclohexylalanyl-ornithinyl(N-delta-isopropyl)-prolyl-ethylamide.

EXAMPLE 6

(pyro)Glu-His-Trp-N-Me-Ser-Tyr-D-Trp-N-Me-Leu-Arg-Pro-NHEt

Using the method described in Example 1, but substituting Boc-Leu with Boc-N-methyl-leucine and adding 0.1% DMAP to the Boc-N-formyl-D-Trp solution in DMF, (pyro)Glu-His-Trp-N-Me-Ser-Tyr-D-Trp-N-Me-Leu-Arg-Pro-NHEt can be prepared.

EXAMPLE 7

N-Ac-Sar-His-Trp-(3)-N-Et-(2)-N-Me-Dap-Tyr-D-Trp-Leu-Arg-Pro-NHEt

Using the method described in Example 1, but substituting the Cbz-(pyro)Glu with N-Ac-Sar and the Boc-N-Me-Ser(OBzl) with Boc-N-Me-DeAla, the protected peptide attached to the resin was prepared. Upon treatment of this resin first with ethylamine and then with HF, as described in Example 1, the crude product was obtained. This peptide was purified by high performance liquid chromatography using the same conditions described in Example 1. N-Ac-Sar-His-Trp-(3)-N-Et-(2)-N-Me-Dap-Tyr-D-Trp-Leu-Arg-Pro-NHEt as the trifluoroacetate salt eluted at 31.05 minutes as a single peak, was collected and lyophilized. Fab Mass spec. m/e 1325 (M++H). Amino Acid Anal.: 1.0 Pro; 1.0 Arg; 1.0 Leu; 1.7 Trp; 1.0 Tyr; 0.9 His; 1.0 Glu.

EXAMPLE 8

Using the method described in Example 7 and substituting the appropriate amino acids, the following peptides can be prepared:

(pyro)glutamyl-histidyl-tryptyl-3-N-ethyl-2-N-methyl-2,3-diaminopropionyl-tyrosyl-D-tryptyl-leucyl-arginyl-prolylethylamide;

N-acetylsarcosyl-D-phenylalanyl-D-tryptyl-3-N-ethyl-2-N-methyl-2,3-diaminopropionyl-tyrosyl-D-tyrosyl-leucyl-arginyl-prolylethylamide;

N-acetyl-D-3-4-chlorophenylalanyl-D-phenylalanyl-D-3-(1-naphthyl)alanyl-3-N-ethyl-2-N-methyl-2,3-diamino-propionyl-tyrosyl-D-lysyl(N-epsilon-nicontinyl)-leucyl-arginyl-prolylethylamide.

N-acetyl-3,4-dehydro-prolyl-D-3-4-chlorophenyl-alanyl-D-tryptyl-3-N-ethyl-2-N-methyl-2,3-diaminopropionyl-tyrosyl-D-lysyl(N-epsilon-picolyl)-valyl-lysyl(N-epsilon-isopropyl)-prolylethylamide.

EXAMPLE 9

(pyro)Glu-His-Trp-N-Me-Ser-Tyr-D-Leu-Leu-Arg-Pro-AzaGly-NH2

This peptide is prepared by classical solution synthesis according to the following scheme:

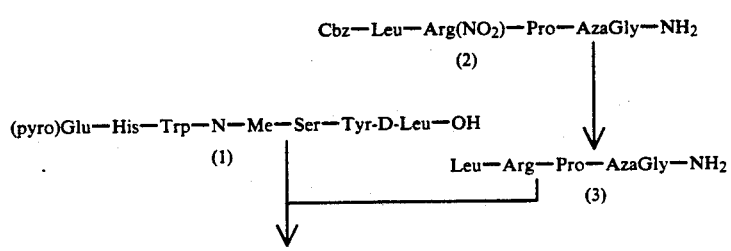

-continued (pyro)Glu—His—Trp—N—Me—Ser—Tyr-D-Leu—Leu—Arg—Pro—AzaGly—HN₂

5

The synthesis of fragment (1) is described in Example 2 and the synthesis of fragment (2) is described in A. S. Dutta, *J. Med. Chem* 21, 1018 (1978). Fragment (2) is converted into (3) by hydrogenolysis and (3) is coupled with (1) using DCC/HOBt. The product is purified by high performance chromatography using conditions similar to those described in Example 1.

EXAMPLE 10

Using the method of Example 3, but substituting Boc-D-(2)Nal with Boc-D-3-(2-benzimidazolyl)-alanate or with Boc-D-3-(2-benzoxazolyl)-alanate, can provide N-acetylsarcosyl-phenylalanyl-tryptyl-N-methylseryl-tyrosyl-3-(2-benzimidazolyl)-D-alanyl-leucyl-arginyl-prolylethylamide and N-acetyl-phenylalanyl-D-3-4-chlorophenylalanyl-D-tryptyl-N-methyl-seryl-tyrosyl-3-(2-benzoxazolyl)-D-alanyl-cyclohexylalanyl-arginyl-prolylethylamide, respectively.

EXAMPLE 11

N-Ac-Sar-D-Phe-D-Trp-N-Me-Ser-Tyr-D-(3)-Pal-Leu-Arg-Pro-NHEt

Using the method of Example 1, but substituting Boc-D-Leu with Boc-3-(3-pyridyl)-D-Ala and running the coupling for this acid four times, each time for 5 hours, N-Acetylsarcosyl-D-phenylalanyl-D-tryptyl-N-methyl-seryl-tyrosyl-D-3-pyridylalanyl-leucyl-arginyl-prolylethylamide can be obtained.

EXAMPLE 12

(2)-N-(Ethylaminocarbonyl)-(5)-N-ethylamido-Glu-His-Trp-N-Me-Ser-Tyr-D-Trp-Leu-Arg-Pro-NHEt Using the same method and same amino acids described in Example 1, Cbz-(pyro)Glu-His(Cbz)-Trp-(N-formyl)-N-Me-Ser(OBzl)-Tyr(O-2-Br-Cbz)-D-Trp(N-formyl)-Leu-Arg(Tos)-Pro-O-Resin was obtained. This peptidoresin was treated with methanol (4 ml) containing 10% dimethylethanolamine and with ethyl amine (30 ml). The mixture was stirred at room temperature for 3 days. The resin was filtered and the filtrate was concentrated in vacuo. The residue was triturated with water. The solid was dried over P₂O₄ for 24 hours to give the protected peptide as a dry white powder. The protecting groups were removed upon treatment at 0° C. for 1 hour with anhydrous liquid HF, in the presence of 1 ml of anisole and 0.5 ml of dimethylphosphite. The excess reagents were removed in vacuo and the residue was dissolved in methanol and then concentrated in vacuo. The residue was washed twice with ether and then dissolved in a solution of (1:1:0.1) water:acetonitrile:acetic acid, filtered, and lyophilized to give the crude product. This was purified by high performance liquid chromatography on a 25 cm×2.5 cm Dynamax C-18 column (25–40 micron) using the same gradient described in Example 1. The product was eluted at 36.5 min. as a single peak, was collected and lyophilized to give pure (2)-N-(ethylaminecarbonyl)-(5)-N-ethylamido-Glu-His-Trp-N-Me-Ser-Tyr-D-Trp-Leu-Arg-Pro-NHEt as the trifluoroacetate salt. FAB Mass spec. m/e 1412 (M+H)⁺. Amino Acid Anal.: 1.0 Pro; 1.2 Arg, 1.0 Leu, 0.9 Tyr, 0.9 Trp, 0.8 His, 0.6 Glu.

EXAMPLE 13

(pyro)-Glu-His-Trp-N-Me-Ser-Tyr-6,7-[2-(S-3-amino-2-oxo-pyrrolidin-1-yl)-S-2-Isopropylmethylacetyl]-Arg-Pro-NHEt (pyro)-Glu-His-Trp-N-Me-Ser Tyr-6,7-[2-(S-3-amino-2-oxo-pyrrolidin-1-yl)-S-2-Isopropylmethylacetyl]-Arg-Pro-NHEt is prepared according to the following steps:

(a) H-Arg(Tos)-Pro-NHEt

The protected dipeptide Arg(Tos)-Pro-NHEt can be prepared by solid phase using Boc-Pro-O-Resin (Merrifield resin), deblocking, and coupling with Boc-Arg(Tos) using the same instrument and the same protocol described in Example 1, and afterwards deblocking the peptide-resin with the deblocking solution which was previously described. The obtained Arg-(Tos)Pro-O-Resin is then treated with ethylamine at room temperature for 48 hours. Work up, trituration of the product with water, over P₂O₅ gives H-Arg-(Tos)-Pro-NHEt.

(b) Boc-[2-(S-3-Amino-2-Oxo-Pyrrolidin-1-yl)-S-2-Isopropylmethylacetic] Acid Boc-[2-(S-3-amino-2-oxo-pyrrolidin-1-yl)-S-2-isopropylmethylacetic acid can be synthesized using the procedure described by D. F. Veber and R. M. Freidinger in U.S. Pat. No. 4,493,934.

(c) Boc-[2-(S-3-Amino-2-Oxo-Pyrrolidin-1-yl)-S-2-Isopropylmethylacetyl]-Arginyl-Prolylethylamide 10 mmol of Boc-[2-(S-3-amino-2-oxo-pyrrolidin-1-yl)-S-2-isopropylmethylacetic] acid is dissolved in 70 ml of degassed DMF and cooled to 0° C. under nitrogen. 19 mmol of H-Arg(Tos)-Pro-NHEt, which was previously described, is dissolved in 30 ml of degassed DMF, and cooled. To the acid solution 11 mmol of diphenylphosphorylazide and 11 mmol of triethylamine are added, followed by the pre cooled peptide solution. The reaction mixture is stirred at 0° C. for 3 hours, then at room temperature overnight. The product is worked-up and purified using silica gel column chromatography and eluted with 70:30:3 chloroform/methanol/aqueous ammonia.

(d) [2-(S-3-Amino-2-Oxo-Pyrrolidin-1-yl)-S-2-Isopropylmethylacetyl]Arginyl(Tos)-Prolylethylamide Boc-[2-(S-3-amino-2-oxo-pyrrolidin-1-yl)-S-2-isopropylmethylacetyl]arginyl(Tos)-prolylethylamide, obtained from the previous reaction, is dissolved at 0° C. in trifluoroacetic acid (60 ml) containing 1.5% anisole and 1% dimethylphosphite. The solution is then stirred at room temperature for 30 minutes, and then concentrated in vacuo. The residue is washed twice with ether and dried over P₂O₅ to give [2-(S-3-amino-2-oxo-pyrrolidin-1-yl)-S-2-isopropylmethylacetyl]arginyl-(Tos)-prolylethylamide.

(e)
Cbz-(pyro)Glu-His(Cbz)Trp-N-Me-Ser(OBzl)-Tyr-(O-2-Br-Cbz)-NHNH₂

Cbz-(pyro)Glu-His(Cbz)-Trp-N-Me-Ser(OBzl)-Tyr-(O-2-Br-Cbz)-O-Resin is synthesized using the solid phase method described in Example 1, but starting with Boc-Tyr(O-2-Br-Cbz)-O-Resin (Merrifield resin), deblocking and coupling in a sequential order with the protected amino acids: Boc-N-Me-Ser(OBzl), Boc-Trp(N-formyl), Boc-His(Cbz), and Cbz-(pyro)Glu. The obtained Cbz-(pyro)Glu-His(Cbz)-Trp(N-formyl)-N-Me-Ser(OBzl)-Tyr(O-Br-Cbz)-O-Resin is treated with anhydrous hydrazine in 10% methanol solution at room temperature for 48 hours. The resin is filtered and the filtrate is concentrated in vacuo. The residue is triturated with ether and dried over P₂O₅ to give Cbz-(pyro)Glu-His(Cbz)-Trp-N-Me-Ser(OBzl)-Tyr(2-Br-Cbz)-NHNH₂.

(f)
Cbz-(pyro)Glu-His(Cbz)-Trp-N-Me-Ser(OBzl)-Tyr(2-Br-Cbz)-6,7-[2-(S-3-amino-2-oxo-pyrrolidin-1-yl)-S-2-isopropylmethylacetyl]-Arg(Tos)-Pro-NHEt 2.6 mmole of the hydrazide Cbz-(pyro)Glu-His(Cbz)-Trp-N-Me-Ser(OBzl)-Tyr(O-2-Br-Cbz)-NHNH₂ is dissolved in 26 ml of degassed DMF and cooled to $-10°$ C. under nitrogen. To the solution is added 2.4 ml of 5.8M hydrochloric acid/THF. The reaction mixture is cooled to $-25°$ C. and to it is added a (1:19) solution of isoamylnitrite/DMF until a positive starch/KI test reaction is obtained. About 16 ml of solution is required. When TLC shows that no hydrazide remained, the reaction mixture in cooled to $-40°$ C. and to it is added a cold DMF solution (4 ml) of [2-(S-3-amino-2-oxo-pyrrolidin-1-yl)-S-2-isopropylmethylacetyl]-arginyl(Tos)-prolylethylamide, previously obtained. The pH is raised to 8 with triethylamine. The reaction is stirred at $-20°$ C. for 24 hrs., after which the pH is readjusted to pH 8. Additional peptide is added and the reaction is stirred for additional 24 hrs. at the same temperature. The reaction mixture is concentrated in vacuo. The residue is triturated with water. The solid is filtered and dried over P₂O₅ to give Cbz-(pyro)Glu-His(Cbz)-Trp-N-Me-Ser(OBzl)-Tyr(O-2-Br-Cbz)-6,7-[2-(S-3-amino-2-oxo-pyrrolidin-1-yl)-S-2-isopropylmethylacetyl]-Arg(Tos)-Pro-NHEt.

(g)
(pyro)Glu-His-Trp-N-Me-Ser-Tyr-6,7-[2-(S-3-amino-2-oxo-pyrrolidin-1-yl)-S-2-isopropylmethylacetyl]-Arg-Pro-NHEt Cbz-(pyro)Glu-His(Cbz)-Trp-N-Me-Ser(OBzl)-Tyr-(O-2-Br-Cbz)-6,7-[2-(S-3-amino-2-oxo-pyrrolidin-1-yl)-S-2-isopropylmethylacetyl]-Arg(Tos)-Pro-NHEt, obtained from the previous experiment, is treated at 0° C. for 1 hour with anhydrous hydrogen fluoride (10 ml) in the presence of anisole (1.5 ml) and dimethylphosphite (1 ml). The excess reagents are removed in vacuo. The residue is washed three times with ether, then dissolved in (1:1)-water-acetonitrile solution (3.0 ml) and lyophilized. The crude product is purified by HPLC to give (pyro)Glu-His-Trp-N-Me-Ser-Tyr-6,7-[2-(S-3-amino-2-oxo-pyrrolidin-1-yl)-S-2-isopropylmethyl-acetyl]-Arg-Pro-NHEt.

EXAMPLE 14

N-AcSar-His-Trp-N-Me-Ser-Tyr-D-Trp-Leu-Arg-Pro-NHEt

N-AcSar-His-Trp-N-Me-Ser-Tyr-D-Trp-Leu-Arg-Pro-NHEt was synthesized using the instrument and the method described in Example 1, but substituting (pyro)-Glu with N-AcSar and Boc-D-Leu with Boc-D-Trp-(N-Formyl). The crude product was purified using high performance liquid chromatography on a 25 cm×2.5 cm Dynamax C-18 column (25–40 micron) using solvent mixtures in a gradient ranging from 89% H₂O/11% CH₃CN/0.1% TFA to 49% H₂O/51% CH₃CN/0.1% TFA over a period of 50 min. The flow rate is 15 ml/min. and UV detection is at 260 nM. The product was eluted at 17.59 minutes as a single peak, collected, and lyophilized to give pure (pyro)Glu-His-Trp-N-Me-Ser-Tyr-D-Trp-Leu-Arg-Pro-NHEt as the trifluoroacetate salt. Fab Mass spec. m/e 1298 (M+H)⁺. Amino Acid Anal.: 1.0 Pro, 1.1 Arg, 1.1 Leu, 1.6 Trp, 1.0 Tyr, 0.9 His.

EXAMPLE 15

(pyro)Glu-His-Trp-N-Me-Ser-Tyr-D-Trp-Leu-Arg-Pro-NHEt (pyro)Glu-His-Trp-N-Me-Ser-Tyr-D-Trp-Leu-Arg-Pro-NHEt was synthesized using the instrument and the method described in Example 1, but substituting Boc-D-Leu with Boc-D-Trp-(N-Formyl). The crude product was purified using high performance liquid chromatography according to the conditions described above. The product was eluted at 33.7 minutes as a single peak, collected, and lyophilized to give pure (pyro)Glu-His-Trp-N-Me-Ser-Tyr-D-Trp-Leu-Arg-Pro-NHEt as the trifluoroacetate salt. Fab Mass spec. m/e 1296 (M+H)⁺. Amino Acid Anal.: 1.1 Pro, 1.0 Arg, 1.0 Leu, 1.6 Trp, 1.0 Tyr, 1.0 His, 0.8 Glu.

EXAMPLE 16

N-AcSar-His-Trp-N-Me-Ser-Tyr-D-2-Nal-Leu-Arg-Pro-Gly-NH₂

N-AcSar-His-Trp-N-Me-Ser-Tyr-D-2-Nal-Leu-Arg-Pro-Gly-NH₂ was synthesized using the instrument and the method described in Example 3, but substituting Cbz-(pyro)Glu with N-AcSar. The crude product was purified using high performance liquid chromatography according to the conditions described above. The product was eluted at 24.5 minutes as a single peak, collected, and lyophilized to give pure N-AcSar-His-Trp-N-Me-Ser-Tyr-D-2-Nal-Leu-Arg-Pro-Gly-NH₂ as the trifluoroacetate salt. Fab Mass spec. m/e 1338 (M+H)⁺. Amino Acid Anal.: 1.0 Gly, 1.1 Pro, 0.9 Arg, 1.0 Leu, 1.0 Tyr, 0.8 Trp, 0.8 His.

EXAMPLE 17

N-Ac-D-4-Cl-Phe-D-4-Cl-Phe-D-Trp-N-Me-Ser-Tyr-D-Trp-Leu-Arg-Pro-D-Ala-NH₂

D-4-Cl-Phe-D-4-Cl-Phe-D-Trp-N-Me-Ser-Tyr-D-Trp-Leu-Arg-Pro-D-Ala-NH₂ can be synthesized using the instrument and the method described in Example 3, but substituting Cbz-(pyro)Glu and Boc-His-N-im-Cbz with Boc-D-4-Cl-Phe, substituting Boc-Trp(N-indole-formyl) and Boc-D-2-Nal with Boc-D-Trp(N-indole-formyl), and substituting Boc-Gly-O-Resin with Boc-D-Ala-O-Resin, removing the BOC group from the peptide-resin with TFA and acylating the N-terminus using acetylimidazole. The protected peptide is cleaved from the resin with anhydrous ammonia. Subsequently the protecting groups are cleaved upon treatment with liquid HF at 0° C. for 1 hour in the presence of anisole and dimethylphosphite. The crude product is purified using high performance liquid chromatgraphy to give N-Ac-D-4-Cl-Phe-D-4-Cl-Phe-D-Trp-N-Me-Ser-Tyr-D-Trp-Leu-Arg-Pro-D-AlaNH$_2$.

EXAMPLE 18

Using the method described in Example 17 and substituting with the appropriate amino acids, the following compounds can be synthesized:

N-Acetyl-3,4-dehydro-prolyl-D-3-4-Cl-phenylalanyl-D-tryptyl-N-methyl-seryl-tyrosyl-D-tryptyl-leucyl-arginyl-prolyl-D-alanylamide;

N-Acetyl-(delta)$^{3,4}$-prolyl-D-3-4-F-phenylalanyl-D-2-naphthylalanyl-N-methyl-seryl-tyrosyl-D-2-naphthylalanyl-leucyl-arginyl-prolyl-D-alanylamide;

N-Acetyl-D-3-4-Cl-phenylalanyl-D-2-naphthylalanyl-D-tryptyl-N-methyl-seryl-tyrosyl-D-arginyl-leucyl-arginyl-prolyl-D-alanylamide;

N-Acetyl-D-3-4-Cl-phenylalanyl-D-phenylalanyl-D-1-naphthylalanyl-N-methyl-seryl-tyrosyl-D-3-pyridyl-alanyl-N-methyl-leucyl-arginyl-prolyl-D-alanylamide.

N-Acetylprolyl-D-3-4-Cl-phenylalanyl-D-tryptyl-N-methyl-seryl-tyrosyl-D-2-naphthylalanyl-cyclohexylalanyl-lysyl(N-epsilon-isopropyl)-prolyl-D-alanylamide.

EXAMPLE 19

(pyro)Glu-N-Me-Phe-Trp-Ser-Tyr-D-Trp-Leu-Arg-ProNHEt

Using the same procedure and protocol described in Example 1 but substituting BOC-N-Me-Phe for BOC-His(N-im-CBZ), BOC-D-Trp(N-indole-formyl) for BOC-D-Leu, BOC-Ser(OBzl) for BOC-N-Me-Ser-(OBzl) and adding 0.1% DMAP to the solution of Cbz-p-Glu instead of that of BOC-Trp(N-indole formyl), and following the same workup as previously described, (pyro)Glu-N-Me-Phe-Trp-Ser-Tyr-D-Trp-Leu-Arg-ProNHEt was obtained as crude product. The compound was purified by HPLC as previously described. The product was eluted at 27.3 minutes as a single peak. Fab Mass spec. m/e 1306 (M+H)$^+$. Amino Acid Anal.: 1.0 Pro, 1.1 Arg, 1.0 Leu, 1.6 Trp, 0.9 Tyr, 0.7 Ser, 0.9 Glu.

EXAMPLE 20

(pyro)Glu-His-Trp-Ser-N-Me-Tyr-D-Trp-Leu-Arg-ProNHEt

Using the same procedure and protocol described in Example 1 but substituting BOC-D-Trp(N-indole-formyl) for BOC-D-Leu, BOC-Ser(OBzl) for BOC-N-Me-Ser(OBzl), BOC-N-Me-Tyr(O-2,6-di-Cl-Bzl) for BOC-Tyr(O-Br-CBz), and adding 0.1% DMAP to the solution of BOC-Ser-(OBzl) instead of that of BOC-Trp(N-indole-formyl), and following the same workup as previously described, (pyro)Glu-His-Trp-Ser-N-Me-Tyr-D-Trp-Leu-Arg-ProNHEt was obtained as a crude product. The compound was purified by HPLC as previously described. The product was eluted at 25.15 minutes as a single peak. Fab Mass spec. m/e 1296 (M+H)$^+$. Amino Acid Anal.: 1.1 Pro, 1.2 Arg, 1.1 Leu, 1.3 Trp, 0.7 Ser, 0.9 His, 0.9 Glu.

EXAMPLE 21

(pyro)Glu-His-Trp-Ser-N-Me-Tyr-D-Leu-Leu-Arg-ProNHEt

Using the same procedure and protocol described in Example 20 but substituting BOC-D-Leu for BOC-D-Trp(N-indole-formyl), and following the same workup as previously described, (pyro)Glu-His-Trp-Ser-N-Me-Tyr-D-Leu-Leu-Arg-ProNHEt was obtained as a crude product. The compound was purified by HPLC as previously described. The product was eluted at 16.8 minutes as a single peak. Fab Mass spec. m/e 1223 (M+H)$^+$. Amino Acid Anal.: 1.0 Pro, 0.9 Arg, 1.5 Leu, 0.6 Ser, 0.9 Trp, 0.8 His, 0.8 Glu.

EXAMPLE 22

(pyro)Glu-His-Trp-Ser-Tyr-N-Me-D-Leu-Leu-Arg-ProNHEt

Using the same procedure and protocol described in Example 1 but substituting BOC-Ser(OBzl) for BOC-N-Me-Ser(OBzl), BOC-N-Me-D-Leu for BOC-D-Leu and adding 0.1% DMAP to the solution of BOC-Tyr(O-Br-Cbz) instead of that of BOC-Trp(N-indole-formyl), and following the same workup as previously described, (pyro)Glu-His-Trp-Ser-Tyr-N-Me-D-Leu-Leu-Arg-ProNHEt was obtained as a crude product. The compound was purified by HPLC as previously described. The product was eluted at 34.3 minutes, as a single peak. Fab Mass spec. m/e 1223 (M+H)$^+$. Amino Acid Anal.: 1.0 Pro, 0.9 Arg, 0.8 Leu, 0.8 Tyr, 0.7 Ser, 0.7 Trp, 0.9 His, 0.9 Glu.

EXAMPLE 23

(pyro)Glu-His-Trp-Ser-Tyr-D-Trp-Leu-N-Me-Arg-ProNHEt

Using the same procedure described in Example 1 but substituting BOC-Ser(OBzl) for BOC-N-Me-Ser(OBzl), BOC-D-Trp(N-indole-formyl) for BOC-D-Leu, BOC-N-Me-Arg(Tos) for BOC-Arg(Tos) and adding 0.1% DMAP to the solution of BOC-Leu instead of that of BOC-Trp(N-indole-formyl), and following the same workup as previously described, (pyro)Glu-His-Trp-Ser-Tyr-D-Trp-Leu-N-Me-Arg-ProNHEt was obtained as a crude product. The compound was purified by HPLC using the same conditions previously described. The product was eluted at 18 minutes as a single peak. Fab Mass Spec. m/e 1296 (M+H)$^+$. Amino Acid Anal.: 0.95 Pro; 1.08 Leu; 2.16 Trp; 1.09 Ser; 1.00 His; 0.88 Glu.

EXAMPLE 24

(pyro)Glu-His-N-Me-Trp-Ser-Tyr-D-Trp-Leu-Arg-ProNHEt

Using the same procedure described in Example 1 but substituting BOC-Ser(OBzl) for BOC-N-Me-Ser(OBzl), BOC-N-Me-Trp(N-indole-formyl) for BOC-Trp(N-indole-formyl), BOC-D-Trp(N-indole-formyl) for BOC-D-Leu, and adding 0.1% DMAP to the solution of BOC-His(N-im-CBZ), and following the same workup as previously described, (pyro)Glu-His-N-Me-Trp-Ser-Tyr-D-Leu-Arg-ProNHEt can be obtained and subsequently purified by HPLC using the same conditions previously described.

EXAMPLE 25

(pyro)Glu-His-N-Me-1-Nal-Ser-Tyr-D-Trp-N-Me-Leu-Arg-ProNHEt

Using the same procedure described in Example 1 but substituting BOC-Ser(OBzl) for BOC-N-Me-Ser(OBzl), BOC-N-Me-1-Nal for BOC-Trp(N-indole-formyl), BOC-D-Trp(N-indole-formyl) for BOC-D-Leu, BOC-N-Me-Leu for BOC-Leu, and adding 0.1% DMAP to the solutions of BOC(N-im-CBZ) His and BOC-D-Trp(N-indole-formyl) instead of that of BOC-Trp(N-indole-formyl), (pyro)Glu-His-N-Me-1-Nal-Ser-Tyr-D-Trp-N-Me-Leu-Arg-ProNHEt can be obtained and subsequently purified by HPLC using the same conditions previously described.

EXAMPLE 26

N-Ac-3,4-dehydro-Pro-4-Cl-D-Phe-D-Trp-Ser-N-Me-Tyr-D-Trp-Leu-Arg Pro-D-AlaNH$_2$ Using the same procedure and protocol described in Example 1, but substituting BOC-Pro-O-Resin (Merrifield resin) with BOC-D-Ala-NH-Resin (4-methyl-benzhydrylamine resin), CBZ-(pyro)-Glu with N-Ac-Pro, BOC-His(N-im-CBz) with BOC-4-Cl-D-Phe, BOC-Trp(N-indole-formyl) and BOC-D-Leu with BOC-D-Trp(N-indole formyl), BOC-Tyr(O-2 Br-CBZ) with BOC-N-Me-Tyr(O-2,6-di-Cl-Bzl) and adding 0.1% DMAP to the solution of BOC-Ser(OBzl) instead of that of BOC-Trp(N-indole-formyl) and acylating the N-terminus of the peptide on the resin using N-acetylimidazole, the peptide resin N-Ac-3,4-dehydro-Pro-4-Cl-D-Phe-D-Trp-Ser(OBzl)-N-Me-Tyr-(O-2,6-di-Cl-Bzl)-D-Trp(N-indole-formyl)-Leu-Arg(Tos)-Pro-D-Ala-NH-Resin can be obtained. The peptide is cleaved from the resin upon treatment with HF at 0° C. for 1 h in the presence of 5% anisole and 5% dimethyl phosphite. After work up and HPLC purification, N-Ac-3,4-dehydro-Pro-4-Cl-D-Phe-D-Trp-Ser-N-Me-Tyr-D-Trp-Leu-Arg-Pro-D-AlaNH$_2$ can be obtained.

EXAMPLE 27

N-Ac-Sar-Phe-Trp-N-Me-Ser-Tyr-D-Trp-Leu-Arg-Pro-SarNH$_2$

Using same procedure and protocol described in Example 26, but substituting BOC-D-AlaNH Resin with BOC-Sar-NH-Resin (4-methyl-benzhydrylamine resin), N-Ac-3,4-dehydro-Pro with CBZ-p-Glu, BOC-4-Cl-D-Phe with BOC-Phe, BOC-D-Trp(N-indole-formyl) at position 3 with BOC-Trp(N-indole-formyl), BOC-Ser-(OBzl) with BOC-N-Me-Ser(OBzl) and adding 0.1% DMAP to the solutions of BOC-Trp-(N-indole-formyl) and BOC-Pro, after HF cleavage, work-up and HPLC purification, N-Ac-Sar-Phe-Trp-N-Me-Ser-Tyr-D-Trp-Leu-Arg-Pro-SarNH$_2$ can be obtained.

EXAMPLE 28

N-Ac-Sar-N-Me-His-Trp-Ser-N-Me-Tyr-D-Tyr-Leu-Arg-Pro-NHEt

Using the same protocol and procedure described in Example 1 but substituting BOC-N-Me-His(N-im-CBZ) for BOC-His(N-im-CBZ), BOC-Ser-(OBzl) for BOC-N-Me-Ser(OBzl), BOC-N-Me-Tyr(O-2,6-di-Cl-Bzl) for BOC-Tyr(O-2-Br-CBZ), BOC-D-Tyr(O-2-Br Cbz) for BOC-D-Leu and adding 0.1% DMAP to the solutions of N-Ac-Sar and BOC-Ser(OBzl) instead of that of BOC-Trp(N-indole-formyl), after work-up and HPLC purification, (pyro)Glu-N-Me-His-Trp-Ser-N-Me-Tyr-D-Tyr-Leu-Arg-ProNHEt can be obtained.

EXAMPLE 29

N-Ac-3,4-dehydro-Pro-D-4-Cl-Phe-D-Trp-Ser-N-Me-Tyr-D-Arg-N-Me-Leu-Arg-Pro-D-AlaNH$_2$ Using the same procedure described in Example 26, but substituting the BOC-D-Trp-(N-indole-formyl) at position 6 with BOC-D-Arg(Tos), BOC-Leu with BOC-N-Me-Leu, and adding 0.1% of DMAP to the solution of BOC-D-Arg(Tos) also, after work-up and HPLC purification, N-Ac-3,4-dehydro-Pro-D-4-Cl-Phe-D-Trp-Ser-N-Me-Tyr-D-Arg-N-Me-Leu-Arg-Pro-D-AlaNH$_2$ can be obtained.

EXAMPLE 30

(pyro)Glu-N-Me-Phe-Trp-Ser-N-Me-Tyr-D-Trp-Leu-Arg-Pro-SarNH$_2$

Using the same protocol and procedure described in Example 27 but substituting BOC-N-Me-Phe for BOC-Phe, BOC-Ser(OBzl) for BOC-N-Me-Ser(OBzl), BOC-N-Me-Tyr(O-2,6-di-Cl-Bzl) for BOC-Tyr(O-2-Br-CBZ), and adding 0.1% of DMAP to the solutions of CBZ-(pyro)Glu, BOC-Ser(OBzl) and BOC-Pro, instead of that of BOC-Trp(N-indole-formyl), following HF cleavage, work-up and HPLC purification, (pyro)Glu-N-Me-Phe-Trp-Ser-N-Me-Tyr-D-Trp-Leu-Arg-Pro-SarNH$_2$ can be obtained.

EXAMPLE 31

N-Ac-Sar-His-Trp-N-Me-Ser-N-Me-Tyr-D-Trp-Leu-Arg-ProNHEt

Using the same protocol and procedure described in Example 1 but substituting N-Ac-Sar for CBZ-(pyro)-Glu, BOC-N-Me-Tyr(O-2,6-di-Cl-Bzl) for BOC-Tyr(O-2-Br-CBZ), BOC-D-Trp(N-indole-formyl) for BOC-D-Leu, and adding 0.1% DMAP to the BOC-N-Me-Ser-(OBzl) solution also, after work up and HPLC purification, N-Ac-Sar-His-Trp-N-Me-Ser-N-Me-Tyr-D-Trp-Leu-Arg-ProNHEt can be obtained.

EXAMPLE 32

N-Ac-Sar-3-Tic-Trp-Ser-N-Me-Tyr-D-Trp-N-Me-Leu-Leu-Arg-ProNHEt

Using the same protocol and procedure described in Example 21 but substituting N-Ac-Sar for Cbz-(pyro)-Glu, BOC-3-Tic for BOC-His(N-im-CBZ), BOC-D-Trp(N-indole-formyl) for BOC-D-Leu, BOC-N-Me-Leu for BOC-Leu, and adding 0.1% DMAP to the solution of BOC-D-Trp(N-indole-formyl) also, after workup and HPLC purification, N-Ac-Sar-3-Tic-Trp-Ser-N-Me-Tyr-D-Trp-N-Me-Leu-Leu-Arg-ProNHEt can be obtained.

EXAMPLE 33

N-Ac-D-2-Nal-N-Me-D-4-Cl-Phe-D-3-Pal-Ser-Lys(epsilon-N-nicotinyl)-D-Lys(N-epsilon-nicotinyl)-Leu-Lys(N-epsilon-isopropyl)-Pro-D-AlaNH$_2$ Using a procedure and a synthetic protocol similar to those described in Example 1 but substituting BOC-D-Ala-NH-Resin (4-methyl-benzhydrylamine resin) for BOC-Pro-O-Resin (Merrifield resin) and coupling the amino acids according to the following order and coupling protocol:

| # | Amino Acid | Coupling |
|---|---|---|
| 1. | BOC—Pro | two-1 h |
| 2. | BOC—Lys(N-epsilon-isopropyl-N-epsilon-CBZ) | two-1 h |
| 3. | BOC—Leu | two-1 h |
| 4. | BOC-D-Lys(N-epsilon-FMOC) | two-1 h |
| 5. | BOC—Lys(N-epsilon-FMOC) | two-1 h |
| 6. | BOC-3-D-Pal | two-6 h |
| 7. | BOC—N—Me-D-4-Cl—Phe | two-6 h |
| 8. | N-Ac-D-2-Nal with or without 0.1% DMAP | two-6 h |

Upon completion of the synthesis the resin is treated with 20% piperidine in $CH_2Cl_2$/DMF solution overnight to remove the FMOC protecting groups from the two Lys. After several washes with $CH_2Cl_2$ and drying in vacuo, the peptide on the resin is coupled with nicotinic acid using the peptide synthesizer and the two-1h coupling protocol. Subsequently the peptide is cleaved from the resin with HF at 0° C. for 1 h in the presence of anisole and dimethylphosphite to give N-Ac-D-2-Nal-N-Me-D-4-Cl-Phe-3-Pal-Ser-Lys-(N-epsilon-nicotinyl)-D-Lys-(N-epsilon-nicotinyl)-Leu-Lys(N-epsilon-isopropyl)-Pro-D-AlaNH$_2$ as a crude product. The peptide can be purified by HPLC using the conditions previously described.

EXAMPLE 34

N-Ac-D-2-Nal-N-Me-D-4-Cl-Phe-D-3-Pal-Ser-Lys(N-epsilon-nicotinyl)-D-Lys(N-epsilon-nicotinyl)-Leu-Lys-(N-epsilon-isopropyl)-Pro-SarNH$_2$ Using the same procedure, protocol, and amino acids as described in Example 33 but substituting BOC-Sar-NH-Resin (4-methyl-benzydrylamine resin) for BOC-D-Ala-NH-Resin and also adding 0.1% DMAP to the solution of BOC-Pro, after work up and HPLC purification, N-Ac-D-2-Nal-N-Me-D-4-Cl-Phe-D-3-Pal-Ser-Lys-(N-epsilon-nicotinyl)-D-Lys-(N-epsilon-nicotinyl)-Leu-Lys-(N-epsilon-isopropyl)-Pro-SarNH$_2$ can be obtained.

EXAMPLE 35

N-Ac-D-2-Nal-D-4-Cl-Phe-D-3-Pal-N-Me-Ser-Lys-(N-epsilon-nicotinyl)-D-Lys-(N-epsilon-nicotinyl)-Leu-Lys-(N-epsilon-isopropyl)-Pro-D-AlaNH$_2$ Using the same procedure, protocol and amino acids as described in Example 33, but substituting BOC-D-4-Cl-Phe for BOC-N-Me-D-4-Cl-Phe, BOC-N-Me-Ser-(OBzl) for BOC-Ser(OBzl) and adding 0.1% DMAP only to the solution of BOC-Pal, following workup and HPLC purification. N-Ac-D2-Nal-D-4-Cl-Phe-D-3-Pal-N-Me-Ser-Lys(N-epsilon-nictinoyl)-D-Lys(N-epsilon-nicotinyl)-Leu-Lys(N-epsilon-isopropyl)-Pro-D-AlaNH$_2$ was obtained as the trifluoroacetate salt; $R_T$=16.3 min. Mass spec. m/e 1605 (M+H)$^+$. Amino Acid Anal.: 0.9 Ala; 1.12 Pro; 2.06 Lys; 0.94 Leu.

EXAMPLE 36

N-Ac-D-2-Nal-D-4-Cl-Phe-D-3-Pal-Ser-N-Me-Tyr-D-Lys-(N-epsilon-2-picolinyl)-Leu-Lys-(N-epsilon-isopropyl)-Pro-D-AlaNH$_2$ Using the same procedure, protocol and amino acids as described in Example 33, but substituting BOC-N-Me-Tyr(O-2,6-diCl-Bzl) for BOC-Lys-(N-epsilon-FMOC), adding 0.1% DMAP only to the DMF solution of BOC-Ser(OBzl), and at the end coupling with picolinic acid instead of nicotinic acid. Following workup and HPLC purification, the desired compound can be obtained.

EXAMPLE 37

N-Ac-D-2-Nal-D-4-Cl-Phe-D-3-Pal-N-Me-Scr-Tyr-D-Lys-(N-epsilon-6-methyl-nicotinyl)-Leu-Lys-(N-epsilon-isopropyl)-Pro-D-AlaNH$_2$ Using the same procedure, protocol and amino acids described in Example 33, but substituting BOC-N-Me-Ser(OBzl) for BOC-Ser(O-Bzl), adding 0.1% DMAP only to the DMF solution of BOC-D-3-Pal and at the end coupling with 6-methylnicotinic acid instead of nicotinic acid, following workup and HPLC purification, the desired compound can be obtained.

EXAMPLE 38

N-Ac-D-2-Nal-D-4-Cl-Phe-D-3-Pal-Ser-N-Me-Tyr-D-Lys(N-epsilon-nicotinyl)-Leu-Lys(N-epsilon-isopropyl)-Pro-D-AlaNH$_2$ The same procedure described in Example 33 was used, but substituting in the synthesis Boc-N-Me-Tyr-(O-2,6-diCl-Bzl) for Boc-Lys(N-epsilon-FMOC), 1 adding 0.1% DMAP only to the DMF solution of Boc-Ser-(OBzl) and substituting Boc-D-4-Cl-Phe for Boc-N-Me-D-4-Cl-Phe. After workup and HPLC purification, the title compound was obatined as the trifluoroacetate salt. $R_T$=24.9 min. Mass Spec. m/e 1535 (M+H)$^+$. Amino Acid Anal.: 0.97 Ala; 0.94 Pro; 1.04 Lys; 1.07 Leu; 0.46 Ser.

EXAMPLE 39

N-Ac-D-4-Cl-Phe-D-4-Cl-Phe-D-2-Thia-Ser-N-Me-Tyr-D-Lys-Leu-Arg-Pro-D-AlaNH$_2$

The procedure described in Example 20 was used, but starting with Boc-D-Ala-NH-Resin (benzhydrylamine resin) and substituting in the synthesis N-Ac-D-4-Cl-Phe for Cbz-pyro-Glu, Boc-D-4-Cl-Phe for Boc-His(Cbz), Boc-D-2-Thia for Boc-Trp(N-indole-formyl) and Boc-D-Lys(N-epsilon-Cbz) for Boc-D-Trp(N-indole-formyl). Boc-Pro was first coupled to the resin and 0.1% DMAP was added to the Boc-Ser(OBzl) solution. After HF treatment, workup and HPLC purification, the desired compound was obtained as the trifluoroacetate salt. $R_T$=26.46 min. Mass Spec. m/e 1406 (M+H)$^+$. Amino Acid Anal.: 0.95 Ala; 1.05 Pro; 1.00 Arg; 1.02 Leu; 0.98 Lys; 0.57 Ser.

EXAMPLE 40

N-Ac-D-4-Cl-Ph-D-4-Cl-Phe-D-2-Thia-N-Me-Ser-Tyr-D-Lys-Leu-Arg-Pro-D-AlaNH$_2$

The procedure described in Example 39 was used. The following substitutions were made: Boc-N-Me-Ser-(OBzl) for Boc-Ser(OBzl) and Boc-Tyr(O-2-Br-Cbz) for Boc-N-Me-Tyr(O-di-2,6-Cl-Bzl). 0.1 % DMAP was added to the solution of Boc-D-2-Thia. After HF treatment, workup and HPLC purification, the desired compound was obtained.

EXAMPLE 41

N-Ac-D-4-Cl-Phe-D-4-Cl-Phe-D-2-Thia-Ser-Tyr-D-Lys-Leu-N-Me-Arg-Pro-D-AlaNH$_2$

The procedure described in Example 39 was used, substituting Boc-Tyr(O-2-Br-Cbz) for Boc-N-Me-Tyr-(O-di-2,6-Cl-Cbz) and Boc-N-Me-Arg(tos) for Boc- Arg(tos). 0.1 % DMAP was added to the Boc-Leu solution. After HF treatment, workup and HPLC purification, the desired product was obtained.

EXAMPLE 42

N-Ac-Gly-D-4-Cl-Phe-D-3-Pal-Ser-N-Me-Tyr-D-Lys-(N-epsilon-nicotinyl)-Leu-Lys(N-epsilon-isopropyl)-Pro-D-AlaNH₂

The same procedure described in Example 38 was used, but substituting in the synthesis N-Ac-Gly for N-Ac-D-2-Dal. After HF treatment, workup, and HPLC purification N-Ac-Gly-D-4-Cl-Phe-D-3-Pal-Ser-N-Me-Tyr-D-Lys(N-epsilon-nicotinyl)-Leu-Lys(N-epsilon-isopropy)-Pro-D-AlaNH₂ was obtained as the trifluoroacetate salt; $R_T = 19.8$ min; Mass spec. m/e 1394 (M+H)+. Amino Acid Anal: 1.01 Ala; 1.13 Pro; 1.01 Leu; 1.01 Lys; 0.51 Ser; 0.98 Gly.

EXAMPLE 43

N-Ac-D-2-Nal-D-4-Cl-Phe-D-4-Thiaz-Ser-N-Me-Tyr-D-Lys-(N-epsilon-nicotinyl)-Leu-Lys(N-epsilon-isopropyl)-Pro-D-AlaNH₂

The same procedure described in Example 38 was used, but substituting in the synthesis Boc-D-3-(4-thiazolyl)alanyl for Boc-D-3-(3-pyridyl)alanyl. After HF treatment, workup, and HPLC purification N-Ac-D-2-Nal-D-4-Cl-Phe-D-4-Thiaz-Ser-N-Me-Tyr-D-Lys(N-epsilon-nicotinyl)-Leu-Lys-(N-epsilon-isopropyl)-Pro-D-AlaNH₂ was obtained as the trifluoroacetate salt; $R_T = 25.57$ min; Mass spec. m/e 1540 (M+H)+. Amino Acid Anal: 1.01 Ala; 1.15 Pro; 1.04 Leu; 0.95 Lys; 0.47 Ser.

EXAMPLE 44

N-Ac-D-2-Nal-D-4-Cl-Phe-D-3-Pal-Ser-N-Me-Tyr-D-Lys(N-epsilon-nicotinyl)-Leu-Lys(N-epsilon-isopropyl)-Pro-SarNH₂

The same proCedure described ln Example 38 was used, but substituting in the synthesis Boc-Sar-NH-Resin (4-methyl-benzhydrylamine resin) for Boc-DAla-NH-Resin (4-methyl-benzhydrylamine). After HF treatment, workup, and HPLC purification N-Ac-D-2-Nal-D-4-Cl-Phe-D-3-Pal-Ser-N-Me-Tyr-D-Lys(N-epsilon-nicotinyl)-Leu-Lys(N-epsilon-isopropyl)-Pro-SarNH₂ was obtained as a trifluoroacetate salt; $R_T = 34.48$ min; Mass spec. m/e 1534 (M+H)+. Amino Acid Anal: 1.12 Sar; 0.97 Pro; 1.03 Leu; 1.01 Lys; 0.49 Ser.

EXAMPLE 45

N-Ac-D-4-Cl-Phe-D-4-Cl-Phe-D-2-Thia-Ser-N-Me-Tyr-D-Lys-N-Me-Leu-Arg-Pro-D-AlaNH₄

The same procedure described in Example 39 was used, but substituting in the synthesis Boc-N-Me-Leu for Boc-Leu and adding 0.1% DMAP to the solution of Boc-D-Lys(N-epsilon-Cbz). After HF treatment, workup, and HPLC purification N-Ac-D-4-Cl-Phe-D-4-Cl-Phe-D-2-Thia-Ser-N-Me-Tyr-D-Lys-N-Me-Leu-Arg-Pro-D-AlaNH₂ was obtained as a trifluoroacetate salt; $R_T = 20.66$ min; Mass spec. m/e 1419 (M+H)+. Amino Acid Anal: 1.05 Ala; 0.97 Pro; 1.05 Arg; 0.99 Lys; 0.53 Ser.

EXAMPLE 46

N-Ac-D-4-Cl-Phe-D-4-Cl-Phe-D-1-Nal-Ser-N-Me-Tyr-D-Lys-Leu-Arg-Pro-D-AlaNH₂

The same procedure described in Example 39 was used, but substituting in the synthesis Boc-D-1-Nal for Boc-D-2-Thia. After HF treatment, workup, and HPLC purification N-Ac-D-4-Cl-Phe-D-4-Cl-Phe-D-1-Nal-Ser-N-Me-Tyr-D-Lys-Leu-Arg-Pro-D-AlaNH₂ was obtained as a trifluoroacetate salt; $R_T = 28.98$ min; Mass spec. m/e 1488 (M+H)+. Amino Acid Anal: 1.00 Ala; 1.00 Pro; 1.04 Arg; 1.05 Leu; 1.03 Lys; 0.62 Ser.

EXAMPLE 47

N-Ac-D-4-Cl-Phe-D-4-Cl-Phe-D-1-Nal-Ser-N-Me-Tyr-D-Lys-Cha-Arg-Pro-D-AlaNH₂

The same procedure described in Example 46 was used, but substituting in the synthesis Boc-Cha for Boc-Leu. After HF treatment, workup, and HPLC purification N-Ac-D-4-Cl-Phe-D-4-Cl-Phe-D-1-Nal-Ser-N-Me-Tyr-D-Lys-Cha-Arg-Pro-D-AlaNH₂ was obtained as the a trifluoroacetate salt; $R_T = 28.98$ min; Mass spec. m/e 1488 (M+H)+. Amino Acid Anal: 1.01 Ala; 1.00 Pro; 0.94 Arg; 0.85 Cha; 0.99 Lys; 0.59 Ser.

EXAMPLE 48

N-Ac-Sar-D-4-Cl-Phe-D-1-Nal-Ser-N-Me-Tyr-D-Lys-Leu-Arg-Pro-D-AlaNH₂

The same procedure described in Example 46 was used, but substituting in the synthesis N-Ac-Sar for N-Ac-D-4-Cl-Phe. After HF treatment, workup, and HPLC purification N-Ac-Sar-D-4-Cl-Phe-D-1-Nal-Ser-N-Me-Tyr-D-Lys-Leu-Arg-Pro-D-AlaNH₂ was obtained as a trifluoroacetate salt; $R_T = 28.80$ min; Mass spec. m/e 1338 (M+H)+. Amino Acid Anal: 1.01 Ala; 1.10 Pro; 0.99 Arg; 1.01 Leu; 0.99 Lys; 0.57 Ser.

EXAMPLE 49

N-Ac-Sar-D-4-Cl-Phe-D-2-Thia-Ser-N-Me-Tyr-D-Lys-Leu-Arg-Pro-D-AlaNH₂

The same procedure described in Example 48 was used, but substituting in the synthesis Boc-D-2-Thia for Boc-D-1-Nal. After HF treatment, workup, and HPLC purification N-Ac-Sar-D-4-Cl-Phe-D-2-Thia-Ser-N-Me-Tyr-D-Lys-Leu-Arg-Pro-D-AlaNH₂ was obtained as a trifluoroacetate salt; $R_T = 24.04$ min; Mass spec. m/e 1294 (M+H)+. Amino Acid Anal: 1.02 Ala; 1.10 Pro; 0.99 Arg; 0.85 Leu; 0.99 Lys; 0.52 Ser.

EXAMPLE 50

N-Ac-Sar-D-4-Cl-Phe-D-1-Nal-Ser-N-Me-Tyr-D-3-Pal-Leu-Arg-Pro-D-AlaNH₄

The same procedure described in Example 48 was used, but substituting in the synthesis Boc-D-3-Pal for Boc-D-Lys(N-epsilon-Cbz). After HF treatment, workup, and HPLC purification N-Ac-Sar-D-4-Cl-Phe-D-1-Nal-Ser-N-Me-Tyr-D-3-Pal-Leu-Arg-Pro-D-AlaNH₂ was obtained as a trifluoroacetate salt; $R_T = 24.81$ min; Mass spec. m/e 1358 (M+H)+. Amino Acid Anal: 0.98 Ala; 1.02 Pro; 0.99 Arg; 1.01 Leu; 0.57 Ser.

EXAMPLE 51

N-Ac-Sar-D-4-Cl-Phe-D-1-Nal-Ser-N-Me-Tyr-D-Tys(N-epsilon-nicotinyl)-Leu-Arg-Pro-D-AlaNH$_2$ The same procedure described in Example 38 was used, but substituting in the synthesis N-Ac-Sar for N-Ac-D-2-Nal, Boc-D-1-Nal for Boc-D-3-Pal, and Boc-Arg(Tos) for Boc-Lys(N,N-epsilon-isopropyl,Cbz). After HF treatment, workup, and HPLC purification N-Ac-Sar-D-4-Cl-Phe-D-1-Nal-Ser-N-Me-Tyr-D-Lys(N-epsilon-nicotinyl)-Leu-Arg-Pro-D-AlaNH$_2$ was obtained as a trifluoroacetate salt; $R_T$=20.72 min; Mass spec. m/e 1443 (M+H)$^+$. Amino Acid Anal: 0.97 Ala; 1.09 Pro; 1.01 Arg; 1.06 Leu; 0.94 Lys; 0.49 Ser.

EXAMPLE 52

N-Ac-Sar-D-4-Cl-Phe-1-Nal-Ser-N-Me-Tyr-D-Lys-Leu-Arg-Pro-D-AlaNH$_4$

The same procedure described in Example 48 was used, but substituting in the synthesis Boc-1-Nal for Boc-D-1-Nal. After HF treatment, workup, and HPLC purification N-Ac-Sar-D-4-Cl-Phe-1-Nal-Ser-N-Me-Tyr-D-Lys-Leu-Arg-Pro-D-AlaNH$_2$ was obtained as a trifluoroacetate salt; $R_T$=29.20 min; Mass spec. m/e 1338 (M+H)$^+$. Amino Acid Anal: 1.02 Ala; 1.12 Pro; 0.99 Leu; 0.98 Lys; 0.49 Ser.

EXAMPLE 53

N-Ac-Gly-D-4-Cl-Phe-D-1-Nal-Ser-N-Me-Tyr-D-Lys-Leu-Arg-Pro-D-AlaNH$_2$

The same procedure described in Example 48 was used, but substituting N-Ac-Gly for N-Ac-Sar. After HF treatment, workup, and HPLC purification N-Ac-Gly-D-4-Cl-Phe-D-1-Nal-Ser-N-Me-Tyr-D-Lys-Leu-Arg-Pro-D-AlaNH$_2$ was obtained as a trifluoroacetate salt; $R_T$=21.93 min; Mass spec. m/e 1324 (M+H)$^+$. Amino Acid Anal: 1.01 Ala; 1.09 Pro; 0.99 Arg; 1.03 Leu; 0.56 Ser; 0.95 Gly.

EXAMPLE 54

N-Ac-D-4-Cl-Phe-D-4-Cl-Phe-D-3-Bal-Ser-N-Me-Tyr-D-Lys-Leu-Arg-Pro-D-AlaNH$_2$

The same procedure described in Example 39 was used, but substituting in the synthesis Boc-D-3-Bal for Boc-D-2-Thia. After HF treatment, workup, and HPLC purification N-Ac-D-4-Cl-Phe-D-4-Cl-Phe-D-3-Bal-Ser-N-Me-Tyr-D-Lys-Leu-Arg-Pro-D-AlaNH$_2$ was obtained as a trifluoroacetate salt; $R_T$=27.9 min; Mass spec. m/e 1454 (M+H)$^+$. Amino Acid Anal: 0.97 Ala; 1.07 Pro; 1.00 Arg; 1.02 Leu; 1.00 Lys; 0.55 Ser.

EXAMPLE 55

N-Ac-D-4-Cl-Phe-D-4-Cl-Phe-D-Trp(formyl)-Ser-N-Me-Tyr-D-Lys-Leu-Arg-Pro-D-AlaNH$_2$ The same procedure described in Example 39 was used, but substituting in the synthesis Boc-D-Trp(formyl) for Boc-D-2-Thia. After HF treatment, workup, and HPLC purification N-Ac-D-4-Cl-Phe-D-4-Cl-Phe-D-Trp(formyl)-Ser-N-Me-Tyr-D-Lys-Leu-Arg-Pro-D-AlaNH$_2$ was obtained as a trifluoroacetate salt; $R_T$=39.96 min; Mass spec. m/e 1465 (M+H)$^+$. Amino Acid Anal: 1.01 Ala; 0.78 Pro; 0.97 Arg; 1.02 Leu; 1.01 Lys; 0.48 Ser; 0.59 Trp.

EXAMPLE 56

N-Ac-D-4-Cl-Phe-D-4-Cl-Phe-N-Me-D-1-Nal-Ser-N-Me-Tyr-D-Lys-Leu-Arg-Pro-D-AlaNH$_2$

The same procedure described in Example 39 was used, but substituting in the synthesis Boc-N-Me-D-1-Nal for Boc-D-2-Thia and adding 0.1% DMAP to the solution of Boc-D-4-Cl-Phe. After HF treatment, workup, and HPLC purification N-Ac-D-4-Cl-Phe-D-4-Cl-Phe-N-Me-D-1-Nal-Ser-N-Me-Tyr-D-Lys-Leu-Arg-Pro-D-AlaNH$_2$ was obtained as a trifluoroacetate salt; $R_T$=24.86 min; Mass spec. m/e 1462 (M+H)$^+$. Amino Acid Anal: 1.06 Ala; 1.10 Pro; 1.00 Arg; 1.00 Leu; 0.98 Lys; 0.57 Ser.

EXAMPLE 57

N-Ac-D-4-Cl-Phe-D-4-Cl-Phe-D-2-Nal-Ser-N-Me-Tyr-D-Lys(N-epsilon-nicotinyl)-N-Me-Leu-Arg-Pro-D-AlaNH$_2$ The same procedure described in Example 38 was used, but substituting in the synthesis N-Ac-D-4-Cl-Phe for N-Ac-D-2-Nal, Boc-D-2-Nal for Boc-D-3-Pal, Boc-N-Me-Leu for Boc-Leu, and Boc-Arg(Tos) for Boc-Lys(N,N-epsilon-isopropyl,Cbz). After HF treatment, workup, and HPLC purification N-Ac-D-4-Cl-Phe-D-4-Cl-Phe-D-2-Nal-Ser-N-Me-Tyr-D-Lys(N-epsilon-nicotinyl)-N-Me-Leu-Arg-Pro-D-AlaNH$_2$ was obtained as a trifluoroacetate salt; $R_T$=29.05 min; Mass spec. m/e 1567 (M+H)$^+$. Amino Acid Anal: 0.97 Ala; 1.09 Pro; 1.03 Arg; 1.00 Lys; 0.46 Ser.

EXAMPLE 58

N-Ac-D-4-Cl-Phe-D-4-Cl-Phe-D-2-Thia-Ser-Tyr-D-Lys-Leu-Arg-Pro-SarNH$_2$

The same procedure described for Example 39 was used, but substituting Boc-Tyr(O-2-Br-Cbz) for Boc-N-Me-Tyr(O-2,6-di-Cl-Bzl) and Boc-Sar-NH-Resin for Boc-D-Ala-NH-Resin and adding 0.1% DMAP to the Boc-Pro-solution instead of that of the Boc-Ser(O-Bzl). After HF treatment, workup, and HPLC purification N-Ac-D-4-Cl-Phe-D-4-Cl-Phe-D-2-Thia-Ser-Tyr-D-Lys-Leu-Arg-Pro-D-AlaNH$_2$ was obtained as a trifluoroacetate salt; $R_T$=38.52 min; Mass spec. m/e 1390 (M+H)$^+$. Amino Acid Anal: 1.21 Sar; 0.91 Pro; 0.98 Arg; 1.02 Leu; 1.04 Lys; 0.96 Tyr; 0.59 Ser.

EXAMPLE 59

N-Ac-D-4-Cl-Phe-D-4-Cl-Phe-D-1-Nal-Ser-N-Me-Tyr-D-H-Cit-Leu-Arg-Pro-D-AlaNH$_2$

The same procedure described in Example 46 was used, but substituting in the synthesis Boc-D-H-Cit for Boc-D-Lys(N-epsilon-Cbz). After HF treatment, workup, and HPLC purification N-Ac-D-4-Cl-Phe-D-4-Cl-Phe-D-1-Nal-Ser-N-Me-Tyr-D-H-Cit-Leu-Arg-Pro-D-AlaNH$_2$ was obtained as a trifluoroacetate salt; $R_T$=26.32 min; Mass spec. m/e 1491 (M+H)$^+$. Amino Acid Anal: 1.02 Ala; 1.10 Pro; 0.97 Arg; 1.01 Leu; 0.90 Lys; 0.57 Ser.

EXAMPLE 60

N-Ac-D-4-Cl-Phe-D-4-Cl-Phe-D-3-Bal-Ser-N-Tyr-D-Lys(N-epsilon-isopropyl)-Leu-Arg-Pro-D-AlaNH$_2$ The same procedure described in Example 54 was used, but substituting in the synthesis Boc-D-Lys-(N,N-epsilon-isopropyl,Cbz) for Boc-D-Lys(N-epsilon-Cbz).

After HF treatment, workup, and HPLC purification N-Ac-D-4-Cl-Phe-D-4-Cl-Phe-D-3-Bal-Ser-N-Me-Tyr-D-Lys(N-epsilon-isopropyl)-Leu-Arg-Pro-D-AlaNH$_2$ was obtained as a trifluoroacetate salt; R$_T$=27.07 min; Mass spec. m/e 1497 (M+H)$^+$. Amino Acid Anal: 0.97 Ala; 1.04 Pro; 0.97 Arg; 1.02 Leu; 0.53 Ser.

EXAMPLE 61

N-Ac-D-2-Nal-D-4-Cl-Phe-D-3-Pal-Ser-N-Me-Tyr-D-3-Pal-Leu-Lys(N-epsilon-isopropyl)-Pro-D-AlaNH$_2$ The same procedure described in Example 38 was used, but substituting in the synthesis Boc-D-3-Pal for Boc-D-Lys(N-epsilon-FMOC) and using two couplings of 6 hours each for the Boc-D-3-Pal. After HF treatment, workup, and HPLC purification N-Ac-D-2-Nal-D-4-Cl-Phe-D-3-Pal-Ser-N-Me-Tyr-D-3-Pal-Leu-Lys(N-epsilon-isopropyl)-Pro-D-AlaNH2 was obtained as a trifluoroacetate salt; R$_T$=25.67 min; Mass spec. m/e 1449 (M+H)$^+$. Amino Acid Anal: 0.94 Ala; 1.10 prO; 1.06 Leu; 0.54 Ser.

EXAMPLE 62

N-Ac-D-2-Nal-D-4-Cl-Phe-D-3-Pal-Ser-N-Me-Tyr-D-Lys(N-epsilon-2-pyrazincarbonyl)-Leu-Lys(N-epsilon-isopropyl)-Pro-D-AlaNH$_2$ The same procedure described in Example 38 was used, but substituting in the synthesis 2-pyrazine carboxylic acid for nicotinic acid. After HF treatment, workup, and HPLC purification N-Ac-D-2-Nal-D-4-Cl-Phe-D-3-Pal-Ser-N-Me-Tyr-D-Lys(N-epsilon-2-pyrazincarbonyl)-Leu-Lys(N-epsilon-isopropyl)-Pro-D-AlaNH2 was obtained as a trifluoroacetate salt; R$_T$=26.49 min; Mass spec. m/e 1555 (M+H)$^+$. Amino Acid Anal: 0.94 Ala; 1.07 Pro; 1.06 Leu; 1.02 Lys; 0.57 Ser.

EXAMPLE 63

N-Ac-Sar-D-4-Cl-Phe-D-1-Nal-Ser-N-Me-Tyr-D-Lys(N-epsilon-nicotinyl)-Leu-Lys(N-epsilon-isopropyl)-Pro-D-AlaNH$_2$ The same procedure described in Example 38 was used, but substituting in the synthesis N-Ac-Sar for N-Ac-D-2-Nal and Boc-D-1-Nal for Boc-D-3-Pal using two couplings of two hours each. After HF treatment, workup, and HPLC purification N-Ac-Sar-D-4-Cl-Phe-D-1-Nal-Ser-N-Me-Tyr-D-Lys(N-epsilon-nicotinyl)-Leu-Lys(N-epsilon-isopropyl)-Pro-D-AlaNH2 was obtained as a trifluoroacetate salt; R$_T$=27.13 min; Mass spec. m/e 1457 (M+H)$^+$. Amino Acid Anal: 0.98 Ala; 1.09 Pro; 1.08 Leu; 0.95 Lys; 0.49 Ser; 1.12 Sar.

EXAMPLE 64

N-Ac-Sar-D-4-Cl-Phe-D-3-Bal-Ser-N-Me-Tyr-D-Lys(N-epsilon-nicotinyl)-Leu-Lys(N-epsilon-isopropyl)-Pro-D-Ala-NH$_2$ The same procedure described in Example 63 was used, but substituting in the synthesis Boc-D-3-Bal for Boc-D-1-Nal. After HF treatment, workup, and HPLC purification N-Ac-Sar-D-4-Cl-Phe-D-3-Bal-Ser-N-Me-Tyr-D-Lys(N-epsilon-nicotinyl)-Leu-Lys(N-epsilon-isopropyl)-Pro-D-Ala-NH2 was obtained as a trifluoroacetate salt; RT=23.89 min; Mass spec. m/e 1463 (M+H)$^+$. Amino Acid Anal: 0.93 Ala; 1.00 pro; 1.03 Leu; 0.97 Lys; 0.54 Ser.

EXAMPLE 65

N-Ac-alpha-Azagly-D-4-Cl-Phe-D-1-Nal-Ser-N-Me-Tyr-D-Lys(N-epsilon-nicotinyl)-Leu-Lys(N-epsilon-isopropyl)-Pro-D-AlaNH$_2$ The same procedure described in Example 63 was used up to the step before the coupling with N-Ac-Sar. The peptide on the resin was treated with a solution of carbonyldiimidazole (1.13 g) in DMF (18 mL) for 10 minutes, washed (3x) with methylene chloride and then treated overnight with a solution of acetic hydrazide (0.53 g) in (1:1) DMF/methylene chloride (18 mL). Then the synthesis was continued as described in Example 63. After HF treatment, workup, and HPLC purification N-Ac-alpha-Azagly-D-4-Cl-Phe-D-1-Nal-Ser-N-Me-Tyr-D-Lys(N-epsilon-nicotinyl)-Leu-Lys(N-epsilon-isopropyl)-Pro-D-AlaNH2 was obtained as a trifluoroacetate salt; RT=21.86 min; Mass spec. m/e 1444 (M+H)$^+$. Amino Acid Anal: 0.95 Ala; 1.05 Pro; 1.05 Leu; 0.95 Lys; 0.49 Ser.

EXAMPLE 66

N-Ac-D-2-Nal-D-4-Cl-Phe-D-3-Pal-Ser-N-Me-Tyr-D-Lys(N-epsilon-nicotinyl)-Cha-Arg-Pro-D-AlaNH$_2$ The same procedure described in Example 38 was used, but substituting Boc-Cha for Boc-Leu and Boc-Arg(Tos) for Boc-Lys(N,N-epsilon-isopropyl,Cbz). After HF treatment, workup, and HPLC purification N-Ac-D-2-Nal-D-4-Cl-Phe-D-3-Pal-Ser-N-Me-Tyr-D-Lys(N-epsilon-nicotinyl)-Cha-Arg-Pro-D-AlaNH$_2$ was obtained as a trifluoroacetate salt; RT=24.39 min; Mass spec. m/e 1560 (M+H)$^+$. Amino Acid Anal: 1.03 Ala; 1.14 Pro; 0.96 Arg; 0.91 Cha; 1.01 Lys; 0.52 Ser.

EXAMPLE 67

N-Ac-D-2-Nal-D-4-Cl-Phe-D-3-Pal-Ser-N-Me-Tyr-D-Lys(N-epsilon-nicotinyl)-N-Me-Leu-Lys(N-epsilon-isopropyl)-Pro-D-AlaNH$_2$ The same procedure described in Example 38 was used, but substituting Boc-N-Me-Leu for Boc-Leu. After HF treatment, workup, and HPLC purification N-Ac-D-2-Nal-D-4-Cl-Phe-D-3-Pal-Ser-N-Me-Tyr-D-Lys(N-epsilon-nicotinyl)-N-Me-Leu-Lys(N-epsilon-isopropyl)-Pro-D-AlaNH2 was obtained as a trifluoroacetate salt; RT=19.18 min; Mass spec. m/e 1549 (M+H)$^+$. Amino Acid Anal: 1.00 Ala; 1.10 Pro; 1.00 Lys; 0.56 Ser.

EXAMPLE 68

N-Ac-D-4-Cl-Phe-D-4-Cl-Phe-D-2-Thia-Ser-N-Me-Tyr-D-Lys(N-epsilon-nicotinyl)-N-Me-Leu-Arg-Pro-D-Ala-NH$_2$ The same procedure described in Example 57 was used, but substituting Boc-D-2-Thia for Boc-D-2-Nal. After HF treatment, workup, and HPLC purification N-Ac-D-4-Cl-Phe-D-4-Cl-Phe-D-2-Thia-Ser-N-Me-Tyr-D-Lys(N-epsilon-nicotinyl)-N-Me-Leu-Arg-Pro-D-Ala-NH2 was obtained as a trifluoroacetate salt; RT=27.93 min; Mass spec. m/e 1524 (M+H)$^+$. Amino Acid Anal: 0.98 Ala; 1.10 Pro; 1.01 Arg; 1.01 Lys; 0.51 Ser.

EXAMPLE 69

N-Ac-D-2-Nal-D-4-Cl-Phe-D-3-Pal-Ser-N-Me-Tyr-D-Lys-epsilon-CO-Morph)-Leu-Lys(N-epsilon-isopropyl)-Pro-D-AlaNH$_2$ The same procedure described in Example 38 was used up to the step of the removal of the FMOC group. Instead of coupling with nicotinic acid the peptide on the resin was first deblocked with 50% TFA/methylene chloride solution for 20 minutes, washed with diisopropylethylamine (2×), washed with methylene chloride (3×) and then treated with a solution of carbonyldiimidazole (1.13 g) in DMF (18 mL) for ten minutes, washed (3×) with methylene chloride, and then reacted overnight with a solution of morpholine (0.8 mL) in (1:1) DMF/methylene chloride (18 mL) solution. The resin was washed (3×) with methylene chloride, dried overnight over P$_2$O$_5$, and treated with HF/anisole at 0° C. for 1 hr. Workup and HPLC purification gave N-Ac-D-2-Nal-D-4-Cl-Phe-D-3-Pal-Ser-N-Me-Tyr-D-Lys(N-epsilon-CO-Morph)-Leu-Lys(N-epsilon-isopropyl)-Pro-D-AlaNH$_2$ as a trifluoroacetate salt; R$_T$=23.55 min; Mass spec. m/e 1542 (M+H)$^+$. Amino Acid Anal: 1.16 Ala; 1.04 Pro; 0.99 Leu; 0.97 Lys; 0.35 Ser.

EXAMPLE 70

N-Ac-D-2--Nal-D-4-Cl-Phe-D-3-Pal-Ser-N-Me-Tyr-D-Lys(N-epsilon-CO-NMePip)-Leu-Lys(N-epsilon-isopropyl)-Pro-D-AlaNH$_2$ The same procedure described in Example 69 was used, but substituting N-methyl-piperazine for morpholine. After HF treatment, workup, and HPLC purification N-Ac-D-2-Nal-D-4-Cl-Phe-D-3-Pal-Ser-N-Me-Tyr-D-Lys(N-epsilon-CO-NMePip)-Leu-Lys(N-epsilon-isopropyl)-Pro-D-AlaNH$_2$ was obtained as a trifluoroacetate salt; R$_T$=18.41 min; Mass spec. m/e 1556 (M+H)$^+$. Amino Acid Anal: 0.93 Ala; 1.10 Pro; 1.05 Leu; 1.02 Lys; 0.55 Ser.

EXAMPLE 71

Using the same procedure described in Example 65, but substituting the appropriate acid hydrazides for acetic hydrazide the following compounds can be prepared:

N-acetyl-alpha-aza-alanyl-D-3-(4-chlorophenyl)alanyl-D-3-(1-naphthyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-3-(4-chlorophenyl)alanyl-D-3-(4-chlorophenyl)alanyl-D-3-(1-naphthyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-3-(2-naphthyl)alanyl-D 3-(4-chlorophenyl)alanyl-D-3-(1-naphthyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-phenylalanyl-D-3-(4-chlorophenyl)alanyl-D-3-(1-naphthyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-3-(4-fluorophenyl)alanyl-D-3-(4-chlorophenyl)alanyl-D-3-(1-naphthyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-sarcosyl-D-3-(4-chlorophenyl)alanyl-D-3-(1-naphthyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-methyl-alpha-aza-pyroglutamyl-D-3-(4-chlorophenyl)alanyl-D-3-(1-naphthyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-tyrosyl(O-methyl)-D-3-(4-chlorophenyl)alanyl-D-3-(1-naphthyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-3-(3-benzthienyl)alanyl-D-3-(4-chlorophenyl)alanyl-D-3-(1-naphthyl)alanyl-seryl-N-alpha-methyl-tyrosyl-D-lysyl(N-epsilon-nicotinyl)-leucyl-lysyl(N-epsilon-isopropyl)-prolyl-D-alanylamide; and N-acetyl-alpha-aza-3-(2-thienyl)alanyl-D-3-(4-chlorophenyl)alanyl-D-3-(1-naphthyl)alanyl-seryl-N-alpha-methyl-tyrosyl-D-lysyl(N-epsilon-nicotinyl)-leucyl-lysyl(N-epsilon-isopropyl)-prolyl-D-alanylamide.

EXAMPLE 72

Using the same procedure described in Example 65, but substituting the appropriate amino acids for D-1-(3-naphthyl)alanyl at position 3 the following compounds can be prepared:

N-acetyl-alpha-aza-glycyl-D-3-(4-chlorophenyl)alanyl-D-tryptyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-glycyl-D-3-(4-chlorophenyl)alanyl-D-tryptyl(N-indole-formyl)-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-glycyl-D-3-(4-chlorophenyl)alanyl-D-3-(3-benzthienyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-glycyl-D-3-(4-chlorophenyl)alanyl-D-3-(4-chlorophenyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-glycyl-D-3-(4-chlorophenyl)alanyl-D-3-(cyclohexyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-glycyl-D-3-(4-chlorophenyl)alanyl-D-3-(2-thienyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-glycyl-D-3-(4-chlorophenyl)alanyl-D-3-(4-thiazolyl)alanyl-seryl-N-alpha-methyl-tyrosyl-D-lysyl(N-epsilon-nicotinyl)-leucyl-lysyl(N-epsilon-isopropyl)-prolyl-D-alanylamide; and N-acetyl-alpha-aza-glycyl-D-3-(4-chlorophenyl)alanyl-D-3-(3-pyridyl)alanyl-seryl-N-alpha-methyl-tyrosyl-D-lysyl(N-epsilon-nicotinyl)-leucyl-lysyl(N-epsilon-isopropyl)-prolyl-D-alanylamide.

EXAMPLE 73

Using the same procedure described in Example 72, but substituting N-alpha-methyl-tyrosyl(O-methyl) for N-alpha-methyl-tyrosyl the following compounds can be prepared:

N-acetyl-alpha-aza-glycyl-D-3-(4-chlorophenyl)ala-
  nyl-D-tryptyl-seryl-N-alpha-methyl-tyrosyl(O-methyl)-
  D-lysyl(N-epsilon-nicotinyl)-leucyl-lysyl(N-epsilon-
  isopropyl)-prolyl-D-alanylamide;
N-acetyl-alpha-aza-glycyl-D-3-(4-chlorophenyl)alanyl-
  D-tryptyl(N-indole-formyl)-seryl-N-alpha-methyl-
  tyrosyl(O-methyl)-D-lysyl(N-epsilon-nicotinyl)-leu-
  cyl-lysyl(N-epsilon-isopropyl)-prolyl-D-alanylamide;
N-acetyl-alpha-aza-glycyl-D-3-(4-chlorophenyl)alanyl-
  D-3-(3-benzthienyl)alanyl-seryl-N-alpha-methyl-
  tyrosyl(O-methyl)-D-lysyl(N-epsilon-nicotinyl)-leu-
  cyl-lysyl(N-epsilon-isopropyl)-prolyl-D-alanylamide;
N-acetyl-alpha-aza-glycyl-D-3-(4-chlorophenyl)alanyl-
  D-3-(4-chlorophenyl)alanyl-seryl-N-alpha-methyl-
  tyrosyl(O-methyl)-D-lysyl(N-epsilon-nicotinyl)-leu-
  cyl-lysyl(N-epsilon-isopropyl)-prolyl-D-alanylamide;
N-acetyl-alpha-aza-glycyl-D-3-(4-chlorophenyl)alanyl-
  D-3-(cyclohexyl)alanyl-seryl-N-alpha-methyl-
  tyrosyl(O-methyl)-D-lysyl(N-epsilon-nicotinyl)-leu-
  cyl-lysyl(N-epsilon-isopropyl)-prolyl-D-alanylamide;
N-acetyl-alpha-aza-glycyl-D-3-(4-chlorophenyl)alanyl-
  D-3-(2-thienyl)alanyl-seryl-N-alpha-methyl-tyrosyl-
  (O-methyl)-D-lysyl(N-epsilon-nicotinyl)-leucyl-
  lysyl(N-epsilon-isopropyl)-prolyl-D-alanylamide;
N-acetyl-alpha-aza-glycyl-D-3-(4-chlorophenyl)alanyl-
  D-3-(4-thiazolyl)alanyl-seryl-N-alpha-methyl-
  tyrosyl(O-methyl)-D-lysyl(N-epsilon-nicotinyl)-leu-
  cyl-lysyl(N-epsilon-isopropyl)-prolyl-D-alanylamide;
N-acetyl-alpha-aza-glycyl-D-3-(4-chlorophenyl)alanyl-
  D-3-(3-pyridyl)alanyl-seryl-N-alpha-methyl-tyrosyl-
  (O-methyl)-D-lysyl(N-epsilon-nicotinyl)-leucyl-
  lysyl(N-epsilon-isopropyl)-prolyl-D-alanylamide;
  and
N-acetyl-alpha-aza-glycyl-D-3-(4-chlorophenyl)alanyl-
  D-3-(3-benzthienyl)alanyl-seryl-N-alpha-methyl-
  tyrosyl(O-methyl)-D-lysyl(N-epsilon-nicotinyl)-leu-
  cyl-lysyl(N-epsilon-isopropyl)-prolyl-D-alanylamide.

EXAMPLE 73

Using the same procedure described in Example 63, but substituting the appropriate amino acids for D-1-(3-naphthyl)alanyl at position 3 the following compounds can be prepared:

N-acetyl-sarcosyl-D-3-(4-chlorophenyl)alanyl-D-tryp-
  tyl-seryl-N-alpha-methyl-tyrosyl-D-lysyl(N-epsilon-
  nicotinyl)-leucyl-lysyl(N-epsilon-isopropyl)-prolyl-
  D-alanylamide;
N-acetyl-sarcosyl-D-3-(4-chlorophenyl)alanyl-D-tryp-
  tyl(N-indole-formyl)-seryl-N-alpha-methyl-tyrosyl-
  D-lysyl(N-epsilon-nicotinyl)-leucyl-lysyl(N-epsilon-
  isopropyl)-prolyl-D-alanylamide;
N-acetyl-sarcosyl-D-3-(4-chlorophenyl)alanyl-D-3-(3-
  benzthienyl)alanyl-seryl-N-alpha-methyl-tyrosyl-D-
  lysyl(N-epsilon-nicotinyl)-leucyl-lysyl(N-epsilon-iso-
  propyl)-prolyl-D-alanylamide;
N-acetyl-sarcosyl-D-3-(4-chlorophenyl)alanyl-D-3-(4-
  chlorophenyl)alanyl-seryl-N-alpha-methyl-tyrosyl-
  D-lysyl(N-epsilon-nicotinyl)-leucyl-lysyl(N-epsilon-
  isopropyl)-prolyl-D-alanylamide;
N-acetyl-sarcosyl-D-3-(4-chlorophenyl)alanyl-D-3-(cy-
  clohexyl)alanyl-seryl-N-alpha-methyl-tyrosyl-D-
  lysyl(N-epsilon-nicotinyl-leucyl-lysyl(N-epsilon-iso-
  propyl)-prolyl-D-alanylamide;
N-acetyl-sarcosyl-D-3-(4-chlorophenyl)alanyl-D-3-(2-
  thienyl)alanyl-seryl-N-alpha-methyl-tyrosyl-D-
  lysyl(N-epsilon-nicotinyl)-leucyl-lysyl(N-epsilon-iso-
  propyl)-prolyl-D-alanylamide; and
N-acetyl-sarcosyl-D-3-(4-chlorophenyl)alanyl-D-3-(3-
  pyridyl)alanyl-seryl-N-alpha-methyl-tyrosyl-D-
  lysyl(N-epsilon-nicotinyl)-leucyl-lysyl(N-epsilon-iso-
  propyl)-prolyl-D-alanylamide.

EXAMPLE 74

Using the same procedure described in Example 72, but substituting D-3-(3-pyridyl)alanyl at position 6 for D-lysyl(N-epsilon-nicotinyl) the following compounds can be prepared:

N-acetyl-alpha-aza-glycyl-D-3-(4-chlorophenyl)alanyl-
  D-tryptyl-seryl  N-alpha-methyl-tyrosyl-D-3-(3-
  pyridyl)alanyl-leucyl-lysyl(N-epsilon-isopropyl)-pro-
  lyl-D-alanylamide;
N-acetyl-alpha-aza-glycyl-D-3-(4-chlorophenyl)alanyl-
  D-tryptyl(N-indole-formyl)-seryl-N-alpha-methyl-
  tyrosyl-D-3-(3-pyridyl)alanyl-leucyl-lysyl(N-epsilon-
  isopropyl)-prolyl-D-alanylamide;
N-acetyl-alpha-aza-glycyl-D-3-(4-chlorophenyl)alanyl-
  D-3-(3-benzthienyl)alanyl-seryl-N-alpha-methyl-
  tyrosyl-D-3-(3-pyridyl)alanyl-leucyl-lysyl(N-epsilon-
  isopropyl)-prolyl-D-alanylamide;
N-acetyl-alpha-aza-glycyl-D-3-(4-chlorophenyl)alanyl-
  D-3-(4-chlorophenyl)alanyl-seryl-N-alpha-methyl-
  tyrosyl-D-3-(3-pyridyl)alanyl-leucyl-lysyl(N-epsilon-
  isopropyl)-prolyl-D-alanylamide;
N-acetyl-alpha-aza-glycyl-D-3-(4-chlorophenyl)alanyl-
  D-3-(cyclohexyl)alanyl-seryl-N-alpha-methyl-tyro-
  syl-D-3-(3-pyridyl)alanyl-leucyl-lysyl(N-epsilon-iso-
  propyl)-prolyl-D-alanylamide;
N-acetyl-alpha-aza-glycyl-D-3-(4-chlorophenyl)alanyl-
  D-3-(2-thienyl)alanyl-seryl-N-alpha-methyl-tyrosyl-
  D-3-(3-pyridyl)alanyl-leucyl-lysyl(N-epsilon-iso-
  propyl)-prolyl-D-alanylamide;
N-acetyl-alpha-aza-glycyl-D-3-(4-chlorophenyl)alanyl-
  D-3-(4-thiazolyl)alanyl-seryl-N-alpha-methyl-tyro-
  syl-D-3-(3-pyridyl)alanyl-leucyl-lysyl(N-epsilon-iso-
  propyl)-prolyl-D-alanylamide; and
N-acetyl-alpha-aza-glycyl-D-3-(4-chlorophenyl)alanyl-
  D-3-(3-pyridyl)alanyl-seryl-N-alpha-methyl-tyrosyl-
  D-3-(3-pyridyl)alanyl-leucyl-lysyl(N-epsilon-iso-
  propyl)-prolyl-D-alanylamide.

EXAMPLE 75

Using the same procedure described in Example 72, but substituting D-3-(4-fluorophenyl)alanyl for D-3-(4-chlorophenyl)alanyl the following compounds can be prepared:

N-acetyl-alpha-aza-glycyl-D-3-(4-fluorophenyl)alanyl-
  D-tryptyl-seryl-N-alpha-methyl-tyrosyl-D-lysyl(N-
  epsilon-nicotinyl)-leucyl-lysyl(N-epsilon-isopropyl)-
  prolyl-D-alanylamide;
N-acetyl-alpha-aza-glycyl D-3-(4-fluorophenyl)alanyl-
  D-tryptyl(N-indole-formyl)-seryl-N-alpha-methyl-
  tyrosyl-D-lysyl(N-epsilon-nicotinyl)-leucyl-lysyl(N-
  epsilon-isopropyl)-prolyl-D-alanylamide;
N-acetyl-alpha-aza-glycyl-D-3-(4-fluorophenyl)alanyl-
  D-3-(3-benzthienyl)alanyl-seryl-N-alpha-methyl-
  tyrosyl-D-lysyl(N-epsilon-nicotinyl)-leucyl-lysyl(N-
  epsilon-isopropyl)-prolyl-D alanylamide;
N-acetyl-alpha-aza-glycyl-D-3-(4-fluorophenyl)alanyl-
  D-3-(4-chlorophenyl)alanyl-seryl-N-alpha-methyl-
  tyrosyl-D-lysyl(N-epsilon-nicotinyl)-leucyl-lysyl(N-
  epsilon-isopropyl)-prolyl-D-alanylamide;
N-acetyl-alpha-aza-glycyl-D-3-(4-fluorophenyl)alanyl-
  D-3-(cyclohexyl)alanyl-seryl-N-alpha-methyl-tyro-
  syl-D-lysyl(N-epsilon-nicotinyl)-leucyl-lysyl(N-epsi-
  lon-isopropyl)-prolyl-D-alanylamide;

N-acetyl-alpha-aza-glycyl-D-3-(4-fluorophenyl)alanyl-D-3-(2-thienyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-glycyl-D-3-(4-fluorophenyl)alanyl-D-3-(4-thiazolyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-glycyl-D-3-(4-fluorophenyl)alanyl-D-3-(3-pyridyl)alanyl-seryl-N-alpha-methyl-tyrosyl-D-lysyl(N-epsilon-nicotinyl)-leucyl-lysyl(N-epsilon-isopropyl)-prolyl-D-alanylamide; and N-acetyl-alpha-aza-glycyl-D-3-(4-fluorophenyl)alanyl-D-3-(3-quinolyl)alanyl-seryl-N-alpha-methyl-tyrosyl-D-lysyl(N-epsilon-nicotinyl)-leucyl-lysyl(N-epsilon-isopropyl)-prolyl-D-alanylamide.

EXAMPLE 76

Using the same procedure described in Example 75, but substituting D-3-(2-naphthyl)alanyl for D-3-(4-fluorophenyl)alanyl the following compounds can be prepared:

N-acetyl-alpha-aza-glycyl-D-3-(2-naphthyl)alanyl-D-tryptyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-glycyl-D-3-(2-naphthyl)alanyl-D-tryptyl(N-indole-formyl)-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-glycyl-D-3-(2-naphthyl)alanyl-D-3-(3-benzthienyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-glycyl-D-3-(2-naphthyl)alanyl-D-3-(4-chlorophenyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-glycyl-D-3-(2-naphthyl)alanyl-D-3-(cyclohexyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-glycyl-D-3-(2-naphthyl)alanyl-D-3-(2-thienyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-glycyl-D-3-(2-naphthyl)alanyl-D-3-(4-thiazolyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-glycyl-D-3-(2-naphthyl)alanyl-D-3-(3-pyridyl)alanyl-seryl-N-alpha-methyl-tyrosyl-D-lysyl(N-epsilon-nicotinyl)-leucyl-lysyl(N-epsilon-isopropyl)-prolyl-D-alanylamide; and N-acetyl-alpha-aza-glycyl-D-3-(2-naphthyl)alanyl-D-3-(3-quinolyl)alanyl-seryl-N-alpha-methyl-tyrosyl-D-lysyl(N-epsilon-nicotinyl)-leucyl-lysyl(N-epsilon-isopropyl)-prolyl-D-alanylamide.

EXAMPLE 77

Using the same procedure described in Example 76, but substituting D-phenylalanyl for D-3-(2-naphthyl)alanyl the following compounds can be prepared:

N-acetyl-alpha-aza-glycyl-D-phenylalanyl-D-tryptyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-glycyl-D-phenylalanyl-D-tryptyl(N-indole-formyl)-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-glycyl-D-phenylalanyl-D-3-(3-benzthienyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-glycyl-D-phenylalanyl-D-3-(4-chlorophenyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-glycyl-D-phenylalanyl-D-3-(cyclohexyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-glycyl-D-phenylalanyl-D-3-(2-thienyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-glycyl-D-phenylalanyl-D-3-(4-thiazolyl)alanyl-seryl-N-alpha methyl-tyrosyl-D-lysyl(N-epsilon-nicotinyl)-leucyl-lysyl(N-epsilon-isopropyl)-prolyl-D-alanylamide; and N-acetyl-alpha-aza-glycyl-D-phenylalanyl-D-3-(3-pyridyl)alanyl-seryl-N-alpha-methyl-tyrosyl-D-lysyl(N-epsilon-nicotinyl)-leucyl-lysyl(N-epsilon-isopropyl)-prolyl-D-alanylamide.

EXAMPLE 78

N-Ac-D-2-Nal-alpha-aza-4-Cl-Phe-D-3-Pal-Ser-N-Me-Tyr-D-Lys(N-epsilon-nicotinyl)-Leu-Lys(N-epsilon-isopropyl)-Pro-D-AlaNH$_2$ The same procedure described in Example 38 can be used to synthesize the peptide-resin Boc-D-3-Pal-Ser(O-Bzl)-N-Me-Tyr(O-2,6-diCl-Bzl)-D-Lys(N-epsilon-FMOC)-Leu-Lys(N,N-epsilon-isopropyl,Cbz)-Pro-D-AlaNH-Resin. This resin is treated with deblock solution (see Example 1) for 20 minutes to remove the Boc group, then washed twice with base wash, and three times with methylene chloride and reacted with carbonyldiimidazole (1.13 g) in DMF (18 mL) for 10 minutes. The peptide-resin is washed (3×) with methylene chloride and reacted overnight with a solution of N-Boc-N'-(4-Cl-benzyl)hydrazine (1.8 g) in (1:1) methylene chloride/DMF (18 mL) to give N-Boc-alpha-aza-4-Cl-Phe-D-3-Pal-Ser(O-Bzl)-N-Me-Tyr(O-2,6-diCl-Bzl)-D-Lys(N-epsilon-FMOC)-Leu-Lys(N,N-epsilon-isopropyl,Cbz)-Pro-D-AlaNH-Resin. This is treated with deblock solution for 20 minutes, base washed, and the synthesis is continued as described in Example 38. After HF treatment, workup, and HPLC purification N-Ac-D-2-Nal-alpha-aza-4-Cl-Phe-D-3-Pal-Ser-N-Me-Tyr-D-Lys(N-epsilon-nicotinyl)-Leu-Lys(N epsilon-isopropyl)-Pro-D-AlaNH$_2$ can be obtained as the trifluoroacetate salt.

EXAMPLE 79

Using the same procedure described in Example 78 and substituting the appropriate N-Boc-N'-aryl-hydrazine or N-Boc-N'-alkyl-hyrdazine for N-Boc-N'-(4-Cl-benzyl)hydrazine the following compounds can be obtained:

N-acetyl-D-3-(2-naphthyl)alanyl-alpha-aza-3-(2-naphthyl)alanyl-D-3-(3-pyridyl)alanyl-seryl-N alpha-methyl-tyrosyl-D-lysyl(N-epsilon-nicotinyl)-leucyl-lysyl(N-epsilon-isopropyl)-prolyl-D-alanylamide;

N-acetyl-D-3-(2-naphthyl)alanyl-alpha-aza-3-(4-fluorophenyl)alanyl-D-3-(3-pyridyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-D-3-(2-naphthyl)alanyl-alpha-aza-3-(4-methoxyphenyl)alanyl-D-3-(3-pyridyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-D-3-(2-naphthyl)alanyl-alpha-aza-tryptyl-D-3-(3-pyridyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-D-3-(2-naphthyl)alanyl-alpha-aza-3-(3-benzthienyl)alanyl-D-3-(3-pyridyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-D-3-(2-naphthyl)alanyl-alpha-aza-3-(cyclohexyl)alanyl-D-3-(3-pyridyl)alanyl-seryl-N-alpha-methyl-tyrosyl-D-lysyl(N-epsilon-nicotinyl)-leucyl-lysyl(N-epsilon-isopropyl)-prolyl-D-alanylamide; and N-acetyl-D-3-(2-naphthyl)alanyl-alpha-aza-3-(2-thienyl)alanyl-D 3-(3-pyridyl)alanyl-seryl-N-alpha-methyl-tyrosyl-D-lysyl(N-epsilon-nicotinyl)-leucyl-lysyl(N-epsilon-isopropyl)-prolyl-D-alanylamide.

EXAMPLE 80

N-Ac-aloha-aza-Gly-aloha-aza-4-Cl-Phe-D-1-Nal-Ser-N-Me-Tyr-D-Lys(N-epsilon-nicotinyl)-Leu-Lys(N-epsilon-isopropyl)-Pro-D-AlaNH$_2$ The same procedure described in Example 65 is used to synthesize the peptide up to Boc-alpha-aza-4-Cl-Phe-D-1-Nal-Ser(O-Bzl)-N-Me-Tyr(O-2,6-diCl-Bzl)-D-Lys(N-epsilon-FMOC)-Leu-Lys(N,N-epsilon-isopropyl,Cbz)-Pro-D-AlaNH-Resin. This resin is deblocked, reacted with carbonyldiimidazole, and reacted with acetic hydrazide as described in Example 65 to give N-Ac-alpha-aza-Gly-alpha-aza-4-Cl-Phe-D-1-Nal-Ser(O-Bzl)-N-Me-Tyr(O-2,6-diCl-Bzl)-D-Lys(N-epsilon-FMOC)-Leu-Lys(N,N-epsilon-isopropyl,Cbz)-Pro-D-AlaNH-Resin. The synthesis is continued as described in Example 65. After HF treatment, workup, and HPLC purification N-Ac-alpha-aza-Gly-alpha-aza-4-Cl-Phe-D-1-Nal-Ser-N-Me-Tyr-D-Lys(N-epsilon-nicotinyl)-Leu-Lys(N-epsilon-isopropyl)-Pro-D-AlaNH$_2$ can be obtained as the trifluoroacetate salt.

EXAMPLE 81

The same procedure described in Example 80 is used, but substituting the appropriate Boc-D-amino acids for Boc-D-1-Nal the following compounds can be made:

N-acetyl-alpha-aza-glycyl-alpha-aza-3-(4-chlorophenyl)alanyl-D-3-(3-benzthienyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-glycyl-alpha-aza-3-(4-chlorophenyl)alanyl-D-tryptyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-glycyl-alpha-aza-3-(4-chlorophenyl)alanyl-D-tryptyl(N-indole-formyl)-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-glycyl-alpha-aza-3-(4-chlorophenyl)alanyl-D-3-(4-chlorophenyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-alpha-aza-glycyl-alpha-aza-3-(4-chlorophenyl)alanyl-D-3-(2-thienyl)alanyl-seryl-N-alpha-methyl-tyrosyl-D-lysyl(N-epsilon-nicotinyl)-leucyl-lysyl(N-epsilon-isopropyl)-prolyl-D-alanylamide; and N-acetyl-alpha-aza-glycyl-alpha-aza-3-(4-chlorophenyl)alanyl-D-3-(2-naphthyl)alanyl-seryl-N-alpha-methyl-tyrosyl-D-lysyl(N-epsilon-nicotinyl)-leucyl-lysyl(N-epsilon-isopropyl)-prolyl-D-alanylamide.

EXAMPLE 82

N-Ac-Sar-aloha-aza-4-Cl-Phe-D-1-Nal-Ser-N-Me-Tyr-D-Lys(N-epsilon-nicotinyl)-Leu-Lys(N-epsilon-isopropyl)-Pro-D-AlaNH$_2$ The procedure described in Example 80 is used up to the step to give Boc-alpha-aza-4-Cl-Phe-D-1-Nal-Ser-(O-Bzl)-N-Me-Tyr(O-2,6-diCl-Bzl)-D-Lys(N-epsilon-FMOC)-Leu-Lys(N,N-epsilon-isopropyl,Cbz)-Pro-D-AlaNH-Resin. This resin is coupled to N-Ac-Sar and the synthesis completed as described in Example 63. After HF treatment, workup, and HPLC purification N-Ac-Sar-alpha-aza-4-Cl-Phe-D-1-Nal-Ser-N-Me-Tyr-D-Lys(N-epsilon-nicotinyl)-Leu-Lys(N-epsilon-isopropyl)-Pro-D-AlaNH$_2$ can be obtained as the trifluoroacetate salt.

EXAMPLE 83

The procedure described in Example 82 is used, but substituting the appropriate Boc-D-amino acid for Boc-D-1-Nal the following compounds can be obtained:

N-acetyl-sarcosyl-alpha-aza-3-(4-chlorophenyl)alanyl-D-3-(3-benzthienyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-sarcosyl-alpha-aza-3-(4-chlorophenyl)alanyl-D-3-(2-thienyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-sarcosyl-alpha-aza-3-(4-chlorophenyl)alanyl-D-tryptyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-sarcosyl-alpha-aza-3-(4-chlorophenyl)alanyl-D-tryptyl(N-indole-formyl)-seryl-N-alpha-methyl-tyrosyl-D-lysyl(N-epsilon-nicotinyl)-leucyl-lysyl(N-epsilon-isopropyl)-prolyl-D-alanylamide;

N-acetyl-sarcosyl-alpha-aza-3-(4-chlorophenyl)alanyl-D-3-(4-chlorophenyl)alanyl-seryl-N-alpha-methyl-tyrosyl-D-lysyl(N-epsilon-nicotinyl)-leucyl-lysyl(N-epsilon-isopropyl)-prolyl-D-alanylamide; and N-acetyl-sarcosyl-alpha-aza-3-(4-chlorophenyl)alanyl-D-3-(4-methoxyphenyl)alanyl-seryl-N-alpha-methyl-tyrosyl-D-lysyl(N-epsilon-nicotinyl)-leucyl-lysyl(N-epsilon-isopropyl)-prolyl-D-alanylamide.

EXAMPLE 84

The same procedure described in Example 38 is used, but substituting in the synthesis Boc-D-amino acid for Boc-D-3-Pal. After HF treatment, workup, and HPLC purification the following compounds can be obtained:

N-acetyl-D-3-(2-naphthyl)alanyl-D-3-(4-chlorophenyl)alanyl-D-3-(1-naphthyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-D-3-(2-naphthyl)alanyl-D-3-(4-chlorophenyl)alanyl-D-3-(3-benzthienyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-D-3-(2-naphthyl)alanyl-D-3-(4-chlorophenyl)alanyl D-3-(2-thienyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-D-3-(2-naphthyl)alanyl-D-3-(4-chlorophenyl)alanyl-D-tryptyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-D-3-(2-naphthyl)alanyl-D-3-(4-chlorophenyl)alanyl-D-tryptyl(N-indole-formyl)-seryl N-alpha-methyl-tyrosyl-D-lysyl(N-epsilon-nicotinyl)-leucyl-lysyl(N-epsilon-isopropyl)-prolyl-D-alanylamide;

N-acetyl-D-3-(2-naphthyl)alanyl-D-3-(4-chlorophenyl)alanyl-D-tryptyl(N-indole-methyl)-seryl-N-alpha-methyl-tyrosyl-D-lysyl(N-epsilon-nicotinyl)-leucyl-lysyl(N-epsilon-isopropyl)-prolyl-D-alanylamide;

N-acetyl-D-3-(2-naphthyl)alanyl-D-3-(4-chlorophenyl)alanyl-D-3-(4-methoxyphenyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-D-3-(2-naphthyl)alanyl-D-3-(4-chlorophenyl)alanyl-D-tyrosyl(O-methyl)-seryl-N-alpha-methyl-tyrosyl-D-lysyl(N-epsilon-nicotinyl)-leucyl-lysyl(N-epsilon-isopropyl)-prolyl-D-alanylamide;

N-acetyl-D-3-(2-naphthyl)alanyl-D-3-(4-chlorophenyl)alanyl-D-3-(3-quinolyl)alanyl-seryl-N-alpha-methyl-tyrosyl-D-lysyl(N-epsilon-nicotinyl)-leucyl-lysyl(N-epsilon-isopropyl)-prolyl-D-alanylamide; and N-acetyl-D-3-(2-naphthyl)alanyl-D-3-(4-chlorophenyl)alanyl-D-3-(cyclohexyl)alanyl-seryl-N-alpha-methyl-tyrosyl-D-lysyl(N-epsilon-nicotinyl)-leucyl-lysyl(N-epsilon-isopropyl)-prolyl-D-alanylamide.

EXAMPLE 85

N-Ac-D-2-Nal-D-4-Cl-Phe-N-alpha-aza-3-Pal-Ser-N-Me-Tyr-D-Lys(N-epsilon-isopropyl)-Pro-D-AlaNH$_2$ The procedure described in Example 38 is used up to step Boc-Ser(O-Bzl)-N-Me-Tyr(O-2,6-diCl-Bzl)-D-Lys(N-epsilon-FMOC)-Leu-Lys(N,N-epsilon-isopropyl,Cbz)-Pro-D-AlaNH-Resin. The resin is treated with deblock solution for 20 minutes to remove the Boc group, treated with base wash, and reacted with carbonyldiimidazole for 10 minutes, washed (3×) with methylene chloride, and reacted overnight with N-Boc-N'-(3-pyridylmethyl)hydrazine as described in Example 78 to give Boc-alpha-aza-3-Pal-Ser(O-Bzl)-N-Me-Tyr-(O-2,6-diCl-Bzl)-D-Lys(N-epsilon-FMOC)-Leu-Lys(N,N-epsilon-isopropyl,Cbz)-Pro-D-AlaNH-Resin. This resin is deblocked and then coupled with Boc-D-4-Cl-Phe and N-Ac-D-2-Nal as described in Example 38. After HF treatment, workup, and HPLC purification N-Ac-D-2-Nal-D-4-Cl-Phe-N-alpha-aza-3-Pal-Ser-N-Me-Tyr-D-Lys(N-epsilon-nicotinyl)-Leu-Lys(N-epsilon-isopropyl)-Pro-D-AlaNH$_2$ can be obtained as the trifluoroacetate salt.

EXAMPLE 86

Using the procedure described in Example 85, but substituting the appropriate N-alpha-aza-amino acids for N-alpha-aza-3-Pal the following compounds can be prepared:

N-acetyl-D-3-(2-naphthyl)alanyl-D-3-(4-chlorophenyl)alanyl-N-alpha-aza-3-(1-naphthyl)alanyl-seryl-N-alpha-methyl-tyrosyl-D-lysyl(N epsilon-nicotinyl)-leucyl-lysyl(N-epsilon-isopropyl)-prolyl-D-alanylamide;

N-acetyl-D-3-(2-naphthyl)alanyl-D-3-(4-chlorophenyl)alanyl-N-alpha-aza-3-(3-benzthienyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-D-3-(2-naphthyl)alanyl-D-3-(4-chlorophenyl)alanyl-N-alpha-aza-tryptyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-D-3-(2-naphthyl)alanyl-D-3-(4-chlorophenyl)alanyl-N-alpha-aza-tryptyl(N-indole-formyl)-seryl-N-alpha-methyl-tyrosyl-D-lysyl(N-epsilon-nicotinyl)-leucyl-lysyl(N-epsilon-isopropyl)-prolyl-D-alanylamide;

N-acetyl-D-3-(2-naphthyl)alanyl-D-3-(4-chlorophenyl)alanyl-N-alpha-aza-tryptyl(N-indole-methyl)-seryl-N-alpha-methyl-tyrosyl-D-lysyl(N-epsilon-nicotinyl)-leucyl-lysyl(N-epsilon-isopropyl)-prolyl-D-alanylamide;

N-acetyl-D-3-(2-naphthyl)alanyl-D-3-(4-chlorophenyl)alanyl-N-alpha-aza-3-(4-methylphenyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-D-3-(2-naphthyl)alanyl-D-3-(4-chlorophenyl)alanyl-N-alpha-aza-3-(2-thienyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-D-3-(2-naphthyl)alanyl-D-3-(4-chlorophenyl)alanyl-N-alpha-aza-3-(4-chlorophenyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-D-3-(2-naphthyl)alanyl-D-3-(4-chlorophenyl)alanyl-N-alpha-aza-3-(4-methoxyphenyl)alanyl-seryl-N-alpha-methyl-tyrosyl-D-lysyl(N-epsilon-nicotinyl)-leucyl-lysyl(N-epsilon-isopropyl)-prolyl-D-alanylamide;

N-acetyl-D-3-(2-naphthyl)alanyl-D-3-(4-chlorophenyl)alanyl-N-alpha-aza-3-(3-quinolyl)alanyl-seryl-N-alpha-methyl-tyrosyl-D-lysyl(N-epsilon-nicotinyl)-leucyl-lysyl(N-epsilon-isopropyl)-prolyl-D-alanylamide; and N-acetyl-D-3-(2-naphthyl)alanyl-D-3-(4-chlorophenyl)alanyl-N-alpha-aza 3-(cyclohexyl)alanyl-seryl-N-alpha-methyl-tyrosyl-D-lysyl(N-epsilon-nicotinyl)-leucyl-lysyl(N-epsilon-isopropyl)-prolyl-D-alanylamide.

EXAMPLE 87

N-Ac-aza-Gly-D-4-Cl-Phe-D-1-Nal-N-Me-Ser-Tyr-D-Lys(N-epsilon-nicotinyl)-N-Me-Leu-Lys (N-epsilon-isopropyl)-Pro-D-AlaNH$_2$ The procedure described in Example 65 is used, but substituting Boc-Tyr(O-2-Br-Cbz) for Boc-N-Me-Tyr-(O-2,6-diCl-Bzl), and Boc-N-Me-Leu for Boc-Leu and adding 0.1% DMAP to the solutions of Boc-D-1-Nal and Boc-D-Lys(N-epsilon-FMOC). After HF treatment, workup, and HPLC purification N-Ac-aza-Gly-D-4-Cl-Phe-D-1-Nal-N-Me-Ser-Tyr-D-Lys(N-epsilon-

EXAMPLE 88

N-Ac-aza-Gly-D-4-Cl-Phe-D-1-Nal-N-Me-Ser-N-Me-Tyr-D-Lys (N-epsilon-nicotinyl)-Leu-Lys(N-epsilon-isopropyl)-Pro-D-AlaNH$_2$ The procedure described in Example 87 is used, but substituting Boc-N-Me-Tyr(O-2,6-diCl-Bzl) for Boc-Tyr(O-2-Br-Cbz), Boc-Leu for Boc-N-Me-Leu and adding 0.1% DMAP to the solution of Boc-N-Me-Ser-(O-Bzl) instead of Boc-D-Lys(N-epsilon-FMOC). After HF treatment, workup, and HPLC purification N-Ac-aza-Gly-D-4-Cl-Phe-D-1-Nal-N-Me-Ser-N-Me-Tyr-D-Lys(N-epsilon-nicotinyl)-Leu-Lys(N-epsilon-isopropyl)-Pro-D-AlaNH$_2$ can be obtained as the trifluoroacetate salt.

EXAMPLE 89

N-Ac-aza-Gly-D-4-Cl-Phe-D-1-Nal-Thr-N-Me-Tyr-D-Lys(N-epsilon-nicotinyl)-Leu-Lys (N-epsilon-isopropyl)-Pro-D-AlaNH$_2$ The procedure described in Example 65 is used, but substituting Boc-Thr(O-Bzl) for Boc-Ser(O-Bzl). After HF treatment, workup, and HPLC purification N-Ac-aza-Gly-D-4-Cl-Phe-D-1-Nal-N-Me-Ser-N-Me-Tyr-D-Lys (N-epsilon-nicotinyl)-Leu-Lys(N-epsilon-isopropyl)-Pro-D-AlaNH$_2$ can be obtained as the trifluoroacetate salt.

EXAMPLE 90

N-Ac-aza-Gly-D-4-Cl-Phe-D-1-Nal-N-Me-Ser-N-Me-Tyr-D-Lys (N-epsilon-nicotinyl)-N-Me-Leu-Lys(N-epsilon-isopropyl)-Pro-D-AlaNH$_2$ The procedure described in Example 65 is used, but substituting Boc-Ala for Boc-Ser(O-Bzl) and Boc-N-Me-Leu for Boc-Leu and adding 0.1% DMAP to the solution of Boc-Lys(N-epsilon-FMOC). After HF treatment, workup, and HPLC purification N-Ac-aza-Gly-D-4-Cl-Phe-D-1-Nal-Ala-N-Me-Tyr-D-Lys (N-epsilon-nicotinyl)-N-Me-Leu-Lys(N-epsilon-isopropyl)-Pro-D-AlaNH$_2$ can be obtained as the trifluoroacetate salt.

EXAMPLE 91

N-Ac-aza-Gly-D-4-Cl-Phe-D-1-Nal-Gln-N-Me-Tyr-D-Lys(N-epsilon-nicotinyl)-Leu-Lys (N-epsilon-isopropyl)-Pro-D-AlaNH$_2$ The procedure described in Example 65 is used, but substituting Boc-Gln for Boc-Ser(O-Bzl). After HF treatment, workup, and HPLC purification N-Ac-aza-Gly-D-4-Cl-Phe-D-1-Nal-Gln-N-Me-Tyr-D-Lys(N-epsilon-nicotinyl)-N-Me-Leu-Lys(N-epsilon-isopropyl)-Pro-D-AlaNH$_2$ can be obtained as the trifluoroacetate salt.

EXAMPLE 92

N-Ac-D-2-Nal-D-4-Cl-Phe-D-3-Pal-Ser-N-Me-Tyr(O-Me)-D-Lys (N-epsilon-nicotinyl)-Leu-Lys(N-epsilon-isopropyl)-Pro-D-AlaNH$_2$ The procedure described in Example 38 is used, but substituting Boc-N-Me-Tyr(O-Me) for Boc-N-Me-Tyr-(O-2,6-diCl-Bzl). After HF treatment, workup, and HPLC purification N-Ac-D-2-Nal-D-4-Cl-Phe-D-3-Pal-Ser-N-Me-Tyr(O-Me)-D-Lys (N-epsilon-nicotinyl)-Leu-Lys(N-epsilon-isopropyl)-Pro-D-AlaNH$_2$ can be obtained as the trifluoroacetate salt.

EXAMPLE 93

N-Ac-aza-Gly-D-4-Cl-Phe-D-1-Nal-Ser-N-Me-Tyr(O-Me)-D-Lys (N-epsilon-nicotinyl)-Leu-Lys(N-epsilon-isopropyl)-Pro-D-AlaNH$_2$ The procedure described in Example 65 is used, but substituting Boc-N-Me-Tyr(O-Me) for Boc N-Me-Tyr-(O-2,6-diCl-Bzl). After HF treatment, workup, and HPLC purification N-Ac-aza-Gly-D-4-Cl-Phe-D-1-Nal-Ser-N-Me-Tyr(O-Me)-D-Lys (N-epsilon-nicotinyl)-Leu-Lys(N-epsilon-isopropyl)-Pro-D-AlaNH$_2$ can be obtained as the trifluoroacetate salt.

EXAMPLE 94

N-Ac-aza-Gly-D-4-Cl-Phe-D-1-Nal-Ser-N-Me-Phe-D-Lys(N-epsilon-nicotinyl)-Leu-Lys (N-epsilon-isopropyl)-Pro-D-AlaNH$_2$ The procedure described in Example 93 is used, but substituting Boc-N-Me-Phe for Boc-N-Me-Tyr(O-2,6-diCl-Bzl). After HF treatment, workup, and HPLC purification N-Ac-aza-Gly-D-4-Cl-Phe-D-1-Nal-Ser-N-Me-Phe-D-Lys(N-epsilon-nicotinyl)-Leu-Lys (N-epsilon-isopropyl)-Pro-D-AlaNH$_2$ can be obtained as the trifluoroacetate salt.

EXAMPLE 95

N-Ac-aza-Gly-D-4-Cl-Phe-D-1-Nal-Ser-N-Me-4-F-Phe-D-Lys (N-epsilon-nicotinyl)-Leu-Lys(N-epsilon-isopropyl)-Pro-D-AlaNH$_2$ The procedure described in Example 94 is used, but substituting Boc-N-Me-4-F-Phe for Boc-N-Me-Phe. After HF treatment, workup, and HPLC purification N-Ac-aza-Gly-D-4-Cl-Phe-D-1-Nal-Ser-N-Me-4-F-Phe-D-Lys(N-epsilon-nicotinyl)-Leu-Lys(N-epsilon-isopropyl)-Pro-D-AlaNH$_2$ can be obtained as the trifluoroacetate salt.

EXAMPLE 96

N-Ac-Sar-D-4-Cl-Phe-D-3-Bal-Ser-N-Me-Tyr(O-Me)-D-Lys(N-epsilon-nicotinyl)-Leu-Lys (N-epsilon-isopropyl)-Pro-D-AlaNH$_2$ The procedure described in Example 63 is used, but substituting Boc-D-3-Bal for Boc-D-1-Nal and Boc-N-Me-Tyr(O-Me) for Boc-N-Me-Tyr(O-2,6-diCl-Bzl). After HF treatment, workup, and HPLC purification N-Ac-Sar-D-4-Cl-Phe-D-3-Bal-Ser-N-Me-Tyr(O-Me)-D-Lys(N-epsilon-nicotinyl)-Leu-Lys (N-epsilon-isopropyl)-Pro-D-AlaNH$_2$ can be obtained as the trifluoroacetate salt.

EXAMPLE 97

N-Ac-aza-Gly-D-4-Cl-Phe-D-1-Nal-Ser-N-Me-Arg-D-Lys(N-epsilon-nicotinyl)-Leu-Lys (N-epsilon-isopropyl)-Pro-D-AlaNH$_2$ The procedure described in Example 65 is used, but substituting Boc-N-Me-Arg(Tos) for Boc-N-Me-Tyr-(O-2,6-diCl-Bzl). After HF treatment, workup, and HPLC purification N-Ac-aza-Gly-D-4-Cl-Phe-D-1-Nal-Ser-N-Me-Arg-D-Lys(N-epsilon-nicotinyl)-Leu- Lys(N-epsilon-isopropyl)-Pro-D-AlaNH$_2$ can be obtained as the trifluoroacetate salt.

EXAMPLE 98

N-Ac-D-2-Nal-D-4-Cl-Phe-D-3-Pal-Ser-N-Me-Lys(N-epsilon-nicotinyl)-D-Lys
N-epsilon-nicotinyl)-Leu-Lys(N-epsilon-isopropyl)-Pro-D-AlaNH$_2$ The procedure described in Example 38 is used, but substituting Boc-N-Me-Lys(N-epsilon-FMOC) for Boc-N-Me-Tyr(O-2,6-diCl-Bzl) and after removal of the FMOC double amount of nicotinic acid is used for coupling. After HF treatment, workup, and HPLC purification N-Ac-D-2-Nal-D-4-Cl-Phe-D-3-Pal-Ser-N-Me-Lys(N-epsilon-nicotinyl)-D-Lys(N-epsilon-nicotinyl)-Leu-Lys(N-epsilon-isopropyl)-Pro-D-AlaNH$_2$ can be obtained as the trifluoroacetate salt.

EXAMPLE 99

N-Ac-D-2-Nal-D-4-Cl-Phe-D-3-Pal-Ser-N-Me-Orn(N-delta-nicotinyl)-D-Trp-Leu-Lys
(N-epsilon-isopropyl)-Pro-D-AlaNH$_2$ The procedure described in Example 98 is used, but substituting Boc-N-Me-Orn(N-delta-FMOC) for Boc-N-Me-Lys(N-epsilon-FMOC) and Boc-D-Trp for Boc-D-Lys(N-epsilon-FMOC) and without doubling the amount of nicotinic acid. After HF treatment, workup, and HPLC purification N-Ac-D-2-Nal-D-4-Cl-Phe-D-3-Pal-Ser-N-Me-Orn(N-delta-nicotinyl)D-Trp-Leu-Lys(N-epsilon-isopropyl)-Pro-D-AlaNH$_2$ can be obtained as the trifluoroacetate salt.

EXAMPLE 100

N-Ac-aza-Gly-D-4-Cl-Phe-D-1-Nal-Ser-N-Me-Arg-D-Lys(N-epsilon-anisic)-Leu-Arg-Pro-D-AlaNH$_2$ The procedure described in Example 97 is used, but substituting 4-methoxybenzoic acid for nicotinic acid and Boc-Arg(Tos) for Boc-Lys(N,N-epsilon-isopropyl,Cbz). After HF treatment, workup, and HPLC purification N-Ac-aza-Gly-D-4-Cl-Phe-D-1-Nal-Ser-N-Me-Arg-D-Lys(N-epsilon-anisic)-Leu-Arg-Pro-D-AlaNH$_2$ can be obtained as the trifluoroacetate salt.

EXAMPLE 101

N-Ac-D-2-Nal-D-4-Cl-Phe-D-3-Pal-Ser-N-Me-Arg-D-Lys(N-epsilon-anisic)-Leu-Lys
(N-epsilon-isopropyl)-Pro-D-AlaNH$_2$ The procedure described in Example 38 is used, but substituting Boc-N-Me-Arg(Tos) for Boc-N-Me-Tyr(O-2,6-diCl-Bzl), Boc-Arg(Tos) for Boc-Lys(N,N-epsilon-isopropyl, Cbz) and 4-methoxybenzoic acid for nicotinic acid. After HF treatment, workup, and HPLC purification N-Ac-D-2-Nal-D-4-Cl-Phe-D-3-Pal-Ser-N-Me-Arg-D-Lys(N-epsilon-nicotinyl)-Leu-Lys(N-epsilon-isopropyl)-Pro-D-AlaNH$_2$ can be obtained as the trifluoroacetate salt.

EXAMPLE 102

N-Ac-D-2-Nal-D-4-Cl-Phe-D-3-Pal-Ser-N-Me-Hcit(NH$_2$)-D-Lys
(N-epsilon-nicotinyl)-Leu-Lys(N-epsilon-isopropyl)-Pro-D-AlaNH$_2$ The procedure described in Example 38 is used, but substituting Boc-N-Me-Lys(N-epsilon-FMOC) for Boc-N-Me-Tyr(O-2,6-diCl-Bzl) and Boc-D-Lys(N-epsilon-nicotinyl) for Boc-D-Lys(N-epsilon-FMOC). With the completion of the synthesis, the resin is treated with 30% piperidine (30 mL) in DMF overnight to remove the FMOC group, washed (3×) with methylene chloride, and reacted with a solution of carbonyldiimidazole (1.13 g) in DMF (18 mL) for ten minutes, washed (3×) with methylene chloride, and then reacted overnight with a solution of anhydrous hydrazine (2 mL) in (1:1) methylene chloride/DMF (18 mL). The resin is washed (3×) with methylene chloride, dried, and treated with HF/anisole. After workup and HPLC purification N-Ac-D-2-Nal-D-4-Cl-Phe-D-3-Pal-Ser-N-Me-Hcit(NH$_2$)-D-Lys(N-epsilon-nicotinyl)-Leu-Lys(N-epsilon-isopropyl)-Pro-D-AlaNH$_2$ can be obtained as the trifluoroacetate salt.

EXAMPLE 103

N-Ac-D-2-Nal-D-4-Cl-Phe-D-3-Pal-Ser-N-Me-Hcit(N-HAc)-D-Lys
(N-epsilon-nicotinyl)-Leu-Lys(N-epsilon-isopropyl)-Pro-D-AlaNH$_2$ The procedure described in Example 102 is used, but substituting acetic hydrazide for anhydrous hydrazine. After HF treatment, workup, and HPLC purification N-Ac-D-2-Nal-D-4-Cl-Phe-D-3-Pal-Ser-N-Me-Hcit(N-HAc)-D-Lys(N-epsilon-nicotinyl)-Leu-Lys(N-epsilon-isopropyl)-Pro-D-AlaNH$_2$ can be obtained as the trifluoroacetate salt.

EXAMPLE 104

N-Ac-aza-Gly-D-4-Cl-Phe-D-Tmp-Ser-N-Me-Tyr-D-Lys(N-epsilon-nicotinic)-Leu-Lys
(N-epsilon-isopropyl)-Pro-D-AlaNH$_2$ The procedure described in Example 65 is used, but substituting Boc-D-Tmp for Boc-D-1-Nal. After HF treatment, workup, and HPLC purification N-Ac-aza-Gly-D-4-Cl-Phe-D-Tmp-Ser-N-Me-Tyr-D-Lys(N-epsilon-nicotinic)-Leu-Lys(N-epsilon-isopropyl)-Pro-D-AlaNH$_2$ can be obtained as the trifluoroacetate salt.

EXAMPLE 105

N-Ac-D-2-Nal-D-4-Cl-Phe-D-3-Pal-Ser-N-Me-Tyr-D-3-Bal-Leu-Lys (N-epsilon-isopropyl)-Pro-D-AlaNH$_2$ The procedure described in Example 38 is used, but substituting Boc-D-3-Bal for Boc-D-Lys (N-epsilon-FMOC). After HF treatment, workup, and HPLC purification N-Ac-D-2-Nal-D-4-Cl-Phe-D-3-Pal-Ser-N-Me-Tyr-D-3-Bal-Leu-Lys (N-epsilon-isopropyl)-Pro-D-AlaNH$_2$ can be obtained as the trifluoroacetate salt.

EXAMPLE 106

Using the procedure described in Example 105, but substituting Boc-D-3-Bal with the appropriate Boc-D-amino acids the following compounds can be obtained:
N-acetyl-D-3-(2-naphthyl)alanyl-D-3-(4-chlorophenyl)alanyl-D-3-(3-pyridyl)alanyl-seryl-N-alpha-methyl-tyrosyl-D-lysyl-leucyl-lysyl(N-epsilon-isopropyl)-prolyl-D-alanylamide;
N-acetyl-D-3-(2-naphthyl)alanyl-D-3-(4-chlorophenyl)alanyl-D-3-(3-pyridyl)alanyl-seryl-N-alpha-methyl-tyrosyl-D-ornithyl-leucyl-lysyl(N-epsilon-isopropyl)-pyrolyl-D-alanylamide;
N-acetyl-D-3-(2-naphthyl)alanyl-D-3-(4-chlorophenyl)alanyl-D-3-(3-pyridyl)alanyl-seryl-N-alpha-methyl-tyrosyl-D-citrullyl-leucyl-lysyl (N-epsilon-isopropyl-prolyl-D-alanylamide;

N-acetyl-D-3-(2-naphthyl)alanyl-D-3-(4-chlorophenyl)alanyl-D-3-(3-pyridyl)alanyl-seryl-N-alpha-methyltyrosyl-D-homocitrullyl-leucyl-lysyl (N-epsilon-isopropyl)-prolyl-D-alanylamide;

N-acetyl-D-3-(2-naphthyl)alanyl-D-3-(4-chlorophenyl)alanyl-D-3-(3-pyridyl)alanyl-seryl-N-alpha-methyltyrosyl-D-arginyl(N$^G$-diethyl)-leucyl-lysyl (N-epsilon-isopropyl)-prolyl-D-alanylamide; and N-acetyl-D-3-(2-naphthyl)alanyl-D-3-(4-chlorophenyl)alanyl-D-3-(3-pyridyl)alanyl-seryl-N-alpha-methyltyrosyl-D-arginyl-leucyl-lysyl (N-epsilon-isopropyl)-prolyl-D-alanylamide.

EXAMPLE 107

N-Ac-D-2-Nal-D-4-Cl-Phe-D-3-Pal-Ser-N-Me-Tyr-D-Lys (N-epsilon-anisic)-Leu-Lys(N-epsilon-isopropyl)-Pro-D-AlaNH$_2$ The procedure described in Example 62 is used, but substituting 4-methoxybenzoic acid for 2-pyrazinecarboxylic acid. After HF treatment, workup, and HPLC purification N-Ac-D-2-Nal-D-4-Cl-Phe-D-3-Pal-Ser-N-Me-Tyr-D-Lys(N-epsilon-anisic)-Leu-Lys(N-epsilon-isopropyl)-Pro-D-AlaNH$_2$ can be obtained as the trifluoroacetate salt.

EXAMPLE 108

N-Ac-D-2-Nal-D-4-Cl-Phe-D-1-Nal-Ser-N-Me-Tyr-D-Ser(O-alpha-L-Rha)-Leu-Lys (N-epsilon-isopropyl)-Pro-D-AlaNH$_2$ The peptide Leu-Lys(N,N-epsilon-isopropyl,Cbz)-Pro-D-AlaNH$_2$ is prepared by solid phase synthesis as described in Example 38. This peptide is coupled to N-alpha-FMOC-D-Ser(O-tri-Ac-alpha-L-Rhamnosyl)-OH in DMF and in the presence of DCC and HOBt to give after purification 4-D-Ser-(O-tri-Ac-L-Rhamnosyl)-Leu-Lys(N,N-epsilon-isopropyl,Cbz)-Pro-D-AlaNH$_2$. The obtained peptide is coupled to Boc-D-1-Nal-Ser-N-Me-Tyr-OH using the aforementioned conditions to give Boc-D-1-Nal-Ser-N-Me-Tyr-D-Ser-(O-tri-Ac-L-Rhamnosyl)-Leu-Lys(N,N-epsilon-isopropyl,Cbz)-Pro-D-AlaNH$_2$. The obtained peptide is purified and coupled to N-Ac-D-2-Nal-D-4-Cl-Phe-OH, using the aforementioned conditions, to give N-Ac-D-2-Nal-D-4-Cl-Phe-D-1-Nal-Ser-N-Me-Tyr-D-Ser-(O-tri-Ac-L-Rhamnosyl)-Leu-Lys(N,N-epsilon-isopropyl,Cbz)-Pro-D-AlaNH$_2$. The peptide is catalytically hydrogenated in methanol at pH 4.5 in the presence of Pd catalyst. At the end of the reaction the catalyst is filtered and the filtrate is concentrated in vacuo. The residue is dissolved in dimethylacetamide and treated with hydrazine hydrate for 4 hours at room temperature. After removal of the solvents in vacuo and HPLC purification of the residue N-Ac-D-2-Nal-D-4-Cl-Phe-D-1-Nal-Ser-N-Me-Tyr-D-Ser(O-alpha-L-Rha)-Leu-Lys(N-epsilon-isopropyl)-Pro-D-AlaNH$_2$ can be obtained as the trifluoroacetate salt.

EXAMPLE 109

N-Ac-D-2-Nal-D-4-Cl-Phe-D-3-Pal-Ser-N-Me-Tyr-D-Lys(N-epsilon-nicotinyl)-Cha-Lys (N-epsilon-isopropyl)-Pro-D-AlaNH$_2$ The procedure described in Example 38 is used, but substituting Boc-Cha for Boc-Leu. After HF treatment, workup, and HPLC purification N-Ac-D-2-Nal-D-4-Cl-Phe-D- 3-Pal-Ser-N-Me-Tyr-D-Lys(N-epsilon-nicotinyl)-Cha-Lys(N-epsilon-isopropyl)-Pro-D-AlaNH$_2$ can be obtained as the trifluoroacetate salt.

EXAMPLE 110

N-Ac-Sar-D-4-Cl-phe-D-1-Nal-Ser-N-Me-Tyr-D-Lys(N-epsilon-nicotinyl)-N-Me-Cha-Lys (N-epsilon-isopropyl)-Pro-D-AlaNH$_2$ The procedure described in Example 63 is used, but substituting Boc N-Me-Cha for Boc-Leu and adding 0.1% DMAP to the solution of Boc-D-Lys(N-epsilon-FMOC). After HF treatment, workup, and HPLC purification N-Ac-Sar-D-4-Cl-Phe-D-1-Nal-Ser-N-Me-Tyr-D-Lys(N-epsilon-nicotinyl)-N-Me-Cha-Lys(N-epsilon-isopropyl)-Pro-D-AlaNH$_2$ can be obtained as the trifluoroacetate salt.

EXAMPLE 111

N-Ac-aza-Gly-D-4-Cl-Phe-D-1-Nal-Ser-N-Me-Tyr-D-Lys(N-epsilon-nicotinyl)-Ileu-Lys (N-epsilon-isopropyl)-Pro-D-AlaNH$_2$ The procedure described in Example 65 is used, but substituting Boc-Leu with Boc-Ileu. After HF treatment, workup, and HPLC purification N-Ac-aza-Gly-D-4-Cl-Phe-D-1-Nal-Ser-N-Me-Tyr-D-Lys(N-epsilon-nicotinyl)-Ileu-Lys(N-epsilon-isopropyl)-Pro-D-AlaNH$_2$ can be obtained as the trifluoroacetate salt.

EXAMPLE 112

N-Ac-Sar-D-4-Cl-Phe-D-1-Nal-Ser-N-Me-Tyr-D-Lys(N-epsilon-nicotinyl)-Ser-Lys (N-epsilon-isopropyl)-Pro-D-AlaNH$_2$ The procedure described in Example 63 is used, but substituting Boc-Ser(O-Bzl) for Boc-Leu. After HF treatment, workup, and HPLC purification N-Ac-Sar-D-4-Cl-Phe-D-1-Nal-Ser-N-Me-Tyr-D-Lys(N-epsilon-nicotinyl)-Ser-Lys(N-epsilon-isopropyl)-Pro-D-AlaNH$_2$ can be obtained as the trifluoroacetate salt.

EXAMPLE 113

N-Ac-Sar-D-4-Cl-Phe-D-1-Nal-Ser-N-Me-Tyr-D-Lys(N-epsilon-nicotinyl)-Ser-N Me-Arg-Pro-D-AlaNH$_2$ The procedure described in Example 51 is used, but substituting Boc-N-Me-Arg(Tos) for Boc-Arg(Tos) and adding 0.1% DMAP to the Boc-Leu solution. After HF treatment, workup, and HPLC purification N-Ac-Sar-D-4-Cl-Phe-D-1-Nal-Ser-N-Me-Tyr-D-Lys(N-epsilon-nicotinyl)-Ser-N-Me-Arg-Pro-D-AlaNH$_2$ can be obtained as the trifluoroacetate salt.

EXAMPLE 114

N-Ac-D-2-Nal-D-4-Cl-Phe-D-3-Pal-Ser-N-Me-Tyr-D-Lys(N-epsilon-nicotinyl)-Leu-Lys-Pro-D-AlaNH$_2$ The procedure described in Example 38 is used, but substituting Boc-Lys(N-epsilon-Cbz) for Boc-Lys(N,N-epsilon-isopropyl,Cbz). After HF treatment, workup, and HPLC purification N-Ac-D-2-Nal-D-4-Cl-Phe-D-3-Pal-Ser-N-Me-Tyr-D-Lys (N-epsilon-nicotinyl)-Leu-Lys-Pro-D-AlaNH$_2$ can be obtained as the trifluoroacetate salt.

EXAMPLE 115

N-Ac-D-2-Nal-D-4-Cl-Phe-D-3-Pal-Ser-N-Me-Tyr-D-Lys(N-epsilon-nicotinyl)-Leu-Lys(N-epsilon-cyclohexyl)-Pro-D-AlaNH$_2$ The procedure described in Example 38 is used, but substituting Boc-Lys(N,N-epsilon-cyclohexyl,Cbz) for Boc-Lys(N,N-epsilon-isopropyl,Cbz). After HF treatment, workup, and HPLC purification N-Ac-D-2-Nal-D-4-Cl-Phe-D-3-Pal-Ser-N-Me-Tyr-D-Lys(N-epsilon-nicotinyl)-Leu-Lys(N-epsilon-cyclohexyl)-Pro-D-AlaNH$_2$ can be obtained as the trifluoroacetate salt.

EXAMPLE 116

N-Ac-D-2-Nal-D-4-Cl-Phe-D-3-Pal-Ser-N-Me-Tyr-D-Lys(N-epsilon-nicotinyl)-Leu-Hcit-Pro-D-AlaNH$_2$ The procedure described in Example 38 is used, but sustituting Boc-Hcit for Boc-Lys(N,N-epsilon-isopropyl,Cbz). After HF treatment, workup, and HPLC purification N-Ac-D-2-Nal-D-4-Cl-Phe-D-3-Pal-Ser-N-Me-Tyr-D-Lys(N-epsilon-nicotinyl)-Leu-Hcit-Pro-D-AlaNH$_2$ can be obtained as the trifluoroacetate salt.

EXAMPLE 117

N-Ac-D-2-Nal-D-4-Cl-Phe-D-3-Pal-Ser-N-Me-Tyr-D-Lys(N-epsilon-nicotinyl)-Leu-Lys(N-epsilon-CO-hyz)-Pro-D-AlaNH$_2$ The procedure described in Example 38 is used, but substituting Boc-Lys(N-epsilon-FMOC) for Boc-Lys(N,N-epsilon-isopropyl,Cbz) to give N-Ac-D-2-Nal-D-4-Cl-Phe-D-3-Pal-Ser(O-Bzl)-N-Me-Tyr(0-2,6-diCl-Bzl)-D-Lys(N-epsilon-nicotinyl)-Leu-Lys(N-epsilon-FMOC)-Pro-D-AlaNH-Resin. This resin is treated with 30% piperidine-DMF solution overnight, washed (3x) with methylene chloride, and then reacted with a solution of carbonyldiimidazole (1.13g) in DMF (18 mL) for 10 minutes, washed (3×) with methylene chloride and treated overnight with a solution of anhydrous hydrazine (1.5 mL) in (1:1) DMF/methylene chloride, dried, and treated with HF/anisole at 0° C. for 1 hour. After workup and HPLC purification N-Ac-D-2-Nal-D-4-Cl-Phe-D-3-Pal-Ser-N-Me-Tyr-D-Lys(N-epsilon-nicotinyl)-Leu-Lys(N-epsilon-CO-hyz)-Pro-D-AlaNH$_2$ can be obtained as the trifluoroacetate salt.

EXAMPLE 118

N-Ac-D-2-Nal-D-4-Cl-Phe-D-3-Pal-Ser-N-Me-Tyr-D Lys(N-epsilon-nicotinyl-Leu-Lys(N-epsilon-CO-hyzAc)-Pro-D-AlaNH$_2$ The procedure described in Example 117 is used, but substituting acetic hydrazide for anhydrous hydrazine. After HF treatment, workup, and HPLC purification N-Ac-D-2-Nal-D-4-Cl-Phe-D-3-Pal-Ser-N-Me-Tyr-D-Lys(N-epsilon-nicotinyl)-Leu-Lys(N-epsilon-CO-hyzAc)-Pro-D-AlaNH2 can be obtained as the trifluoroacetate salt.

EXAMPLE 119

N-Ac-Sar-D-4-Cl-Phe-D-1-Nal-Ser-N-Me-Tyr-D-Lys(N-epsilon-nicotinyl)-Leu-Lys(N-epsilon-isopropyl)-Pro-aza-GlyNH$_2$ The procedure described in Example 63 is used, but substituting Boc-aza-Gly-NH-Resin for Boc-D-Ala-NH-Resin. After HF treatment, workup, and HPLC purification N-Ac-Sar-D-4-Cl-Phe-D-1-Nal-Ser-N-Me-Tyr-D-Lys(N-epsilon-nicotinyl)-Leu-Lys(N-epsilon-isopropyl)-Pro-aza-GlyNH$_2$ can be obtained as the trifluoroacetate salt.

EXAMPLE 120

N-Ac-aza-Gly-D-4-Cl-Phe-D-1-Nal-Ser-N-Me-Tyr-D-Lys(N-epsilon-nicotinyl)-Leu-Lys(N-epsilon-isopropyl)-Pro-D-SerNH$_2$ The procedure described in Example 63 is used, but substituting Boc-D-Ser-NH-Resin for Boc-D-Ala-NH-Resin. After HF treatment, workup, an HPLC purification N-Ac-aza-Gly-D-4-Cl-Phe-D-1-Nal-Ser-N-Me-Tyr-D-lys(N-epsilon-nicotinyl)-Leu-Lys(N-epsilon-isopropyl)-Pro-D-SerNH$_2$ can be obtained as the trifluoroacetate salt.

EXAMPLE 121

N-Ac-D-2-Nal-D-4-Cl-Phe-D-3-Pal-Ser-NMe-Tyr-D-Lys(N-epsilon-nicotinyl)-Leu-Lys(N-epsilon-isopropyl)-Pro-AzaglyNH$_2$ The procedure described in Example 119 is used but substituting N-Ac-D-2-Nal for N-Ac-Sar and Boc-D-3-Pal for Boc-D-1-Nal to provide the title compound.

EXAMPLE 122

N-Ac-D-2Nal-D-4-Cl-Phe-D-3-Pal-Ser-N-Me-Arg-D-Mbha-Leu-Arg-Pro-D-AlaNH$_2$

The procedure described in Example 39 is used but substituting Boc-D-3-Pal for Boc-D-2-Thia, Boc-N-Me-Arg(Tos) for Boc-N-Me-Tyr(O-2,6-diCl-Bzl) and Boc-D-4-(4-methoxybenzolyl)Homoala for Boc-D-Lys(N-epsilon-Cbz) to provide the title compound.

EXAMPLE 124

N-Ac-D-2-Nal-D-4-Cl-Phe-D-3-Pal-Ser-N-Me-Tyr-D-Harg(N$^G$,N$^G$-diEt)-Leu-Harg(N$^G$,N$^G$-diEt)-Pro-D-AlaNH$_2$ The procedure described in Example 38 is used by substituting Boc-D-Homoarg(N$^G$,N$^G$-diEt) p-toluenesulfonate for Boc-Lys(N-epsilon-FMOC) and Boc-Homoarg(N$^G$,N$^G$-diEt) p-toluenesulfonate for Boc-Lys(N-epsilon-isopropyl,Cbz) to give the title compound.

EXAMPLE 125

N-Ac-D-2Nal-D-4-Cl-Phe-D-3Pal-Ser-NMeTyr-D-Cit-Leu-Arg-Pro-D-AlaNH$_2$

The procedure described in Example 39 is used but substituting Boc-D-3-Pal for Boc-2-Thia and Boc-D-Cit for Boc-D-Lys(N-epsilon-Cbz) to give the title compound.

Assay Procedures

The biological activities of the compounds of the invention are determined by the following assays:

(a) Receptor Binding

A radioligand receptor binding assay is performed in a similar way to that described in the literature (J. Marion et al., Mol. Pharmacol. 19 399 (1981)). [D-Leu$^6$-des Gly$^{10}$]-LHRH ethyl amide was radioiodinated by the chloramine-T method and used as the radioligand. Pituitary membranes containinq LHRH receptors are prepared in batches from quick-frozen rat pituitaries obtained from Hilltop Labs. The radioligand (50 pM), receptors, and compounds to be tested are coincubated for 2 hours at 4° C. Bound ligand is separated from free ligand via centrifugation and aspiration. Compounds are tested at six half-log concentration increments, and the negative log of the equilibrium dissociation constant ($pK_I$) is calculated from the concentration which displaces 50% of specifically bound radioligand.

(b) In vitro LH Release

This assay has been adopted from the literature (H. A. Jinnah and P. M. Conn, Endrocrinology 118 2599 (1986)). Rat pituitaries are removed from immature female rats, minced, and dissociated with collagenase/-hyaluronidase. They are allowed to attach to 48-well microtiter plates for 48–72 hours, then are exposed to test compounds for 3 hours at 37° C. The medium is assayed for released LH by RIA (radioimmunoassay). This assay is used to determine quantitatively the potencies of LHRH agonists from the negative log of the concentration which produces half-maximal release of LH ($pD_2$)

For assaying LHRH antagonists, exogenous superagonist [D Leu$^6$-Pro$^9$NHEt]LHRH is added. The suppression of LH release by the antagonist is dose related. The assay determines the potencies of the LHRH antagonists from the negative log of the concentration which produces half-maximum suppression of LH ($pA_2$).

(c) In vivo LH Release

The compound to be tested is administered to castrated rats intraveneously and the serum LH concentration at various time points is measured by RIA. The time integrated LH response is calculated and the dose producing half-maximal LH release ($ED_{50}$) is reported.

(d) In vivo LH Inhibition

The compound to be tested is administered at 30 μg/kg subcutaneously by bolus injection to male castrate rats and blood samples are collected periodically over 24 hours. The AUC (area under the curve) of the LH supression data as a function of time is calculated using the formula log ($LH_t/LH_i$) wherein $LH_t$ is the LH concentration in the blood at time t and $LH_i$ is the initial baseline value for the concentration of LH in the blood. The AUC values are negative numbers.

(e) Stability against enzymatic deqradation

The intestinal stability of the compounds of the invention was determined using in vitro rat jejunum in a reperfusion system. The fractional mucosal loss was an indicator of the relative rate of deqradation of the compounds thirty minutes after introduction of the luminal bath. See FIG. 1.

The in vitro and in vivo biological activities of representative compounds are shown below:

| Compound # | Receptor Binding $pK_I$ | LH Release $pD_2$ | $ED_{50}$ ug/kg i.v. |
|---|---|---|---|
| Ex. 1 | 8.93 | 9.43 | 7.20 |
| Ex. 3 | 10.4 | 11.3 | 0.129 |
| Ex. 7 | | 9.73 | 9.64 |
| Ex. 12 | 8.98 | 9.31 | 9.90 |
| Ex. 13 | 10.42 | 8.50 | |
| Ex. 14 | 9.43 | 9.61 | 0.39 |
| Ex. 15 | 10.1 | 10.1 | 1.38 |
| Ex. 16 | 9.24 | 9.29 | |
| Ex. 19 | 10.42 | 8.51 | |
| Ex. 20 | 10.80 | 10.50 | |

| | | | -continued |
|---|---|---|---|
| Ex. 21 | 9.34 | 9.57 | |
| Ex. 22 | 9.16 | 9.60 | |
| Ex. 23 | 10.25 | 9.90 | |
| LHRH | 8.90 | 9.27 | 100 |
| *** | 10.3 | 10.14 | 0.12 |

| Compound # | Receptor Binding $pK_I$ | LH Inhibition $pA_2$ | AUC (24 hr. after 30 ug/kg) |
|---|---|---|---|
| Ex. 35 | 9.32 | 9.35 | −510 |
| Ex. 38 | 10.50 | 11.23 | −1000 |
| Ex. 39 | 10.45 | 10.35 | −656 |
| Ex. 42 | 9.22 | 8.81 | |
| Ex. 43 | 10.47 | 11.25 | −337 |
| Ex. 44 | 10.48 | 11.30 | −571 |
| Ex. 45 | 10.86 | 11.15 | −690 |
| Ex. 46 | 10.56 | 11.15 | −1513 |
| Ex. 47 | 10.42 | 10.35 | −1200 |
| Ex. 48 | 11.00 | 11.15 | −916 |
| Ex. 49 | 10.50 | 9.71 | |
| Ex. 50 | 10.86 | 11.15 | |
| Ex. 51 | 10.57 | 11.45 | −526 |
| Ex. 52 | 10.77 | 10.90 | −1483 |
| Ex. 53 | 10.88 | 11.40 | |
| Ex. 54 | 10.47 | 11.20 | −963 |
| Ex. 55 | 10.66 | 11.15 | −790 |
| Ex. 56 | 9.17 | 9.71 | |
| Ex. 57 | 9.43 | 9.15 | |
| Ex. 58 | 11.06 | 10.35 | |
| Ex. 59 | 10.01 | 10.45 | |
| Ex. 60 | 10.64 | 10.75 | |
| Ex. 61 | 10.31 | 10.39 | |
| Ex. 62 | 10.36 | 10.60 | |
| Ex. 63 | 10.35 | 11.20 | −707 |
| Ex. 64 | 10.99 | 11.20 | |
| Ex. 65 | 10.24 | 11.25 | −1114 |
| Ex. 66 | 10.85 | 11.50 | |
| Ex. 67 | 10.52 | 10.60 | −400 |
| Ex. 68 | 9.92 | 11.00 | |
| Ex. 69 | 10.77 | 11.00 | −467 |
| Ex. 70 | 10.92 | 11.30 | |

*** - [D-Leu$^6$-desGly$^{10}$]LHRH-Et amide.

The foregoing is merely illustrative of the invention and is not intended to limit the invention to the disclosed compounds. Variations and changes which are obvious to one skilled in the art are intended to be within the scope and nature of the invention which are defined in the appended claims.

What is claimed is:

1. A peptide of the formula:

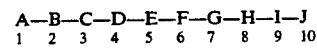

wherein
A is an amino acyl residue selected from the group consisting of
N-acetyl-D-3-(2-naphthyl)alanine,
N-acetyl-sarcosyl,
N-acetyl-D-phenylalanyl,
N-acetyl-D-(4-chlorophenyl)alanyl, and
B is an amino acyl residue selected from the group consisting of
D-3-(4-chlorophenyl)alanyl,
D-3-(4-fluorophenyl)alanyl,
D-phenylalanyl, and
D-3-(2-naphthyl)alanyl;
C is an amino acyl residue selected from the group consisting of
D-3-(3-pyridyl)alanyl,
D-3-(1-naphthyl)alanyl,
D-3-(2-thiazolyl)alanyl, and
D-3-(2-benzo[b]thienyl)alanyl, D is an amino acyl residue selected from the group consisting of
L-seryl,
N-(R⁰)-L-seryl,
E is an amino acyl residue selected from the group consisting of
N-(R⁰)-L-tyrosyl,
N-(R⁰)-L-tyrosyl(O-methyl),
N-(R⁰)-L-phenylalanyl,
N-(R⁰)-L-3-cyclohexylalanyl,
F is an amino acyl residue selected from the group consisting of
D-trypyl,
D-3-(3-pyridyl)alanyl,
D-seryl,
D-[epsilon-N-(N'-morpholinylcarbonyl)]lysyl,
D-[epsilon-N-(2-pyrazinyl)carbonyl]lysyl,
D-[epsilon-N-(N'-piperidinyl-N'-methyl)carbonyl]lysyl,
D-[epsilon-N-(3-quinolinyl)carbonyl]lysyl, and
D-(epsilon-N-nicotinoyl)lysyl;
G is an amino acyl residue selected from the group consisting of
L-leucyl,
L-valyl,
L-cyclohexylalanyl,
N-(R⁰)-L-cyclohexylalanyl,
N-(R⁰)-L-leucyl;
H is an amino acyl residue selected from the group consisting of
L-(epsilon-N-isopropyl)lysyl,
N-(R⁰)-L-arginyl, and
L-arginyl;
I is an amino acyl residue selected from the group consisting of
L-prolyl,
N-(R⁰)-L-alanyl; and
J is —NH(CH₂CH₃) or is an amino acyl residue selected from the group consisting of
D-alaninamide,
N-(R⁰)-D-alaninamide,
N-(R⁰)-L-alaninamide,
sarcosamide,
alpha-aza-glycinamide,
D-serinamide, and
wherein R⁰ is alkyl of from one to four carbon atoms; provided that when J is —NH(CH₂CH₃), I is L-prolyl.

2. A peptide as defined by claim 1 wherein R⁰ is methyl.

3. A peptide of the formula:

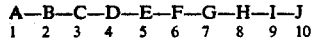

wherein
A is an amino acyl residue selected from the group consisting of
N-acetyl-sarcosyl,
N-acetyl-D-3-(2-naphthyl)alanine,
B is an amino acyl residue selected from the group consisting of
D-3-(4-chlorophenyl)alanyl,
D-3-(4-fluorophenyl)alanyl,
C is an amino acyl residue selected from the group consisting of
D-3-(3-pyridyl)alanyl,
D-3-(1-naphthyl)alanyl,
D-3-(2-benzo[b]thienyl)alanyl,
D is an amino acyl residue selected from the group consisting of
L-seryl,
N-methyl-L-seryl,
E is an amino acyl residue selected from the group consisting of
N-methyl-L-tyrosyl,
N-methyl-L-tyrosyl(O-methyl),
N-methyl-L-3-cyclohexylalanyl,
F is an amino acyl residue selected from the group consisting of
D-trypyl,
D-[epsilon-N-(N'-morpholinylcarbonyl)]lysyl,
D-[epsilon-N-(3-quinolinyl)carbonyl]lysyl, and
D-(epsilon-N-nicotinoyl)lysyl;
G is an amino acyl residue selected from the group consisting of
L-leucyl,
N-methyl-D-leucyl, and
N-methyl-L-leucyl;
H is an amino acyl residue selected from the group consisting of
L-(epsilon-N-isopropyl)lysyl,
N-methyl-L-arginyl, and
L-arginyl;
I is an amino acyl residue selected from the group consisting of
L-prolyl,
N-methyl-L-alanyl; and
J is —NH(CH₂CH₃) or is an amino acyl residue selected from the group consisting of
D-alaninamide,
sarcosamide,
alpha-aza-glycinamide,
D-serinamide, and
provided that when J is —NH(CH₂CH₃), I is L-prolyl.

4. A peptide of the formula:

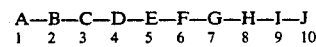

wherein
A is an amino acyl residue selected from the group consisting of
N-acetyl-sarcosyl,
N-acetyl-D-3-(2-naphthyl)alanine,
B is an amino acyl residue selected from the group consisting of
D-3-(4-chlorophenyl)alanyl,
C is an amino acyl residue selected from the group consisting of
D-3-(3-pyridyl)alanyl,
D-3-(1-naphthyl)alanyl,
D-3-(2-benzo[b]thienyl)alanyl,
D is an amino acyl residue selected from the group consisting of
L-seryl,
N-methyl-L-seryl,
E is an amino acyl residue selected from the group consisting of
N-methyl-L-tyrosyl,
N-methyl-L-tyrosyl(O-methyl),
F is an amino acyl residue selected from the group consisting of
D-[epsilon-N-(N'-morpholinylcarbonyl)]lysyl,
D-(epsilon-N-nicotinoyl)lysyl;
G is an amino acyl residue selected from the group consisting of L-leucyl, H is an amino acyl residue selected from the group consisting of
L-(epsilon-N-isopropyl)lysyl, and
L-arginyl;

I is an amino acyl residue selected from the group consisting of
L-prolyl, and

J is —NH(CH$_2$CH$_3$) or is an amino acyl residue selected from the group consisting of
D-alaninamide,
sarcosamide,
D-serinamide, and provided that when J is —NH(CH$_2$CH$_3$), I is L-prolyl.

5. A compound selected from the group consisting of:
N-Ac-D-4-Cl-Phe-D-4-Cl-Phe-D-2-Thia-N-Me-Ser-Tyr-D-Lys-Leu-Arg-Pro-D-AlaNH$_2$;
N-Ac-D-4-Cl-Phe-D-4-Cl-Phe-D-2-Thia-Ser-N-Me-Tyr-D-Lys-Leu-Arg-Pro-AlaNH$_2$;
N-Ac-D-4-Cl-Phe-D-4-Cl-Phe-D-2-Thia-Ser-Tyr-D-Lys-Leu-Arg-Pro-SarNH$_2$;
N-Ac-D-4-Cl-Phe-N-Me-D-4-Cl-Phe-D-2-Thia-Ser-Tyr-D-Lys-Leu-Arg-Pro-D-AlaNH$_2$;
N-Ac-D-4-Cl-Phe-D-4-Cl-Phe-D-2-Thia-Ser-Tyr-N-Me-D-Lys-Leu-Arg-Pro-D-AlaNH$_2$;
N-Ac-D-2-Nal-N-Me-D-4-Cl-Phe-D-3-Pal-Ser-Lys(N-epsilon-nicotinyl)-D-Lys(N-epsilon-nicotinyl)-Leu-Lys(N-epsilon-isopropyl)-Pro-D-AlaNH$_2$;
N-Ac-D-4-Cl-Phe-D-4-Cl-Phe-D-2-Thia-Ser-N-Me-Tyr-D-Lys-Leu-Arg-Pro-D-AlaNH$_2$;
N-Ac-D-4-Cl-Phe-D-4-Cl-Phe-D-2-Thia-N-Me-Ser-Tyr-D-Lys-Leu-Arg-Pro-D-AlaNH$_2$;
N-Ac-D-2-Nal-D-4-Cl-Phe-D-3-Pal-N-Me-Ser-Lys(N-epsilon-nicotinyl)-D-Lys(N-epsilon-nicotinyl)-Leu-Lys(N-epsilon-isopropyl)-Pro-D-AlaNH$_2$;
pyro-Glu-His-Trp-Ser-N-Me-Tyr-D-Leu-Arg-ProNHEt;
pyro-Glu-N-Me-Phe-Trp-Ser-Tyr-D-Trp-D-Leu-Arg-ProNHEt;
pyro-Glu-His-Trp-Ser-N-Me-Tyr-D-Ser(O-t-butyl)-Leu-Arg-ProNHEt;
pyro-Glu-His-Trp-N-Me-Ser-Tyr-D-2-Nal-Leu-Arg-ProGlyNH$_2$;
pyro-Glu-His-Trp-Ser-N-Me-Tyr-D-Trp-Leu-Arg-Pro-azaGlyNH$_2$;
pyro-Glu-His-Trp-Ser-N-Me-Tyr-D-Trp-N-Me-Leu-Arg-Pro-Gly-NH$_2$;
pyro-Glu-His-Trp-N-MeSer-N-Me-Tyr-D-Trp-Leu-Arg-Pro-NHEt; and
N-Ac-D-4-Cl-Phe-D-4-Cl-Phe-D-2-Thia-Ser-Tyr-D-Lys-Leu-N-Me-Arg-Pro-D-AlaNH$_2$.

6. N-Ac-D-2-Nal-D-4-Cl-Phe-D-3-Pal-Ser-N-Me-Tyr-D-Lys(N-epsilon-nicotinyl)-Leu-Lys(N-epsilon-isopropyl)-Pro-D-AlaNH$_2$; or a pharmaceutically acceptable salt thereof.

7. A method for suppressing levels of sex hormones in male or female mammals comprising administering to a host in need of such treatment a therapeutically effective amount of an LHRH antagonist compound of claim 1.

8. A pharmaceutical composition for suppressing levels of sex hormones in male and female mammals, comprising a pharmaecutical carrier and a therapeutically effective amount of an LHRH antagonist compound of claim 1.

9. A method for suppressing levels of sex hormones in male or female mammals comprising administering to a host in need of such treatment a therapeutically effective amount of a compound of claim 1 in combination with a therapeutically effective amount of an antiandrogenic agent.

10. A method for suppressing levels of sex hormones in male or female mammals comprising administering to a host in need of such treatment a therapeutically effective amount of an LHRH compounds of claim 1 antagonist in combination with a therapeutically effective amount of an antiandrogenic agent.

* * * * *